US005639726A

United States Patent [19]
Lawrence et al.

[11] Patent Number: 5,639,726
[45] Date of Patent: Jun. 17, 1997

[54] PEPTIDE MEDIATED ENHANCEMENT OF THROMBOLYSIS METHODS AND COMPOSITIONS

[75] Inventors: Daniel A. Lawrence; David Ginsburg, both of Ann Arbor; Joseph D. Shore, Grosse Point Farms; William P. Fay, Ann Arbor, all of Mich.; Steven T. Olson, Chicago, Ill.; Ann Marie Francis-Chmura, Warren, Mich.; Daniel T. Eitzman, Ypsilanti, Mich.; Dell Paielli, Wyandotte, Mich.

[73] Assignees: The Regents of the University of Michigan, Ann Arbor; Henry Ford Health System, Detroit, both of Mich.

[21] Appl. No.: 315,461

[22] Filed: Sep. 30, 1994

[51] Int. Cl.$^6$ .......................... A61K 38/00; A61K 38/02; C07K 5/00; C07K 7/00
[52] U.S. Cl. ............... 514/12; 514/13; 514/14; 514/15; 514/16; 530/324; 530/325; 530/326; 530/327; 530/328
[58] Field of Search ................... 530/324, 325, 530/326, 327, 328; 514/12, 13, 14, 15, 16

[56] References Cited

U.S. PATENT DOCUMENTS

| | | | |
|---|---|---|---|
| 4,923,807 | 5/1990 | Webb et al. | 435/69.2 |
| 4,929,602 | 5/1990 | Harker et al. | 514/18 |
| 4,952,512 | 8/1990 | Loskutoff et al. | 435/320 |
| 5,039,791 | 8/1991 | Wittwer et al. | 530/324 |
| 5,057,414 | 10/1991 | Stief et al. | 435/13 |
| 5,061,693 | 10/1991 | Nutt et al. | 514/17 |
| 5,096,811 | 3/1992 | Hotchkiss et al. | 435/13 |
| 5,106,741 | 4/1992 | Marotti et al. | 435/226 |
| 5,134,065 | 7/1992 | Sanzo et al. | 435/703 |

FOREIGN PATENT DOCUMENTS

3713272  11/1988  Germany.

OTHER PUBLICATIONS

Skeggs et al., *J. of Exp. Med.*, vol. 106, pp. 439–453, 1957.
Oliner, *Hypertension*, vol. 11, No. 1, Jan. 1988 pp. 21–27.
Carrell et al., "Mobile Reactive Centre of Serpins and the Control of Thrombosis," *Nature*, 353:576–578, Oct. 1991.
Marder, "Inhibiting the Inhibitor," *Circulation*, 85:386–387, 1992.
Angleton PW, Chandler WL and Schmer G, Diurnal variation of tissue–type plasminogen activator and its rapid inhibitor (PAI–1). *Circulation* 1989; 79:101–106.
Björk I, Ylinenjärvi K, Olson ST, and Bock PE, Conversion of antithrombin from an inhibitor of thrombin to a substrate with reduced heparin affinity and enhanced conformational stability by binding of a tetradecapeptide corresponding to the $P_1$ to $P_{14}$ region of the putative reactive bond loop of the inhibitor. *J. Biol. Chem.* 1992; 267:1976–1982.

Braaten JV, Handt S, Jerome WG, Kirkpatrick J, Lewis JC, and Hantgan RR, Regulation of fibrinolysis by platelet–released plasminogen activator inhibitor 1: Light scattering and ultrastructural examination of lysis of a model platelet–fibrin thrombus. *Blood* 1993; 81:1290–1299.
Carmeliet P, Stassen JM, Schoonjans L, Ream B, van den Oord JJ, De Mol M, et al., Plasminogen activator inhibitor–1 gene–deficient mice. II. Effects on hemostasis, thrombosis, and thrombolysis. *J. Clin. Invest.* 1993; 92:2756–2760.
Erickson LA, Fici GJ, Lund JE, Boyle TP, Polites G, and Marotti KR, Development of venous occlusions in mice transgenic for the plasminogen activator inhibitor–1 gene. *Nature* 1990; 346:74–76.
Fay WP, Eitzman DT, Shaprio AD, Madison EL, and Ginsburg D, Platelets inhibit fibrinolysis in vitro by both plasminogen activator inhibitor–1 dependent and independent mechanisms. *Blood* 1994; 83:351–356.
Ginsburg D, Zeheb R, Yang AY, Rafferty UM, Andreasen PA, Nielsen L, et al., cDNA cloning of human plasminogen activator–inhibitor from endothelial cells. *J. Clin. Invest.* 1986; 78:1673–1680.
Hamsten A, de Faire, Walldius G, Dahlen, Szamosi A, Landou C, Blombäck M, and Wiman B, Plasminogen activator inhibitor in plasma: risk factor for recurrent myocardial infraction. *Lancet* 1987; 2:3–9.
Hamsten A, Wiman B, de Faire U, Blombäck M. Increased plasma levels of a rapid inhibitor of tissue plasminogen activator in young survivors of myocardial infarction. *New Engl. J. Med.* 1985; 313:1557–1563.
Jang I–K, Gold HK, Ziskind AA, Fallon JT, Holt RE, Leinbach RC, et al., Differential sensitivity of erythrocyte–rich and platlet–rich arterial thrombi to lysis with recombinant tissue–type plasminogen activator. *Circulation* 1989; 79:920–928.
Lawrence DA, Olson ST, Palaniappan S, and Ginsburg D, Serpin reactive–center loop mobility is required for stable inhibition but not for enzyme recognition. *J. Biol. Chem.* 1994; 269;27657–27662.
Levi M, Biemond BJ, van Zonneveld A–J, Wouter Ten Cate J, and Pannekoek H; Inhibition of plasminogen activator inhibitor–1 activity results in promotion of endogenous thrombolysis and inhibition of thrombus extension in models of experimental thrombosis. *Circulation* 1992; 85:305–312.
Ny T, Sawdey M, Lawrence D, Millan JL, and Loskutoff DJ, Cloning and sequence of a cDNA coding for the human β–migrating endothelial–cell–type plasminogen activator inhibitor. *Proc. Natl. Acad. Sci. USA* 1986; 83:6776–6780.

(List continued on next page.)

*Primary Examiner*—Avis M. Davenport
*Attorney, Agent, or Firm*—Arnold, White & Durkee

[57] ABSTRACT

The invention relates generally to peptides which decrease the half-life of active plasminogen activator inhibitor-1. This invention further relates to methods and compositions for using peptides which decrease the half-life of active plasminogen activator inhibitor-1. Further, the invention includes methods and compositions useful in clot lysis.

59 Claims, 10 Drawing Sheets

OTHER PUBLICATIONS

Potter van Loon BJ, Rijken DC, Brommer EJP and Van der Maas APC, The amount of plasminogen, tissue–type plasminogen activator and plasminogen activator inhibitor type 1 in human thrombi and the relation to ex–vivo lysibility. *Thromb Haemost* 1992; 67:101–105.

Reilly CF and Hutzelmann JE, Plasminogen activator inhibitor–1 binds to fibrin and inhibits tissue–type plasminogen activtor–mediated fibrin dissolution. *J. Biol. Chem.* 1992; 267:17128–17135.

Schneiderman J, Sawdey MS, Keeton MR, Bordin GM, Bernstein EF, Dilley RB, et al, Increased type 1 plasminogen activator inhibitor gene expression in atherosclerotic human arteries. *Proc. Natl. Acad. Sci. USA* 1992; 89:6998–7002.

Schulze AJ, Baumann U, Knof S, Jaeger E, Huber R, and Laurell C, Structural transition of $a_1$–antitrypsin by a peptide sequentially similar to β–strand s4A. *Eur. J. Biochem.* 1990; 194:51–56.

Schulze AJ, Frohnert PW, Engh RA, and Huber R, Evidence for the extent of insertion of the active site loop of intact $\alpha^1$ proteinase inhibitor in β–sheet A. *Biochem.* 1992; 31:7560–7565.

Schulze AJ, Huber R, Bode W, and Engh RA, Structural aspects of serpin inhibition. *Fed. of Eur. Biochem. Soc.* 1994; 344:117–124.

Schulze AJ, Huber R, Degryse E, Speck D, and Bischoff R, Inhibitory activity and conformational transition of $\alpha_1$–proteinase inhibitor variants. *Eur. J. Biochem.* 1991; 202:1147–1155.

van Mourik JA, Lawrence DA, and Loskutoff DJ, Purification of an inhibitor plasminogen activator (anitactivator) synthesized by endothelial cells. *J. Biol. Chem.* 1984; 259:14914–14921.

Wiman M. and Hamsten A, The fibrinolytic enzyme system and its role in the etiology of thromboembolic disease. *Thromb Haemost* 1990; 16:207–216.

| Residue | P14 356 | | | | | | P7 363 | | | | | P1 369 | | | |
|---|---|---|---|---|---|---|---|---|---|---|---|---|---|---|---|
| PAI | T | V | A | S | S | S | T | A | V | I | V | S | A | R | (SEQ ID NO: 1) |
| wtPAI-8mer | T | V | A | S | S | S | T | A | | | | | | | (SEQ ID NO: 2) |
| V→E PAI-8mer | T | E | A | S | S | S | T | A | | | | | | | (SEQ ID NO: 3) |
| Consensus-8mer | T | E | A | A | A | A | T | G | | | | | | | (SEQ ID NO: 4) |
| Consensus-14mer | T | E | A | A | A | A | T | G | A | A | A | T | G | R | (SEQ ID NO: 5) |

*Fig. 1*

SEQUENCE LISTING ( 1 ) GENERAL INFORMATION:

( i i i ) NUMBER OF SEQUENCES: 7

( 2 ) INFORMATION FOR SEQ ID NO:1:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

```
Thr Val Ala Ser Ser Ser Thr Ala Val Ile Val Ser Ala Arg
1               5                   10
```

( 2 ) INFORMATION FOR SEQ ID NO:2:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

```
Thr Val Ala Ser Ser Ser Thr Ala
1               5
```

( 2 ) INFORMATION FOR SEQ ID NO:3:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

```
Thr Glu Ala Ser Ser Ser Thr Ala
1               5
```

( 2 ) INFORMATION FOR SEQ ID NO:4:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

```
Thr Glu Ala Ala Ala Ala Thr Gly
1               5
```

( 2 ) INFORMATION FOR SEQ ID NO:5:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear 5,639,726

(i i) MOLECULE TYPE: peptide (x i) SEQUENCE DESCRIPTION: SEQ ID NO:5:

Thr Glu Ala Ala Ala Ala Thr Gly Ala Ala Ala Thr Gly Arg
1               5                   10

(2) INFORMATION FOR SEQ ID NO:6:

(i) SEQUENCE CHARACTERISTICS:
  (A) LENGTH: 14 amino acids
  (B) TYPE: amino acid
  (C) STRANDEDNESS: single
  (D) TOPOLOGY: linear (i i) MOLECULE TYPE: peptide (x i) SEQUENCE DESCRIPTION: SEQ ID NO:6:

Asp Arg Val Tyr Ile His Pro Phe His Leu Leu Val Tyr Ser
1               5                   10

(2) INFORMATION FOR SEQ ID NO:7:

(i) SEQUENCE CHARACTERISTICS:
  (A) LENGTH: 402 amino acids
  (B) TYPE: amino acid
  (C) STRANDEDNESS: single
  (D) TOPOLOGY: linear (i i) MOLECULE TYPE: protein (x i) SEQUENCE DESCRIPTION: SEQ ID NO:7:

Met Gln Met Ser Pro Ala Leu Thr Cys Leu Val Leu Gly Leu Ala Leu
1               5                   10                  15

Val Phe Gly Glu Gly Ser Ala Val His His Pro Pro Ser Tyr Val Ala
                20                  25                  30

His Leu Ala Ser Asp Phe Gly Val Arg Val Phe Gln Gln Val Ala Gln
            35                  40                  45

Ala Ser Lys Asp Arg Asn Val Val Phe Ser Pro Tyr Gly Val Ala Ser
        50                  55                  60

Val Leu Ala Met Leu Gln Leu Thr Thr Gly Gly Glu Thr Gln Gln Gln
65                  70                  75                  80

Ile Gln Ala Ala Met Gly Phe Lys Ile Asp Asp Lys Gly Met Ala Pro
                85                  90                  95

Ala Leu Arg His Leu Tyr Lys Glu Leu Met Gly Pro Trp Asn Lys Asp
                100                 105                 110

Glu Ile Ser Thr Thr Asp Ala Ile Phe Val Gln Arg Asp Leu Lys Leu
            115                 120                 125

Val Gln Gly Phe Met Pro His Phe Phe Arg Leu Phe Arg Ser Thr Val
        130                 135                 140

Lys Gln Val Asp Phe Ser Glu Val Glu Arg Ala Arg Phe Ile Ile Asn
145                 150                 155                 160

Asp Trp Val Lys Thr His Thr Lys Gly Met Ile Ser Asn Leu Leu Gly
                165                 170                 175

Lys Gly Ala Val Asp Gln Leu Thr Arg Leu Val Leu Val Asn Ala Leu
                180                 185                 190

Tyr Phe Asn Gly Gln Trp Lys Thr Pro Phe Pro Asp Ser Ser Thr His
            195                 200                 205

Arg Arg Leu Phe His Lys Ser Asp Gly Ser Thr Val Ser Val Pro Met
        210                 215                 220

Met Ala Gln Thr Asn Lys Phe Asn Tyr Thr Glu Phe Thr Thr Pro Asp
225                 230                 235                 240

```
Gly His Tyr Tyr Asp Ile Leu Glu Leu Pro Tyr His Gly Asp Thr Leu
            245                     250                 255

Ser Met Phe Ile Ala Ala Pro Tyr Glu Lys Glu Val Pro Leu Ser Ala
            260                 265                 270

Leu Thr Asn Ile Leu Ser Ala Gln Leu Ile Ser His Trp Lys Gly Asn
        275                 280                 285

Met Thr Arg Leu Pro Arg Leu Leu Val Leu Pro Lys Phe Ser Leu Glu
    290                 295                 300

Thr Glu Val Asp Leu Arg Lys Pro Leu Glu Asn Leu Gly Met Thr Asp
305                     310                 315                 320

Met Phe Arg Gln Phe Gln Ala Asp Phe Thr Ser Leu Ser Asp Gln Glu
            325                     330                 335

Pro Leu His Val Ala Gln Ala Leu Gln Lys Val Lys Ile Glu Val Asn
            340                 345                 350

Glu Ser Gly Thr Val Ala Ser Ser Ser Thr Ala Val Ile Val Ser Ala
        355             360                 365

Arg Met Ala Pro Glu Glu Ile Ile Met Asp Arg Pro Phe Leu Phe Val
    370                 375                 380

Val Arg His Asn Pro Thr Gly Thr Val Leu Phe Met Gly Gln Val Met
385             390                 395                 400

Glu Pro
```

PEPTIDE MEDIATED ENHANCEMENT OF THROMBOLYSIS METHODS AND COMPOSITIONS

The United States government may own certain rights in the present invention pursuant to grants HL39888, HL45930, HL39137 and HL08572.

FIELD OF THE INVENTION

This invention relates generally to methods and compositions for reducing the half-life of active plasminogen activator inhibitor-1. The invention relates as well to peptides that decrease the half-life of plasminogen activator inhibitor-1. Further, this invention provides methods and compositions for promoting clot lysis by reducing the half-life of plasminogen activator inhibitor-1. In addition, methods and compositions for therapeutic uses of peptides which promote clot lysis are provided.

BACKGROUND

Atherosclerotic coronary artery disease is a major cause of morbidity and mortality in western nations. A number of risk factors have been identified that can dramatically increase the risk of developing atherosclerotic disease. One of these factors is high serum cholesterol levels. Fat and cholesterol deposit on blood vessel walls, straining the blood flow. This eventually causes injury at the site and leads to the formation of damaging blood clots. When these blood clots reach the heart, they are life threatening.

Another risk factor for atherosclerotic disease, identified in a large number of studies, is elevated blood levels of plasminogen activator inhibitor type 1 (PAI-1). For example, PAI-1 levels are elevated in young survivors of myocardial infarction (Hamsten, 1985) and a diurnal variation in PAI-1 levels corresponds to the diurnal pattern of myocardial infarction (Krishnamurti et al., 1992). In addition, PAI-1 mRNA levels are elevated in atherosclerotic arteries (Schneiderman, 1992), and PAI-1 levels in plasma are positively correlated with the risk of recurrent myocardial infarction (Hamsten, et al., 1987).

Normal hemostasis in humans depends on the delicate balance between coagulation and fibrinolysis. Accordingly, any imbalance in this system either towards a hypercoagulable condition or a hypofibrinolytic state may result in the development of thrombotic vascular disease. Current interventions for pathological thrombosis rely primarily on thrombolytic therapies or on direct physical ablation of the offending thrombus, by angioplasty or other surgical techniques. These regimens are then generally followed by administration of potent anticoagulants in order to maintain vessel patency. While such treatments have a high degree of effectiveness in removing the original blockage they do carry a significant risk of bleeding complications. Furthermore, approximately 40% of patients receiving thrombolytic therapy do not attain optimal reperfusion (Lincoff et al., 1993). In addition, 25% to 55% of patients undergoing angioplasty suffer from significant restenosis within six months (Cercek et al., 1991). Therefore, the development of additional treatment strategies, directed at enhancing fibrinolysis, may be effective in patients that do not currently respond to thrombolytics. Such a adjuvant therapy might also permit a reduction in anticoagulant therapy in all patients, lessening the potential risk of bleeding complications.

In vivo, natural thrombolysis is an orderly process that develops temporally through activation of the fibrinolytic system. The common end point of this pathway is conversion of the zymogen plasminogen into the trypsin-like protease plasmin, a proteolytic enzyme which through a series of specific cleavages systematically degrades fibrin into soluble fibrin degradation products, resulting in timely blood clot dissolution. The primary activators of plasminogen in vivo are the serine proteases, urokinase (uPA) and tissue plasminogen activator (tPA), with the latter being the major physiologic activator of plasminogen in plasma (Wallén, 1980; Saksela, 1988). In addition to the regulation of vascular fibrinolysis (Bachmann et al., 1987), these enzymes are also thought to critically influence many other biological processes including ovulation (Hsueh et al., 1988; Ohlsson et al., 1991), inflammation (Pöllänen et al., 1991), tumor metastasis (Dano et al., 1985), angiogenesis (Moscatelli et al., 1988), and tissue remodeling (Saksela, 1988), and smooth muscle cell proliferation (Grainger et al., 1993).

The regulation of fibrinolysis is a complex process that is controlled on many levels. The synthesis and release of PAs is governed by various hormones, growth factors, and cytokines (Saksela, 1988; Dano et al., 1985). Following secretion, PA activity can be regulated both positively and negatively by a number of specific protein:protein interactions. Activity can be enhanced or concentrated by interactions with fibrin (Hoylaerts et al., 1982), the uPA receptor (Ellis et al., 1991), the tPA receptor (Hajjar et al., 1990) or the plasminogen receptor (Plow et al., 1991). In contrast, PA activity can be down-regulated by the presence of specific PA-inhibitors (PAIs) Kruithof, 1988; Hart, 1988) or by direct plasmin inhibition (Aoki, 1989). The overall activity of the fibrinolytic system is determined by the interactions among these various elements, and the balance between the opposing activities of enzymes and inhibitors.

Inhibition of thrombin is critical during and after thrombolytic therapy in order to prevent additional fibrin formation and platelet activation at the site of plaque rupture. Heparin, a cofactor for antithrombin III, is the primary agent used to inhibit thrombin in patients with acute coronary syndromes. For t-PA, the co-administration of intravenous heparin appears to be of particular importance in maintaining vessel patency, as evidenced by three recent randomized trials (Lincoff et al., 1993). Conversely, the thrombolytic efficacy of streptokinase is not significantly affected by heparin (GISSI 2 Investigators, 1990). This difference between t-PA and streptokinase is probably explained by several factors, including the shorter half-life of t-PA, its fibrin specificity, and the systemic fibrin(ogen)olytic state generated by streptokinase.

Coronary patency rates of as high as 85% at 90 minutes have been achieved with recent accelerated dosing regimens of t-PA, suggesting that there exists little room for improvement in thrombolytic therapy. However, this seemingly excellent rate of repeffusion belies several limitations that greatly hinder the effectiveness of current thrombolytic strategies (Lincoff et al., 1993). First, patency at 60 minutes, instead of 90 minutes, is the optimal goal in acute MI, since reductions in mortality are as great as 50% in patients treated during the first hour of infarction, but tail-off rapidly thereafter. Secondly, recent studies suggest that only those individuals who attain complete reperfusion—i.e., the restoration of rapid (TIMI grade 3) coronary flow—derive significant reductions in infarct size and mortality from lytic therapy. Yet, only 57% of patients attain TIMI 3 flow after receiving lytic agents. And finally, the significant incidence of reocclusion following initially successful thrombolysis (10–15%) results in a further reduction in the estimated number of patients who receive "optimal" thrombolysis, which has been estimated by Lincoff and Topol to be as low as 25% of patients (Lincoff et al., 1993). Hence, new strategies that result in faster, more complete, and sustained reperfusion are necessary.

It is not known why some patients attain rapid reperfusion following the initiation of thrombolytic therapy, whereas other patients exhibit delayed or incomplete reperfusion, and others no reperfusion. These clinical observations suggest the presence of an intrinsic resistance to thrombolysis that can vary substantially between patients. The mechanisms underlying thrombolysis resistance are poorly understood, and probably differ significantly depending on which plasminogen activator is administered. In the case of t-PA, local factors mediated by platelet activation appear to play a dominant role in determining thrombolytic efficacy. In the case of streptokinase, thrombolysis resistance may be a systemic phenomenon—i.e., mediated by anti-streptokinase antibodies that can inactivate streptokinase before it reaches the target thrombus.

Histologic and angioscopic examination of coronary thrombi reveals that they are frequently platelet-rich (Warnes et al., 1984). Jang et al. have demonstrated that platelet-rich arterial thrombi in rabbits are much more resistant to lysis by t-PA than erythrocyte-rich thrombi, even when t-PA is administered in pharmacologic concentrations (Jang et al., 1989). Among several possibilities, release of platelet plasminogen activator inhibitor-1 (PAI-1) and platelet-mediated clot retraction appear to be the dominant mechanisms underlying platelet-mediated clot lysis resistance in vitro (Levi et al., 1992, Kunitada et al., 1992).

PAI-1, a member of the serpin superfamily of protease inhibitors, is a fast-acting and specific inhibitor of t-PA (Loskutoff, 1989). PAI-1 is secreted by endothelial cells, and is normally present in plasma in trace amounts (Loskutoff, 1989). Human platelets contain approximately 4000 molecules of PAI-1 per cell (Sprengers et al., 1986), the majority of which exists in an inactive, or latent, form (Booth et al., 1988). Latent PAI-1 can be activated in vitro, and possibly in vivo (Vaughan et al., 1990). The sequence of PAI-1 including the leader sequence is disclosed in SEQ ID NO:7.

Monoclonal antibodies to PAI-1 markedly diminish the capacity of platelets to inhibit t-PA-mediated fibrinolysis in vitro, suggesting that sufficient active PAI-1 is present in platelet-rich clots to inhibit t-PA, and that PAI-1 is the dominant factor underlying platelet-mediated clot lysis resistance (Levi et al., 1992; Braaten et al., 1993). However, Kunitada et al. found no significant PAI-1 effect in a clot lysis system in which platelets inhibited thrombolysis initiated by pharmacologic concentrations of t-PA (Kunitada et al., 1992). These authors concluded that platelets inhibit clot lysis not via PAI-1, but rather as a consequence of clot retraction.

These discordant results may be explained by the different experimental conditions employed in these studies, since the magnitude of a PAI-1 effect observed in vitro is critically dependent upon the concentrations of t-PA and platelets. These concentrations may differ substantially between different experimental systems, and also may differ markedly from the concentrations of PAI-1, platelets, and t-PA that are attained at sites of clot formation in vivo. Whereas in vitro clot lysis assays typically employ a platelet concentration of $10^8$–$10^9$/mL (Levi et al., 1992), histologic evaluation of platelet-rich coronary thrombi reveals that they consist, to a substantial degree, of solid masses of platelets (Warnes, 1984). Within this environment, the calculated concentration of platelets exceeds $10^{11}$/mL. Hence, a more definitive assessment of the impact of PAI-1 vs. clot retraction on the lysis of platelet-rich clots requires the analysis of thrombi formed in vivo under conditions that mimic pathologic states, such as myocardial infarction. However, such studies have not been performed.

As previously discussed, the thrombolytic efficiency of t-PA is enhanced by co-administration of heparin (Lincoff et al., 1993). A resistance to prolongation of the activated partial thromboplastin time (APTT) is observed in some patients with acute ischemic syndromes, which may indirectly impede thrombolytic therapy (Maraganore et al., 1992; Hsia et al., 1992). However, the etiology, prevalence, and magnitude of systemic heparin resistance in the setting of acute coronary artery disease are unknown.

Localized heparin resistance at sims of arterial injury also occurs, and may be of greater clinical significance than systemic heparin resistance. Localized heparin resistance has been attributed to the capacity of thrombin to bind fibrin, since in vitro studies indicate that the heparin/antithrombin III complex is a poor inhibitor of clot-bound thrombin, compared to hirudin, a direct-acting thrombin inhibitor (Weitz et al., 1990). However, platelets contain several factors that inhibit heparin, such as heparatinase, platelet factor 4, and histidine-rich glycoprotein (Rucinski et al., 1983).

The accumulation of these factors within platelet-rich thrombi may also locally inhibit heparin efficacy, particularly under states of impaired coronary flow. To data, the relative impact of fibrin vs. platelet factors on heparin function in vivo has not been defined. Nevertheless, it is clear that platelet-rich thrombus formation is a thrombin-dependent phenomenon, since inhibition of thrombin formation at sites of arterial injury substantially reduces platelet deposition (Sitko et al., 1992).

In contrast to t-PA, successful thrombolysis by streptokinase (SK) is strongly associated with the attainment of a systemic lytic state, which generally is defined by a significant (e.g.>20%) reduction in plasma fibrinogen and plasminogen (Rothbard et al., 1985). However, a significant portion of patients do not achieve a lytic state after receiving SK.

Streptokinase is highly immunogenic, and pre-existing anti-SK antibodies due to prior Streptococcal infection could prevent induction of a lytic state. Two studies as well as several case reports suggest that naturally occurring anti-SK antibodies can cause thrombolysis resistance (Lew et al., 1984; Hoffmann et al., 1988; Brugemann et al., 1993). However, another study indicates that pre-existing anti-SK IgG titers are not related to successful coronary thrombolysis (Fears et al., 1992), and the correlation between anti-SK IgG titers and streptokinase resistance in vitro is poor (Moran et al., 1984).

It is likely that several factors have prevented an adequate assessment of the anti-therapeutic impact of SK antibodies. First, the assays used in prior studies are relatively crude. For example, an anti-IgG titer does not discern between inhibitory vs. non-inhibitory antibodies. Similarly, the assay most commonly used for defining SK-resistance (i.e., identification of the maximal SK dilution factor that results in whole blood clot lysis within 10 min) is not independent of other inhibitors of fibrinolysis, such as α2-antiplasmin and PAI-1, which can vary substantially between patients. And finally, the clinical variable with which antibody titers are usually correlated (i.e., angiographically-documented arterial patency) suffers from several limitations. For example, this "snapshot" definition of successful thrombolysis (usually obtained 90–180 min after initiating therapy), does not differentiate between two patients who reperfused at 30 min and 80 min, respectively; yet their clinical benefit would probably differ significantly.

It is likely that a more refined analysis of the human immune response to streptokinase will yield information with important therapeutic implications. For example, clearance of SK from the circulation is probably highly dependent upon antibody-antigen interactions. Yet, very little is known about which regions of the SK molecule represent the dominant epitopes for antibody production in humans (Reed et al., 1993). Such information is also highly relevant to the readministration of SK to the significant number of patients who sustain a second myocardial infarction. Several studies suggest that anti-SK Ab titers sufficient to neutralize most or all of a standard SK dose (1.5 million units) can persist for as long as 1 year after receiving SK (Jalihal et al., 1990). Consequently, readministration of SK is not recommended for at least 1 year after receiving this agent. An identification of dominant SK epitopes might also allow the design of recombinant SK molecules with reduced immunogenicity (Marder, 1993), which could have considerable clinical impact.

During the last ten years the recognition of PAIs as critical regulators of the fibrinolytic system has gained broad acceptance. PAI-1, formerly called the endothelial cell PAI, or the fast acting plasma PAI, is thought to be one of the principal regulators of vascular fibrinolysis. It is a single chain glycoprotein with a molecular weight of 50 kDa (van Mourik et al., 1984) and is the most efficient inhibitor known of the single- and two-chain forms of tPA and of uPA, with second order rate constants ranging between 0.5 and $2.7 \times 10^7 M^{-1} s^{-1}$ (Lawrence et al., 1989).

PAI-1 is present in platelets and many other tissues and is produced by many cells in culture (Erickson et al., 1984; Sawdey et al., 1991; Krishnamurti et al., 1992). In vivo the primary extravascular source of PAI-1 appears to be vascular smooth muscle cells (Loskutoff, 1991). However, in response to endotoxemia or other pathological conditions, endothelial cells become a major site of PAI-1 synthesis (Pyke et al., 1991; Schneiderman et al., 1992; Keeton et al., 1993). In plasma PAI-1 is present as a complex with vitronectin or S protein (Wiman et al., 1984; Declerck et al., 1988; Wiman et al., 1988). PAI-1 is also associated with vitronectin in the extracellular matrix in culture, and may be involved in maintaining the integrity of the cell substratum in vivo (Mimuro et al., 1987; Knudsen et al., 1987; Mimuro et al., 1989). PAI-1 also binds to fibrin, but with a lower affinity (Braaten et al., 1993; Wagner et al., 1989; Keijer et al., 1991; Reilly et al., 1991, Reilly et al., 1992). The major source of plasma PAI-1 is not known but is likely to be the vascular smooth muscle cells. However, a contribution from the platelet pool cannot be excluded. PAI-1 functions efficiently in solution as well as when bound to surfaces and it is likely that it regulates fibrinolysis in both environments.

The cDNA for human PAI-1 was isolated in 1986. The single PAI-1 gene is composed of 9 exons spanning approximately 12 kb (Follo et al., 1989; Strandberg et al., 1988) and is a member of the serine protease inhibitor (serpin) super gene family (Huber et al., 1989; Carrell et al., 1986). Serpins are thought to inhibit their target proteases via a common mechanism that results in the generation of an equimolar, sodium dodecyl sulfate (SDS)-stable complex (Carrell et al., 1986). Though individual inhibitors generally demonstrate remarkable protease specificity, overall the reported serpin structures are strikingly similar (Huber et al., 1989; Stein et al., 1990; Loebermann et al., 1984; Mottonen et al., 1992).

In native serpins the reactive center loop appears to be exposed on the surface of the molecule in a position where it can interact with its target protease (Schreuder et al., 1994; Carrell et al., 1994). A model of serpin function suggests that active serpins have mobile reactive center loops that can partially insert into β-sheet A (Carrell et al., 1991; Carrell et al., 1992). Partial insertion results in the observed thermal instability of serpins but is necessary for function. Further insertion yields a latent inhibitor that is no longer reactive with the protease but has an increased thermal stability (Mottonen et al., 1992). Evidence for this model has come from studies where synthetic peptides, homologous to the reactive center loops of α1AT and antithrombin III, when added in trans, incorporate into their respective molecules, presumably as a central strand of β-sheet A. This leads to an increase in thermal stability similar to that observed following cleavage of a serpin at its reactive center (Carrell et al., 1991; Schulze et al., 1990). The structural change also converts the serpin from an inhibitor to a substrate for its target protease (Björk et al., 1992; Björk, 1992; Schulze et al., 1991).

While most serpins are able to adopt different conformations, PAI-1 appears uniquely labile and in vivo exist in at least two distinct conformations, active and latent (Lawrence, 1989; Loskutoff et al., 1989). Active PAI-1 decays to the latent form with a half-life of approximately 1 hour at 37° C. With exposure to denaturants (guanidine HCl or SDS), latent PAI-1 can be returned partially to the active form. Though recent X-ray crystallographic findings suggest a structural basis for these two conformations (Mottonen et al., 1992; Carrell et al., 1991), their biologic significance remains unknown.

Vitronectin, an adhesive glycoprotein present in plasma, platelets, and the extracellular matrix, binds active PAI-1 and appears to stabilize it in the active conformation (Declerck et al., 1988). The reaction of PAI-1/vitronectin complexes with either tPA or urokinase results in the dissociation of PAI-1 from vitronectin and the formation of PAI-1-PA complex. Negatively-charged phospholipids can convert latent PAI-1 to the active form, suggesting that cell surfaces may modulate PAI-1 activity (Lambers et al., 1987). The observation that latent PAI-1 infused into rabbits is apparently converted to the active form is consistent with this hypothesis (Vaughan et al., 1990). Kinetic and other evidence has also been presented for a second site of interaction between PAI-1 and tPA, outside of the PAI-1 reactive center (Chmielewska et al., 1988; Lawrence, 1990; Hekman, 1988). The precise localization for these various binding interactions remain unknown. Marked sensitivity of PAI-1 to inactivation by oxidants has been demonstrated, apparently involving a conformational change in PAI-1 upon oxidation of a critical Met residue (Strandberg et al., 1991; Lawrence et al., 1986). A similar sensitivity to oxidation has also been observed for other protease inhibitors and may represent a common mechanism for regulation of serpin activity in vivo, both in health and disease.

Vitronectin is a major protein component of plasma and is also found in many tissues. Synthesis is predominant in the liver, though platelets and monocytes also contain detectable protein. Deficiency of vitronectin has not been reported. Though vitronectin appears to serve an important function in cell adhesion, regulation of complement activation, and thrombosis, its precise function in vivo remains unknown (Tomasini et al., 1991).

The interaction of PAI-1 with vitronectin has generated considerable debate. In one study only active PAI-1 was shown to bind vitronectin (Sigurdardóttir et al., 1990).

However in another study no apparent difference in the binding was seen between active and latent PAI-1 (Kost et al., 1992). The reported dissociation constant is also controversial, with one group reporting a Kd of 0.3 nM for active PAI-1 and vitronectin (Seiffert et al., 1991), while another reports a major dissociation constant of 55–190 nM with a second, low capacity but high affinity binding site (Kd<0.1 nM) (Salonen et al., 1989). Additional controversy surrounds the vitronectin binding site for PAI-1. One report, utilizing ligand blotting of vitronectin cyanogen bromide fragments, localizes the binding site to the somatomedin B domain at the N-terminus of vitronectin (Seiffert et al., 1991). In contrast a second study, using monoclonal antibodies, localizes the PAI-1 binding site to the C-terminus of vitronectin, between residues 348 and 370 (Kost et al., 1992). Some of these conflicting results may be explained by the interaction of both the active and latent forms of PAI-1 with vitronectin, but with markedly different affinities, along with differences in the relative composition of PAI-1 conformers present in alternative PAI-1 preparations. The vitronectin binding domain within PAI-1 is localized to a region near the N-terminus and includes portions of 60-helices C and E and β-strand 1A (Lawrence et al., 1994).

In addition to stabilizing active PAI-1, vitronectin has been shown to alter its specificity, converting it to an efficient inhibitor of thrombin (Ehrlich et al., 1990; Keijer et al., 1991). Vitronectin-bound PAI-1 has a 200-fold greater second order rate constant toward thrombin than does free PAI-1. However this increase depends upon the source of vitronectin used. While all forms of vitronectin appear to bind PAI-1, only vitronectin isolated under physiological conditions is able to stimulate PAI-1 inhibition of thrombin (Naski et al., 1993). Vitronectin has also been shown to stimulate the inhibition of tPA by PAI-1, but to a much less dramatic extent (Keijer et al., 1991; Edelberg et al., 1991). In other studies, reactive center mutants of PAI-1 that have greatly reduced activity toward tPA were shown to have their activity partially restored in the presence of vitronectin (Keijer et al., 1991).

As noted, PAI-1 is thought to play a major regulatory role in a variety of biologic processes (Vassalli et al., 1991). Overexpression of PAI-1 may confer increased risk for thromboembolic disease and elevated PAI-1 levels have been associated with premature myocardial infarction (Krishnamurti et al., 1992; Hamsten et al., 1985). Increased levels of PAI-1 gene expression have recently been observed in atherosclerotic human arteries, suggesting a role for PAI-1 in the pathogenesis of atherosclerosis (Schneiderman et al., 1992).

PAI-1 may also play a major role in the clinical response to thrombolytic therapy with tPA. A number of investigators have identified two classes of thrombi, distinguished by the relative presence or absence of large numbers of platelets. Plateletrich thrombi have been observed to be particularly resistant to lysis by therapeutic thrombolytic agents in several animal models, as well as in humans (Krishnamurti et al., 1992; Jang et al., 1989). Recently, Levi, et al. (Levi et al., 1992) reported complete neutralization of platelet-dependent thrombolysis resistance in a rabbit model, using an anti-PAI-1 monoclonal antibody. In addition, Fay, (Fay et al., 1994) demonstrated that platelet rich clots deficient in PAI-1 were significantly more susceptible to tPA induced lysis than clots containing normal platelets, suggesting that PAI-1 is the major factor responsible for the resistance of platelet-rich thrombi to lysis, and lending further support to the notion that inhibition of PAI-1 activity might be a useful strategy for increasing the efficacy of thrombolytic therapy. Furthermore, inhibition of PAI-1 most likely is a safer form of treatment than administration of exogenous tPA.

As discussed, currently a very common treatment for thrombosis is the administration of tPA. While administration of tPA is effective in the short-term, for example in the treatment of acute coronary syndromes such as myocardial infarction, thrombolytic therapy is unsuccessful in approximately 20% of patients. Furthermore, coronary reocclusion following thrombolytic therapy is not uncommon. In many of these cases, tPA treatment is frustrated by the interference of endogenous PAI-1. This is especially true where there are a high level of PAI-1 rich platelets in the blood clots.

Another problem with therapy with tPA or other lytic agents such as urokinase plasminogen activator (uPA) or streptokinase, is that such agents can be administered only for short periods of time. That is because more prolonged therapy is associated with major hemorrhagic complications. Clearly, a safer and more effective treatment for thrombosis and cardiovascular disease is needed.

Fibrinolysis can be enhanced not only by administering exogenous clot dissolving agents such as tPA but also by inactivating PAI-1. In addition, thromboembolytic therapy with exogenous tPA, uPA, or streptokinase can be enhanced if supplemented with a synthetic PAI-1 inhibitor. Furthermore, the administration of a PAI-1 inhibitor to patients, is safer than the administration of excess lytic agents. Patients who have been identified with a complete deficiency of PAI-1 suffer from only a mild to moderate bleeding disorder (Diéval et al., 1991; Schleef et al., 1989; Lee et al., 1993, Fay et al., 1992). Thus, mild partial deficiency, induced by a PAI-1 inhibitory drug most likely represents a very safe, long-term, chronic treatment which may be of major benefit by reducing cardiovascular risk.

SUMMARY OF THE INVENTION

The present invention provides novel peptides capable of inactivating plasminogen activator inhibitor-1 (PAI-1). These peptides inactivate PAI-1 by facilitating the conversion of PAI-1 from its active to its inactive state and thus render PAI-1 incapable of complexing with its target proteases, tissue plasminogen activator (tPA) and urokinase plasminogen activator (uPA). These two proteases, tPA and uPA are actively involved in the dissolution of blood clots. Preferred peptides which inactivate PAI-1 include TVASSSTAVIVSAR (SEQ ID NO:1), TVASSSTA (SEQ ID NO:2), TEASSSTA (SEQ ID NO:3), TEAAAATG (SEQ ID NO:4), TEAAAATGAAATGR (SEQ ID NO:5). In another embodiment, preferred peptides further have a length of approximately 8 to 50 amino acids, most preferably having a length of between 8 and 20 amino acids. The peptides of the present invention can be modified by well known techniques. Peptides modified by such well known techniques are within the scope the present invention. In particular, peptides which are acetylated at the amino terminus or activated at the carboxy terminus are preferred.

The invention further provides a method of inactivating PAI-1 in vitro and in vivo by decreasing the half-life of its active state conformation. The method comprises exposing plasminogen activator inhibitor-1 to an effective amount of a peptide with an amino acid sequence in accordance with SEQ ID NO:1–5. In plasma, PAI-1 appears in both an active and inactive conformation. The protein naturally converts from its active to its inactive form in approximately 98 minutes. The half-life is the amount of time required for PAI-1 activity initially present to decrease by half. The decrease in PAI-1 activity can be accomplished by at least 4 mechanisms: conversion from an active form to an inactive form; conversion of PAI-1 to a non-inhibitory substrate for plasminogen activators; a decrease in the affinity of PAI-1 for plasminogen activators; and clearance of PAI-1 from plasma. While the primary mechanism for decreasing the half life of PAI-1 by a peptide of the present invention is likely to be conversion of PAI-1 from an active form to an inactive form, other mechanisms for decreasing the half life may play a role.

The novel peptides of this invention facilitate such a conversion in less time, i.e. the half-life of plasminogen activator inhibitor-1 is decreased. As discussed in further detail in example 2 below, exposing PAI-1 to an effective amount of TVASSSTAVIVSAR (SEQ ID NO:1) decreases the half-life of PAI-1 to approximately four minutes. The decreases of the half-life of PAI-1 upon exposure to the peptides of SEQ ID NO:2–5 are described in the table in example 2 below.

In another aspect, the present invention provides a method of decreasing the half-life of plasminogen activator inhibitor-1 in the presence of vitronectin. Vitronectin stabilizes the active form of PAI-1 by binding to the inhibitor. The method comprises exposing plasminogen activator inhibitor-1 in the presence of vitronectin to an effective amount of a peptide with an amino acid sequence in accordance with SEQ ID NO:1–5. An effective amount of peptide is that amount which can decrease the half-life of active PAI-1 to between about 1 and 190 minutes when PAI-1 is in the presence of vitronectin. As discussed in examples below, the peptide of SEQ ID NO:1 can decreases the half-life of active state PAI-1 in the presence of vitronectin from approximately 190 to about 120 minutes, a decrease of nearly 40%.

Yet another aspect of the present invention provides a method of promoting clot lysis by decreasing the half-life of plasminogen activator inhibitor-1. The method comprises exposing a clot to an effective amount of a peptide in accordance with SEQ ID NO:1–5. As stated, tPA and uPA are actively involved in clot lysis. Thus, inactivation of these proteins by PAI-1 inhibits clot lysis. This invention provides a method of promoting clot lysis by facilitating the conversion of PAI-1 to its inactive state and thus prevents its binding to and inactivation of the clot dissolving proteins tPA and uPA. The effective amount of peptide is the amount necessary to decrease the in vivo half-life of active PAI-1 to between about 1 and 98 minutes.

In another aspect, a method of promoting clot lysis in the presence of vitronectin is provided. Vitronectin stabilizes PAI-1 in its active conformation. The novel peptides of this invention promotes clot lysis despite the presence of vitronectin by decreasing the half-life of PAI-1. The half-life of PAI-1 in the presence of vitronectin is decreased to between about 1 minute and about 190 minutes. Preferably, the half-life is any time value between 1 minute and 190 minutes.

In a further aspect, the present invention provides a method of promoting lysis of platelet rich clots by exposing the platelet rich clot to an effective amount of a peptide as disclosed herein. Platelet rich clots are difficult to lyse because of the presence of high concentrations of both vitronectin and PAI-1 in platelets. The effective amount of a peptide of the present invention decreases in vitro the half-life of PAI-1 in platelet rich clots to between about 1 minute to about 190 minutes.

Another aspect of this invention provides a method for promoting clot lysis in an animal by combining a therapeutically effective amount of a peptide that inactivates PAI-1 with a carrier to form a pharmaceutical composition and introducing the pharmaceutical composition into the blood stream of the animal. An effective amount of peptide is that amount sufficient to promote clot lysis by decreasing the half-life of plasminogen activator inhibitor-1. The effective amount of peptide to that amount necessary to decrease the in vitro half-life of active PAI-1 to between about 1 and 98 minutes. A preferred animal is a human.

Due to precautions that are necessarily attendant to every new pharmaceutical, the PAI-1 inhibitor peptides, analogues and compositions of the present invention have not been tested as yet in a clinical setting in human subjects. However, the in vitro activity of SEQ ID NO:1–5 as shown in example 2 below demonstrates the utility of the present invention as a clot lysis agent.

Suitable pharmacological carriers include excipients for parenteral administration and/or for oral administration, including solvents, dispersion media, coatings, antibacterial and antifungal agents, isotonic and absorption delaying agents and the like. Pharmacologically acceptable carriers are known and described in *Remington's Pharmaceutical Sciences*, 16th ed., 1980, Mack Publishing Co., incorporated herein by reference.

In another aspect, pharmaceutical compositions suitable for the treatment and prevention of cardiovascular disease, thrombosis, and stroke is provided. Treatment of these diseases is accomplished by administering a therapeutically effective amount of the peptide in a pharmaceutical composition as described above.

Another aspect of this invention is a method of decreasing the risk of coronary heart disease, stroke, and thrombosis and preventing the reocclusion of arteries following clot lysis. Such can be accomplished by treating patients suffering from such diseases with the pharmacological composition of this invention. Such a composition contains therapeutically effective amounts of the PAI-1 inhibitor peptides. In addition, treatment of patients with tPA, uPA or streptokinase can be enhanced by administering the peptides of this invention along with that treatment.

Finally, a preferred aspect of this invention is an assay for detecting PAI-1 activity in a sample by exposing said sample to a plasminogen activator and a peptide in accordance with this invention and detecting plasminogen activator activity.

BRIEF DESCRIPTION OF THE DRAWINGS

FIG. 1 shows the amino acid sequences of SEQ ID NO:1–5. The residue numbers of mature PAI-1 are also indicated.

FIG. 6 in two panels shows clot lysis of a fibrin clot and a platelet rich clot.

FIG. 7 in two panels shows the inhibitory effects of PAI-1 on clot lysis.

FIG. 8 in two panels shows plasminogen activator inhibitor-1 activity upon exposure to a peptide of SEQ ID NO:1.

FIG. 9 in two panels shows the effect of indicated substances on the activated partial thromboplastin time (APTT) and heparin neutralizing activity.

Figure 2:
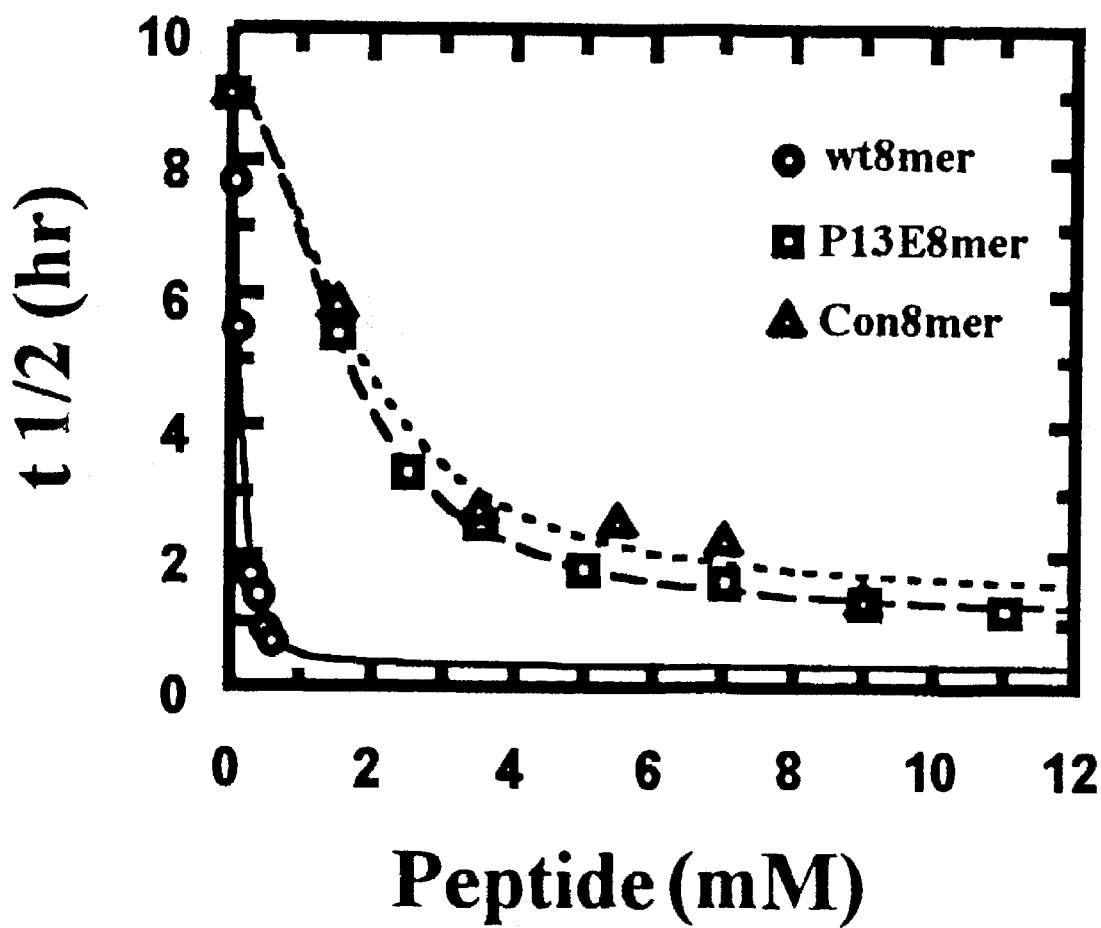
FIG. 2 shows dose response curves for peptides of SEQ ID NOS: 2–4. PAI-1 (6.4 µM) was incubated with increasing concentrations of each peptide at 23° C. and the ($T_{1/2}$) of PAI-1 inactivation was determined by measuring the PAI-1 activity remaining over time.

Peptides may also by prepared by recombinant means, and the "recombinant" peptide obtained from recombinant host cells which express the peptide. To achieve this, a specific oligonucleotide based upon the sequence of the desired peptide, as is known to those of skill in the art and described herein is prepared. The oligonucleotide is then inserted into an expression vector, such as any one of the many expression vectors currently available commercially. A prokaryotic or eukaryotic host cell is then transformed with the vector, where it will direct the expression of the so-called recombinant version of the peptide, which may then be purified from the recombinant host cell. The preparation of oligonucleotide, vector and transformation of the host cell are within the skill of the ordinary artisan.

To prepare a specific oligonucleotide using the sequence of the desired peptide one may use the following table that lists the appropriate codons corresponding to each of the amino acids.

| AMINO ACIDS | | | CODONS | | | | |
|---|---|---|---|---|---|---|---|
| Alanine | Ala | A | GCA | GCC | GCG | GCU | |
| Cysteine | Cys | C | UGC | UGU | | | |
| Aspartic acid | Asp | D | GAC | GAU | | | |
| Glutamic acid | Glu | E | GAA | GAG | | | |
| Phenylalanine | Phe | F | UUC | UUU | | | |
| Glycine | Gly | G | GGA | GGC | GGG | GGU | |
| Histidine | His | H | CAC | CAU | | | |
| Isoleucine | Ile | I | AUA | AUC | AUU | | |
| Lysine | Lys | K | AAA | AAG | | | |
| Leucine | Leu | L | UUA | UUG | CUA | CUC | CUG | CUU |
| Methionine | Met | M | AUG | | | | |
| Asparagine | Asn | N | AAC | AAU | | | |
| Proline | Pro | P | CCA | CCC | CCG | CCU | |
| Glutamine | Gln | Q | CAA | CAG | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | |
| Valine | Val | V | GUA | GUC | GUG | GUU | |
| Tryptophan | Trp | W | UGG | | | | |
| Tyrosine | Tyr | Y | UAC | UAU | | | |

DETAILED DESCRIPTION OF THE INVENTION

The present provides a peptide having an amino acid sequence in accordance with SEQ ID NO:1, SEQ ID NO:2, SEQ ID NO:3, SEQ ID NO:4, or SEQ ID NO:5. Wherein the amino terminus of the peptides is an amino terminal threonine. The peptides provided herein are useful in decreasing the half-life of plasminogen activator inhibitor-1 (PAI-1). As discussed herein, decreasing the half-life of plasminogen activator inhibitor-1 promotes fibrinolysis and clot lysis.

Peptides may be prepared by synthetic or recombinant means. The preferred method for preparing peptides in accordance with the present invention is contemplated to be via automated peptide synthesis. A synthetic peptide may be straightforwardly prepared using an automated peptide synthesizer, the operation of which will be generally known to those of skill in the art. Alternatively, peptides in accordance with the invention may be purified from a natural source, such as, for example, residues 356–369 of mature plasminogen activator inhibitor-1.

Peptides may be designed, or engineered, to include multiple copies of the sequences of the present invention. Alternatively, other elements, for example, those designed to impart targeting functions to the peptide may be included, as may elements designed to enhance peptide stability.

It is further contemplated that any peptide of the present invention may be modified to render it biologically protected. As is generally known in the art, biologically protected peptides have certain advantages over unprotected, i.e., unmodified, peptides when administered to human subjects. As disclosed in U.S. Pat. No. 5,028,592, incorporated herein by reference, a peptide which is protected, for example, through acylation of the amino terminus and/or amidation of the carboxyl terminus often exhibits an increase in pharmacological activity. Modification of peptides also provides increased solubility in aqueous media. Other modifications contemplated include methylation of the peptide backbone, substitution of D-amino acids for the naturally occurring L-amino acids, substitution of amino acids with non-natural amino acids, non-peptide analogs, and isoteric compounds.

Bioactive peptides which contain an acetyl or amido group bound to the N-terminus and/or an amido function bound to the C-terminus have been found to maintain biological activity, but to be less susceptible to acid hydrolysis. This is believed to be due, in part, to the protecting groups playing a role in reducing the susceptibility of the protected peptide to enzymatic attack and degradation. Thus all biologically protected or modified peptides are intended to fall within the scope of the present invention.

Preferred peptides include those with a sequence in accordance with the peptide sequences TVASSSTAVIVSAR (SEQ ID NO:1), TVASSSTA (SEQ ID NO:2), TEASSSTA (SEQ ID NO:3), TEAAAATG (SEQ ID NO:4), TEAAAAT-GAAATGR (SEQ ID NO:5). In another embodiment, preferred peptides further have a length of approximately 8 to 50 amino acids, most preferably having a length of between 8 and 10 amino acids. As discussed in example 2 below, all of these peptides decreased the half-life of plasminogen activator inhibitor-1. In another preferred embodiment, the amino terminus of the peptides identified as SEQ ID NO:1-5 are acetylated.

Modifications and changes can be made in the structure of a peptide of the present invention and still obtain a molecule having like inhibitor characteristics. For example, certain amino acids can be substituted for other amino acids in a sequence without appreciable loss of inhibitory activity. Because it is the interactive capacity and nature of a peptide that defines that peptide's biological functional activity, certain amino acid sequence substitutions can be made in a peptide sequence (or, of course, its underlying DNA coding sequence) and nevertheless obtain a peptide with like properties.

In making such changes, the hydropathic index of amino acids can be considered. The importance of the hydropathic amino acid index in conferring interactive biologic function on a peptide is generally understood in the art (Kyte & Doolittle, *J. Mol. Biol.*, 157: 105-132, 1982). It is known that certain amino acids can be substituted for other amino acids having a similar hydropathic index or score and still result in a peptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cystine (+2.5); methionine (+1.9); alanine (+1.8); glycine (-0.4); threonine (-0.7); serine (-0.8); tryptophan (-0.9); tyrosine (-1.3); proline (-1.6); histidine (-3.2); glutamate (-3.5); glutamine (-3.5); aspartate (-3.5); asparagine (-3.5); lysine (-3.9); and arginine (-4.5).

It is understood in the art that the relative hydropathic character of the amino acid determines the secondary structure of the resultant peptide, which in turn defines the interaction of the peptide with other molecules, such as enzymes, substrates, receptors, antibodies, antigens, and the like. It is known in the art that an amino acid can be substituted by another amino acid having a similar hydropathic index and still obtain a functionally equivalent peptide. In such changes, the substitution of amino acids whose hydropathic indices are within ±2 is preferred, those which are within ±1 are particularly preferred, and those within ±0.5 are even more particularly preferred.

Substitution of like amino acids can also be made on the basis of hydrophilicity, particularly where the biological functional equivalent peptide thereby created is intended for use in immunological embodiments. U.S. Pat. No. 4,554,101, incorporated herein by reference, states that the greatest local average hydrophilicity of a peptide, as governed by the hydrophilicity of its adjacent amino acids, correlates with its immunogenicity and antigenicity, i.e. with a biological property of the peptide.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (-0.5±1); threonine (-0.4); alanine (-0.5); histidine (-0.5); cysteine (-1.0); methionine (-1.3); valine (-1.5); leucine (-1.8); isoleucine (-1.8); tyrosine (-2.3); phenylalanine (-2.5); tryptophan (-3.4). It is understood that an amino acid can be substituted for another having a similar hydrophilicity value and still obtain a biologically equivalent, and in particular, an immunologically equivalent peptide. In such changes, the substitution of amino acids whose hydrophilicity values are within ±2 is preferred, those which are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine (See table below). The present invention thus contemplates functional or biological equivalents of a peptide inhibitor of plasminogen activator inhibitor-1 as set forth above.

TABLE

| Original Residue | Exemplary Substitutions |
|---|---|
| Ala | Gly; Ser |
| Arg | Lys |
| Asn | Gln; His |
| Asp | Glu |
| Cys | Ser |
| Gln | Asn |
| Glu | Asp |
| Gly | Ala |
| His | Asn; Gln |
| Ile | Leu; Val |
| Leu | Ile; Val |
| Lys | Arg |
| Met | Met; Leu; Tyr |
| Ser | Thr |
| Thr | Ser |
| Trp | Tyr |
| Tyr | Trp; Phe |
| Val | Ile; Leu |

Biological or functional equivalents of a peptide be prepared by using a peptide synthesizer or through the use of site-specific mutagenesis. Peptide synthesizers are commercially available and the use of these synthesizers are known in the art. Site-specific mutagenesis is a technique useful in the preparation of second generation peptides, or biologically functional equivalent peptides, derived from the sequences thereof, through specific mutagenesis of the underlying DNA. As noted above, such changes can be desirable where amino acid substitutions are desirable. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art, as exemplified by Adelman, et al. (1983). As will be appreciated, the technique typically employs a phage vector which can exist in both a single stranded and double stranded form. Typical vectors useful in site-directed mutagenesis include vectors such as the M13 phage (Messing, et al. 1981). These phage are commercially available and their use is generally known to those of skill in the art.

In another aspect, the present invention provides a method of decreasing the half-life of active plasminogen activator inhibitor-1. The half-life of PAI-1 is decreased by exposing plasminogen activator inhibitor-1 to a peptide having an amino acid sequence in accordance with SEQ ID NO:1–5. The peptides disclosed herein, SEQ ID NO:1–5, can be further used to determine the in vitro concentration of active plasminogen activator inhibitor-1 in a biological sample (e.g. plasma).

Plasminogen activator inhibitor-1 shows two conformations, an active form and a latent (inactive) form. The active form of PAI-1 inhibits the proteases, tissue plasminogen activator (tPA) and urokinase type plasminogen activator (uPA) by forming 1:1 protease-inhibitor complexes. The inhibition of tPA and uPA inhibits fibrinolysis, the dissolution of fibrin clots, by inhibiting the conversion of plasminogen to plasmin. (Fibrinolysis is discussed in greater detail in the background section herein.) The spontaneous conversion of PAI-1 from an active form to the latent form occurs both in vivo and in vitro.

As used herein, half-life is the amount of time required for PAI-1 activity initially present to decrease by half. The decrease in PAI-1 activity can be accomplished by at least 4 mechanisms: conversion from an active form to an inactive form; conversion of PAI-1 to a non-inhibitory substrate for plasminogen activators; a decrease in the affinity of PAI-1 for plasminogen activators; and clearance of PAI-1 from plasma. While the primary mechanism for decreasing the half life of PAI-1 by a peptide of the present invention is likely to be conversion of PAI-1 from an active form to an inactive form, other mechanisms for decreasing the half life may play a role.

The in vitro half-life of active PAI-1 at 37° C. is about 100 minutes. Example 2 shows that the half-life of PAI-1 can be reduced to about 4 minutes by exposing PAI-1 to the 14-mer peptide of SEQ ID NO: 1. This represents a decrease of about 25-fold in the half-life of PAI-1 in the presence of a peptide of SEQ ID NO: 1. The consensus 14-mer TEAAAATGAAATGR (SEQ ID NO:5) decreased the half-life of PAI-1 to 12 minutes. Similarly, the 8-mers, TVASSSTA (SEQ ID NO:2), TEASSSTA (SEQ ID NO:3) and TEAAAATG (SEQ ID NO:4) decreased the half-life of PAI-1 to 43, 72 and 78 minutes, respectively.

The half-lives reported herein were obtained at 37° C. or 25° C. It is well recognized that in general, half-lives decrease as the reaction temperature increases. As detailed in examples 2 and 3 below, the half-life of PAI-1 at 25° C. is about 540 minutes. The time limitations imposed on the reduction of half-lives of the presently claimed invention recite the half-lives obtained between 25° C. and 37° C. However, one of ordinary skill in the art can increase or decrease the observed half-lives by altering the temperature of a reaction. Thus, if the half-life of inactivation of PAI-1 was determined at for example 20° C., the observed half-life would be greater than 540 minutes. Similarly, if the effect of a peptide as disclosed herein on the half-life of PAI-1 were to be determined at 20° C., it would be less than that observed at 20° C. in the absence of that peptide. All such obtained half-lives come within the scope of the presently claimed invention. The scope of the present invention is not limited to the half-lives obtained at temperatures between 25° C. and 37° C. Rather, the half-lives which are encompassed by the present invention include all those half-lives which can be obtained between 0° C. and 100° C.

The effective amount of a peptide of the present invention is that amount sufficient to decrease the half-life of plasminogen activator inhibitor-1. In one embodiment, an effective amount of a peptide decreases in vitro the half-life of PAI-1 to between about 1 and about 98 minutes. In a preferred embodiment, an effective amount of a peptide decreases the half-life of PAI-1 to between about 1 and 10 minutes. In a particularly preferred embodiment, the effective amount of a peptide as disclosed herein reduces the half-life to about 4 minutes.

As discussed herein, vitronectin binds to plasminogen activator inhibitor-1 and slows down the spontaneous inactivation of PAI-1. The peptides of the present invention decrease the half-life of plasminogen activator inhibitor-1 in the presence of vitronectin. In one embodiment, an effective amount of a peptide decreases the in vitro half-life of PAI-1 in the presence, of vitronectin to between about 1 and about 190 minutes. In a preferred embodiment, an effective amount of a peptide decreases the half-life of PAI-1 to between about 110 and 150 minutes in vitro. In a particularly preferred embodiment, the effective amount of a peptide as disclosed herein reduces the in vitro half-life to about 120 minutes.

In another aspect the present invention provides a method of promoting clot lysis. The method comprises exposing the clot to an effective amount of a peptide having the following amino acid sequences: TVASSSTAVIVSAR (SEQ ID NO:1), TVASSSTA (SEQ ID NO:2), TEASSSTA (SEQ ID NO:3), TEAAAATG (SEQ ID NO:4) and TEAAAAT-GAAATGR (SEQ ID NO:5). A preferred peptide has a length of between 8 to 50 amino acids.

The peptide of the present invention promotes clot lysis by inhibiting plasminogen activator inhibitor-1. PAI-1 inhibits clot lysis by inhibiting the conversion of plasminogen to plasmin (e.g. tPA and uPA). Plasmin is the major protease of the fibrinolytic system which digests fibrin into soluble fibrin degradation products thereby degrading the fibrin clot.

The effective amount of a peptide of the present invention to promote clot lysis is that amount sufficient to decrease the half-life of plasminogen activator inhibitor-1. In one embodiment, an effective amount of a peptide decreases in vitro the half-life of PAI-1 to between about 1 and about 98 minutes. In a preferred embodiment, an effective amount of a peptide decreases the in vitro half-life of PAI-1 to between about 1 and 10 minutes. In a particularly preferred embodiment, the effective amount of a peptide as disclosed herein reduces the in vitro half-life to about 4 minutes.

Further, the peptides of the present invention promote clot lysis by decreasing the half-life of plasminogen activator inhibitor-1 in the presence of vitronectin. In one embodiment, an effective amount of a peptide decreases the in vitro half-life of PAI-1 in the presence of vitronectin to between about 1 and about 190 minutes. In a preferred embodiment, an effective amount of a peptide decreases the in vitro half-life of PAI-1 to between about 110 and 150 minutes. In a particularly preferred embodiment, the effective amount of a peptide as disclosed herein reduces the in vitro half-life to about 120 minutes.

Another aspect of the present invention provides a method of promoting lysis of platelet rich clots by exposing the platelet rich clot to an effective amount of a peptide in accordance with SEQ ID NO:1–5. Platelet rich clots are clots with high platelet content and are difficult to lyse because of high concentrations of both vitronectin and PAI-1. An effective amount of a peptide to promote lysis of platelet rich clots is that amount sufficient to decrease the half-life of plasminogen activator inhibitor-1. Because platelet rich clots are high in vitronectin concentration, an effective amount of a peptide decreases the in vitro half-life of PAI-1 in platelet rich clots to between about 1 and about 190 minutes. In a preferred embodiment, an effective amount of a peptide decreases the in vitro half-life of PAI-1 to between about 110 and 150 minutes. In a particularly preferred embodiment, the effective amount of a peptide as disclosed herein reduces the in vitro half-life to about 120 minutes.

A method of therapeutically promoting clot lysis by decreasing the half-life of active plasminogen activator inhibitor-1 is further provided. The method comprises combining a therapeutically effective amount of a peptide in accordance with SEQ ID NO:1–5 with a pharmaceutically acceptable carrier to form a pharmaceutical composition and introducing the pharmaceutical composition into the blood stream of an animal. Preferably, the animal is a human.

A therapeutically effective amount of a peptide, similar to the discussions above, is that amount sufficient to decrease the half-life of active plasminogen activator inhibitor-1. Preferably, in vitro the half-life of PAI-1 is decreased to between about 1 and 190 minutes and any time value between 1 and 98 minutes. It is understood that the amount of peptide necessary to decrease the half-life of PAI-1 in a therapeutic environment (in vivo) versus an in vitro setting can be different. However, the scope of the present invention covers the use of the peptides as disclosed herein in both in vivo and in vitro settings. The amount of peptide sufficient to decrease the half-life of PAI-1 in a therapeutic environment must take into consideration other factors such as solubility of the peptide and how quickly a peptide is cleared from the blood stream (half-life of the peptide). Solubility and in vivo half-life of a peptide as disclosed herein is discussed above. For example, peptides of the present invention can be covalently modified to increase solubility and to increase the in vivo half-life of the peptide. The modifications of a peptide to increase solubility and half-life of the peptide is within the skill of an ordinary artisan. Reagents commonly used to chemically modify peptides is listed on pages 103–105 of *Practical Handbook of Biochemistry and Molecular Biology*, Fasman (ed.), CRC press, 1989.

Due to precautions that are necessarily attendant to every new pharmaceutical, the PAI-1 inhibitor peptides, analogues and compositions of the present invention have not been tested as yet in a clinical setting in human subjects. However, the in vitro activity of SEQ ID NO:1–5 as shown in examples below demonstrates the utility of the present invention as a clot lysis agent. The following embodiments represent the best mode currently contemplated by the present inventors of carrying out the practice of the invention in various clinical settings.

The phrases "pharmaceutically or pharmacologically acceptable" refer to molecular entities and compositions that do not produce an adverse, allergic or other untoward reaction when administered to an animal, or a human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

In addition to the compounds formulated for parenteral administration, such as intravenous or intramuscular injection, other pharmaceutically acceptable forms include, e.g., tablets or other solids for oral administration; time release capsules; and any other form currently used, including cremes, lotions, mouthwashes, inhalants and the like.

The active peptidyl compounds may also be formulated for parenteral administration, e.g., formulated for injection via the intravenous, intramuscular, subcutaneous, or even intraperitoneal routes. The preparation of an aqueous composition that contains a peptide as disclosed herein as an active ingredient will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

Solutions of the inhibitor peptides as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

A PAI-1 inhibitor peptide can be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial ad antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The therapeutic formulations of the invention may also be prepared in forms suitable for topical administration, such as in cremes, lotions and patches. These forms are envisioned to be particularly suitable for long term treatment with inhibitors of plasminogen activator inhibitor-1.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject.

Further aspects of the present invention concern pharmaceutical compositions which comprise a peptide in accordance with the present invention in a pharmaceutically acceptable excipient. These compositions include formulations for parenteral administration, such as for intravenous, intramuscular, subcutaneous and intrapefitoneal administration; inhalants, aerosols and spay formulations; formulations of peptides for topical use, such as in creams, ointments and gels; and liposome-encapsulated peptides.

Formulations for parenteral administration may generally include solutions of the peptide inhibitor in sesame or peanut oil, aqueous propylene glycol, or in sterile aqueous solutions. Such aqueous solutions should be suitably buffered if necessary and the liquid diluent first rendered isotonic with sufficient saline or glucose. The precise compositions and use of such pharmaceutical carriers will generally be known to those of skill in the art in light of the present disclosure. For a detailed listing of suitable pharmaceutical agent/ additives compositions and associated administrative techniques one may wish to refer to Remington's Pharmaceutical Sciences, 16th ed., 1980, Mack Publishing Co., incorporated herein by reference.

For the delivery of the inhibitory peptides to tissue sites it is alsothat liplated that liposome-encapsulated forms may be employed. Such techniques are known to increase the efficacy and significantly prolong the half-life of administered compounds, and particularly, compounds of lower molecular weight such as the peptides disclosed herein. Various techniques for liposome encapsulation exist and will be generally known to those of skill in the art.

Pharmaceutical compositions including peptides in accordance with SEQ ID NO:1–5, analogues or second generation peptides prepared as described above are likely to be useful in the treatment of various thrombolytic diseases, such as coronary heart disease, stroke, thrombosis and reocclusion of arteries following clot lysis. These peptides are particularly suitable for inhibiting plasminogen activator inhibitor-1 and the lysis of clots. Further, the peptides disclosed herein can be used to treat cardiovascular diseases in conjunction with known therapies including administration of tissue type plasminogen activator, urokinase plasminogen activator, streptokinase, heparin and hirudin. The peptides of this invention can also be utilized in an assay for detecting PAI-1 activity in a sample suspected of containing PAI-1 by exposing said sample to plasminogen activator and a peptide in accordance with this invention and detecting plasminogen activator activity.

EXAMPLE 1

CHARACTERIZATION OF PAI-1

Expression of Recombinant Wild-type PAI-1 in *E. coli* and Preparation of Antibody Reagents:

Wild-type human PAI-1 has been expressed (Ny et al., 1986) in both eukaryotic and prokaryotic cells and purification systems for PAI-1 have been developed (Lawrence et al., 1989). Comparison of the PAI-1 proteins from both of these systems to purified natural PAI-1 from the human cell line HT1080 indicates that PAI-1 produced in *E. coli* has biological properties very similar to natural PAI-1 and thus is useful for the study of PAI-1 structure and function. The only significant difference between PAI-1 produced in *E. coli* and natural PAI-1 is that the *E. coli* produced material can be isolated in a predominantly active form. In contrast, natural PAI-1 is primarily latent and requires reactivation. This high level of activity without the need for treatment with denaturants is a major advantage of this approach compared to other published methods (Ehrlich et al., 1990; Shubeita et al., 1990).

In recent studies PAI-1 expression has been switched to the vector pET3a (Studier et al., 1990). Final yields have been significantly improved resulting in isolation of up to 20 mg of PAI-1 per liter of *E. coli* culture. The protein product was >99% homogenous by SDS-PAGE and N-terminal sequence analysis. In addition, purification procedures have been developed to allow isolation of both fully active and fully latent PAI-1. Rabbit antiserum against purified recombinant PAI-1 has been produced and, the resulting antibodies affinity-purified. A specific PAI-1 enzyme-linked immunoabsorbent assay (ELISA) has also been developed (Sherman et al., 1992). In addition, eight monoclonal antibodies directed against recombinant PAI-1 have been isolated. All 8 recognized PAI-1 in solution in a microtiter plate-based assay and 5 reacted strongly with PAI-1 on Western blots.

Construction of PAI-1/Serpin Reactive Center Loop Chimeras:

In addition, a series of serpin chimeras was constructed by removing the region of the PAI-1 cDNA coding for amino acids P17 to P2' of the PAI-1 reactive center and replacing it with the same region from either PAI-2, antithrombin III, or a consensus sequence designed from an alignment of serpin inhibitors (Lawrence et al., 1990). The chimeras were expressed and purified, and analysis of their functional properties demonstrated that the residues of the reactive center loop, apart from the P1 bait residue, are not the primary determinants of inhibitor specificity. These results suggested that sites outside of the reactive center, so called exo-sites, must also play an important role in enzyme recognition. In support of this hypothesis, it was shown that active site blocked tPA could still associate with PAI-1 and be coimmunoprecipitated, whereas similarly treated uPA could not.

Construction and Characterization of a PAI-1 Reactive Center Mutant Library:

A saturation mutagenesis strategy was employed to assess the roles of the P1-P1', Arg-Met residues in determining inhibitor specificity. This method provides a more complete and unbiased view than generally obtained from the study of individually designed mutants (Sherman et al., 1992). In total, 345 mutant PAI-1 clones were sequenced and 177 unique reactive center variants characterized. Thirty-seven of the 177 unique mutants screened were identified as active against uPA, each containing either Arg or Lys at P1. P1Arg-P1'Pro and P1Lys-P1'Pro were the only two P1Arg or Lys variants that were inactive. The remaining 138 unique PAI-1 mutants showed no detectable activity (Sherman et al., 1992).

An unanticipated result was obtained when the library was screened for tPA inhibitory activity. A significant subset of mutants that were inactive toward uPA were able to fully inhibit tPA. These included mutants with P1 Trp, Phe, or Tyr, suggesting that aromatic residues at P1 can yield a tPA-specific inhibitor. Additional site-directed mutants were then constructed, to give every possible amino acid substitution at P1, all in association with the wild-type P1'Met. In addition, mutants were designed in an attempt to increase the relative target specificity of PAI-1 for tPA. One of these mutants, P3Tyr-P2Ser-P1Tyr-P1'Met had a second-order rate constant toward tPA of $2.5 \times 10^6 M^{-1}s^{-1}$, nearly equal to the rate of inhibition for wtPAI-1 toward tPA ($1.0 \times 10^7 M^{-1}s^{-1}$). In contrast, this mutant demonstrated no detectable inhibition toward uPA. While PAI-2 shows a strong preference for uPA over tPA, this is the first tPA specific serpin described, and should prove to be a useful reagent for dissecting the relative contributions of uPA and tPA inhibition in both in vivo and in vitro systems.

Fluorescent PAI-1 as a Probe of Serpin Structure:

Fluorescent PAI-1 was utilized as a probe of serpin structure in a variety of experiments. The PAI-1 reactive center mutant P1'Cys (Sherman et al., 1992) was ligated into the expression vector pET3a for large scale preparation. 1 mM DTT was added to all buffers to maintain cysteine in a reduced form. The free SH group of the P1'Cys was labeled using iodoacetamido-fluorescein, resulting in an active fluorescent PAI-1 (FL-PAI-1). Conversion to latent PAI-1 occurred with approximately the same $t_{1/2}$ as wild-type PAI-1. Stern-Volmer quenching indicated that the reactive-center bond is somewhat less accessible to solvent in the latent conformation. In contrast, KI quenching of the 4 Trp residues of wild-type PAI gave $K_Q$ values which indicated greater accessibility of these residues in the latent conformation.

Additional Cys containing PAI-1 variants were constructed including double mutants with Cys substituted for either P9Ser, P10Ser, Leu269 or Arg271 each coupled with P1'Cys. All four double mutants maintained PAI-1 functional activity. Labeling of each Cys with a different fluorescent probe allows for determination of intramolecular distances in different conformations (active, latent, oxidized, and complexed to tPA) by measuring electronic energy transfer using time resolved fluorescence spectroscopy. Experiments using a double, fluorescein-rhodamine, labeled P9-P1'PAI-1 mutant indicate that in active PAI-1 these two residues must lie less than 20 Ångstrom apart.

Random Mutagenesis of Vitronectin Binding Domain:

Another set of experiments utilized a random mutagenesis to identify critical residues responsible for the interaction between PAI-1 and vitronectin (Lawrence et al., 1994). In these experiments, the entire PAI-1 coding sequence was subjected to random mutagenesis by PCR. The full length mutagenized PCR product was then digested with Sfi1 and BclI and the resulting fragment, spanning nucleotides 245–651 of PAI-1 was cloned into the wild-type PAI-1 pET3a expression vector. In this way, a set of random mutants was created with mutations restricted to the region spanning amino acids 13–146. 190 independent plasmid clones were grown, protein expression induced, and cell lysates prepared directly in microtiter plates. All 190 clones were screened in duplicate for binding to vitronectin-coated microtiter plates and for uPA inhibitory activity (Sherman et al., 1992).

DNA sequence analysis of clones which maintained functional activity against uPA, but demonstrated decreased vitronectin binding identified 15 mutations in 6 clones, including 2 silent substitutions. Each of these 15 mutations were constructed and expressed separately, allowing for identification of five unique substitutions that result in a specific vitronectin binding defect. These mutations, Gln 55 Pro, Phe 109 Ser, Met 110 Thr, Leu 116 Pro, and Gln 123 Lys, demonstrated a spectrum of severity, and account for much of the observed binding defect in the original parental clones. The mutations were all located in a relatively small area on the surface of PAI-1, in α-helices C and E and β-strand 1A. This localization suggested a possible mechanism for vitronectin's stabilization of PAI-1. By cross-linking β-sheet A to other PAI-1 secondary structural elements, vitronectin may prevent the movement of β-sheet A necessary for full insertion of the reactive center loop, during the transition to the latent conformation. Finally, it is interesting to note that each of the mutations identified, affected only hydrophobic or polar residues, and not charged amino acids. Thus, this domain would likely have been missed in a traditional "alanine scan" approach focusing on clusters of charged residues.

Conversion of PAI-1 to a Substrate:

A common feature of inhibitory serpins is the presence of a small uncharged residue at the P14 position within the reactive center loop (Huber et al., 1989). In contrast, several non-inhibitory setpins have either a Glu or Arg residue at this position. Carrell and coworkers have suggested that retention of these small side chain residues is required for inhibitor function, because the reactive center loop must partially insert into β-sheet A in order to acquire the canonical shape necessary for effective inhibition. (Carrell et al., 1991; Carrell et al., 1992.)

A PAI-1 mutant was thus constructed, purified, and analyzed where the P14 Thr residue (residue 333) was replaced with Arg (Lawrence et al., 1994c). Comparison of the activity of this mutant to wtPAI-1 confirmed that it had lost its inhibitory function towards uPA. In contrast, the binding of mutant and wtPAI-1 to catalytically inactive anhydrotrypsin was nearly identical. SDS-PAGE analysis with both uPA and tPA, showed that the mutant PAI-1 had been converted to a substrate and demonstrates that the lack of inhibitory activity is not due to enhanced conversion of the mutant to the latent conformation. These data suggest that loop insertion is apparently not required for induction of the canonical conformation, but is essential for formation of a stable enzyme-inhibitor complex. These results also suggest that a functional catalytic mechanism is necessary to induce the conformational change that leads to loop insertion.

Construction and Analysis of a PAI-1 P14 Saturation Mutant Library:

In order to better study the inhibitory mechanism of PAI-1, a library of PAI-1 mutants containing all possible amino acid substitutions at the P14 position was created by site-directed mutagenesis. DNA sequence analysis of sixty-six independent clones from this library identified 14 unique mutants. Together with wtPAI-1 and P14 Arg, every possible amino acid substitution at P14 except Ala, Pro, Ser, and Trp were examined. Determination of the specific inhibitory activity, and second-order rate constants for each mutant towards uPA, indicated that except for Asp, Glu, and Lys all were efficient inhibitors. Thus, even though all inhibitory serpins identified to date have small side-chain residues at P14, residue size appears not to be critical for inhibitory function, at least in PAI-1. In contrast, charge, either positive or negative, radically reduces inhibitor function.

Immunoblotting of all 14 mutants following incubation with excess uPA demonstrated that all of the inhibitors form SDS-stable complexes with uPA except Arg, Asp, Glu, and Lys. An explanation for these results suggested that movement of the P14 side-chain into β-sheet A is essential for stable inhibition, and this movement requires removing a residue from the solvent, into the hydrophobic environment beneath β-sheet A. Depending on the nature of the specific residue being buried, this movement may become more or less energetically unfavorable, affecting the rate of insertion to a degree where it is not compatible with inhibition. Consistent with this explanation, pH had very little effect on the activity of wtPAI-1, however, it dramatically reduced the activity of P14 His (Lawrence et al., 1994c). Since the P14 residue is structurally the same at pH 9 and pH 5, these data definitively illustrate that charge is a critical factor in determining which pathway the inhibitor takes. Finally, an approximate pKa for this His residue is ~6.5. This suggests that the His side-chain is likely to be very solvent accessible, and therefore is unlikely to be significantly inserted into β-sheet A, prior to reaction with an enzyme. These data suggest that both the active and substrate forms of PAI-1 must be in very similar conformational states.

Others have suggested that serpin inhibition moves down a branched pathway leading to either stable inhibition or turn-over of the serpin as a substrate (Schechter et al., 1993; Cooperman et al.; 1993, Gettins et al., 1993). Our data is consistent with this proposal and suggests that a charge at P14 most likely affects the branch point of the pathway. Furthermore, it suggests that this branch point occurs when P14 inserts its side-chain into β-sheet A. However, the observation that wtPAI-1 can be stably isolated as a pure substrate (Declerck et al., 1992) suggests that the two forms may represent independent stable conformations.

Construction of PAI-1 Point Mutants with Greater Stability in vitro:

On the basis of the recently published crystal structure of latent PAI-1 (Mottonen et al., 1992), a series of mutant molecules that might be less likely to assume the latent conformation were constructed (Lawrence et al., 1994). It was hypothesized that disruption of an ion pair between P4'Glu and Arg30 might destabilize the latent conformation and thereby favor the active form of PAI-1. Three mutants that interrupt this ion pair were produced: Arg30>Glu, P4'Glu>>Arg and P4'Glu>>Pro. In each case the half-life of PAI-1 at 37° C. was extended compared to the 1.1 hour observed for wild-type PAI-1: approximately 1.2 hours for P4'Glu>>Arg, 2.1 hours for Arg30>>Glu and 2.0 hours for the P4'Glu>>Pro mutation. An additional PAI-1 variant potentially reconstituting the ion pair via mutations at both Arg30>>Glu and P4'Glu>>Arg still demonstrated an extended half-life in vitro (approximately 1.8 hours). These results suggest that although disrupting the ion pair present in the latent conformation of PAI-1 can retard the conversion from active to latent, other factors must also affect this transition.

Circular dichroism (CD) spectra analysis (Strandberg et al., 1991) indicated similar secondary structural components for the PAI-1 mutants, as well as active and latent wild-type PAI-1. In contrast, thermal denaturation curves monitored by CD (at a constant wave length of 222 nm) demonstrated that latent PAI-1 was considerably more thermostable than the active form.

Construction and Screening of a PAI-1 Random Mutant Library:

A library of random PAI-1 mutants has been constructed in the λ phage vector λEXlox (Novagen). The similar λgt11 expression system has been extensively used for antibody cloning approaches (Ginsburg et al., 1986; Ginsburg et al., 1985; Ginsburg et al., 1992). The advantages of a phage vector system include high efficiency of in vitro packaged phage infection compared to plasmid transformation and the capacity to rapidly screen large numbers of mutants on a single plate. Lytic phage growth should also liberate free, soluble protein from each plaque without the requirement for a lysis procedure. An added advantage of λEXlox is the facility for automatic subcloning using Cre-loxP mediated excision of plasmids from the phage vector. The resulting plasmid will already contain the PAI-1 sequences in the proper position for expression from the T7 promoter, thus allowing high level protein production and obviating the need for subcloning into pET3a. The coding sequence for mature PAI-1 was subcloned into the λEXlox vector using a PCR strategy. Expression of functionally active PAI-1 was confirmed, both in the phage construct as well as the automatically subcloned derivative plasmid. Random mutagenesis was next performed by PCR with error-prone Taq polymerase at increased concentrations of $MgCl_2$ and $MnCl_2$ and unbalanced dNTP concentrations (Cadwell et al., 1992). The mutagenized PAI-1 insert was subcloned into the phage vector, packaged with a commercial λ phage packaging extract (Gigapack, Stratagene) and plated on host strain BL21(DE3). The initial library constructed contained ~$10^6$ independent clones.

In order to rapidly screen large numbers of mutant phage, an efficient filter based screening assay was developed, based on formation of an SDS-stable complex between tPA and active PAI-1. Nitrocellulose filters were incubated with 10 mg/ml tPA (Genentech) in TBS, rinsed extensively in TBS to remove unbound ligand and blocked with 3% BSA containing 10 mM IPTG. Filters were then placed directly on top of the phage lawn. Recombinant PAI-1 liberated into the plaque by phage cell lysis, was then able to bind tPA. Filters were rinsed in TBS containing 0.5% SDS, and the PAI-1 detected with biotinylated, affinity-purified, polyclonal, anti-PAI-1 antibody (Sherman et al., 1992). Only active PAI-1 was capable of forming an SDS-stable, complex with filter bound tPA. In the absence of SDS, a weaker, but specific signal is also seen with an inactive PAI-1 mutant P1Ala-P1'Met, presumably due to noncovalent interaction with tPA.

Identification of PAI-1 Mutants with Increased Functional Stability:

The PAI-1 λEXlox random mutant library was screened in duplicate for active PAI-1 binding to tPA coated filters. The first screen was performed as described above. After 2 hours of incubation the filters were removed and the bacterial plates incubated for an additional 14 hours. After which, a fresh tPA coated filter (without IPTG) was reacted with the plate for 2 hours. Both filters were then processed for PAI-1 binding as above. While ~5000 PAI-1 positive plaques/plate were observed on the filter of the first lift, only 1–4 plaques/plate retained functional PAI-1 on the filter of the second lift. These positive phage were plaque purified, automatically subcloned, retransformed into BL21 (DE3) and PAI-1 protein expression induced.

Determination of the functional half-lives from lysates with each of these mutants identified 14 clones with half-lives significantly extended compared to wtPAI-1, with the most stable mutant having a functional half-life of ~150 hr at 37° C. These were then subjected to DNA sequence analysis to identify the mutations in each clone. The appearance of mutations at the same location in multiple clones strongly suggested that these residues may be responsible for the enhanced stability. Construction of 15 of the identified mutations individually demonstrated that while many of the mutations contributed to the extended half-lives, the most functionally stable clones required multiple mutations acting in cis. Several of the stabilizing substitutions occurred at serpin consensus sites that were divergent in PAI-1. These results suggest that PAI-1 may have evolved an intrinsically labile structure as a way of regulating PAI-1 activity.

EXAMPLE 2

ANALYSIS OF SYNTHETIC PEPTIDES THAT BLOCK PAI-1 ACTIVITY

Studies have suggested that synthetic peptides homologous to the reactive-center loop of various serpins other than PAI-1 intercalate into those active serpins as the central strand of β-sheet A thereby inactivating the inhibitor by converting it to a substrate (Carrell et al., 1991; Schulze et al., 1990; Björk et al., 1992). To test if PAI-1 could be inactivated in this way, five peptides were synthesized and tested for their ability to inactivate PAI-1 (FIG. 1). First, an 8 residue synthetic peptide corresponding to residues P14 through P7 of the PAI-1 reactive center loop, together with 2 homologous peptides were synthesized by methods well known in the art. The first peptide, Thr-Val-Ala-Ser-Ser-Ser-Thr-Ala (wt8-mer, SEQ ID NO: 2), was equivalent to wtPAI-1 residues 356–363. The second peptide, Thr-Glu-Ala-Ser-Ser-Ser-Thr-Ala, (V→E PAI 8-mer, SEQ ID NO: 3), was identical except that the Val residue in the second position was replaced with Glu to enhance solubility. The third peptide, Thr-Glu-Ala-Ala-Ala-Ala-Thr-Gly (Consensus, SEQ ID NO: 4), was based on a serpin reactive center loop consensus sequence (Lawrence et al., 1990). Analysis of each of these 8 mer peptides for their ability to inactivate PAI-1 is shown in FIG. 2. Incubation of PAI-1 with increasing concentrations of each peptide decreased the PAI-1 functional half-life from, 9.0 hr at 25° C. in the absence of peptide, to 1.2 hr with both V→E PAI 8-mer (SEQ ID NO:3) and consensus peptides (FIG. 1). An even more dramatic loss of PAI-1 activity was seen with the wild-type peptide where the lowest functional half-life obtained, 0.7 hr, was nearly half that of the other two peptides.

The IC50 values for the inactivation of PAI-1 by each of these peptides was also performed. By this analysis too, the wild-type peptide was significantly more efficient than the other two, with an IC50 value of 230 μM, compared to 1.6 mM peptide for both the V→E PAI 8-mer (SEQ ID NO:3) and consensus peptides (FIG. 2). These data indicate that either the presence of a Val residue at the P13 position in the wild-type peptide is crucial for its increased effectiveness, or that the Glu residue is particularly disruptive, since the V→E PAI 8-mer (SEQ ID NO: 3) is identical to the wt8-mer (SEQ ID NO: 2) except for the Val to Glu substitution in the second position. Furthermore, the nearly identical IC50 values and limiting rates for SEQ ID NO:3 and consensus peptides suggest that the remaining residues, C-terminal of P13, are less critical for peptide-PAI-1 interactions. In earlier reports of peptide inactivation of α1AT and antithrombin III, the rates of inactivation were significantly slower than those observed here, even at 37° C. (Schulze et al., 1990; Björk et al., 1992). Interestingly, the peptides used in these studies also had Glu in the P13 position.

Since previous studies had demonstrated that reactive-center peptide treated serpins were converted to substrates (Carrell et al., 1991; Schulze et al., 1990; Björk et al., 1992), the peptide treated PAI-1 samples were incubated with tPA and analyzed by SDS-PAGE. These results demonstrate that in contrast to untreated PAI-1, which forms SDS-stable complexes with tPA, the majority of the peptide treated PAI-1 was cleaved by tPA. Quantitation of the cleaved PAI-1 by scanning densitometry, indicated that following reaction with peptides approximately 80% of the PAI-1 was converted to a substrate. Furthermore, the lack of any high molecular weight complexes in these samples suggests that the remaining unreacted PAI-1 had been converted to the latent form. This latter result appears to represent the natural conversion of PAI-1 to the latent form and not a function of peptide treatment, since control incubations in the absence of peptide also resulted in approximately 20% conversion of PAI-1 to the latent form (data not shown). Interestingly, even though the rates of inactivation by different peptides is quite different, the mechanism appears to be similar with all three peptides, and is likely to be analogous to the inactivation observed with other serpins, where peptides are thought to intercalate into β-sheet A (Carrell et al., 1991; Schulze et al., 1990; Björk et al., 1992).

Figure 3:
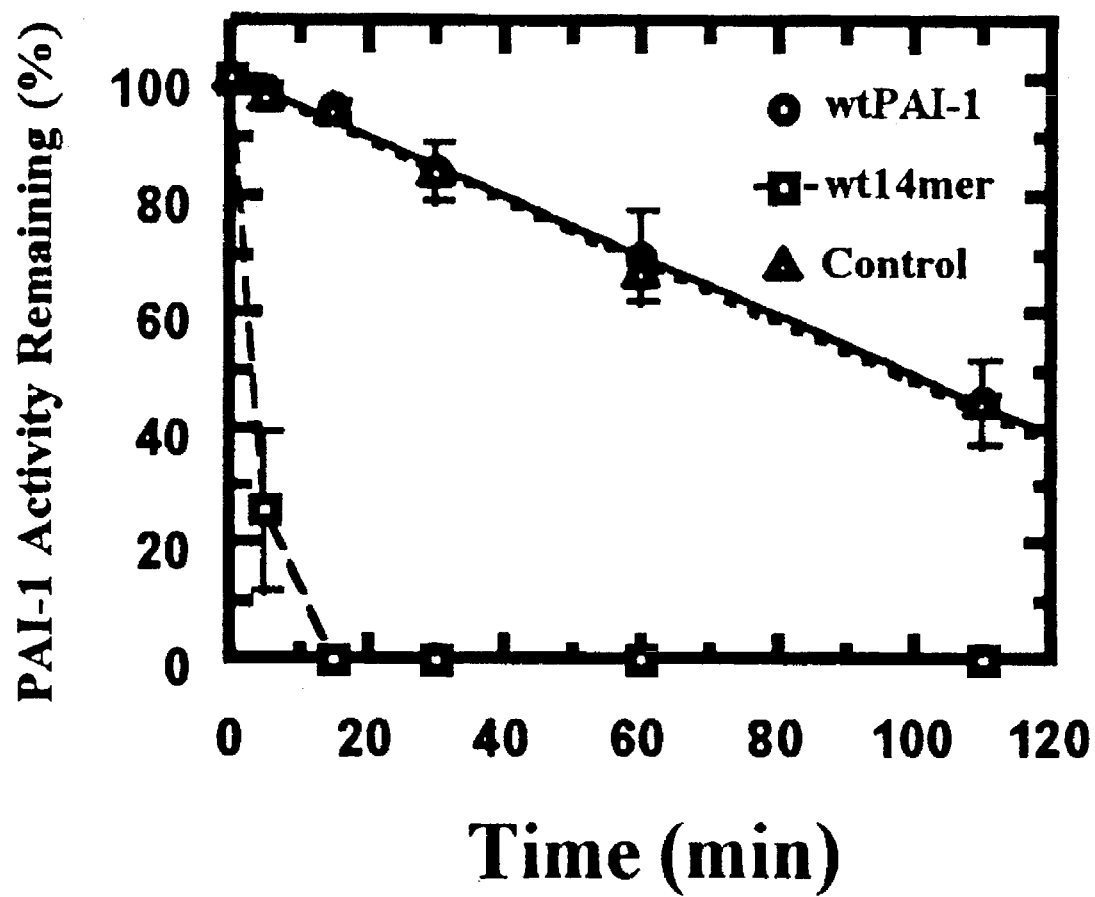
FIG. 3 shows the inactivation of plasminogen activator inhibitor-1 in the presence and absence of a peptide with SEQ ID NO:1. PAI-1 (0.7 µM) was incubated for times shown either alone, or with 55 µM of a peptide with SEQ ID NO: 1 or a control peptide.

The marked difference noted with the different peptides suggested that other, more effective peptides could be identified. Therefore, a 14 residue peptide corresponding to P14-P1 residues, Thr-Val-Ala-Ser-Ser-Ser-Thr-Ala-Val-Ile-Val-Ser-Ala-Arg (wt14-mer, SEQ ID NO: 1) of PAI-1, was synthesized, and tested for its ability to inactivate PAI-1. This peptide was an extremely potent inactivator of PAI-1, yielding a $t_{1/2}$ of approximately 4 min at 37° C. with a peptide concentration of only 55 μM. This compares to $t_{1/2}$ for untreated PAI-1, or PAI-1 treated with an irrelevant peptide, of 90 min (FIG. 3). This rate of inactivation is significantly faster than that observed with the wild-type 8-mer peptide. These results are described in Example 3.

Comparison of the difference in $t_{1/2}$ for untreated PAI-1 demonstrates that increasing the temperature 12° C.

decreases the t2 of PAI-1 6-fold, from 540 min to 90 min, while the corresponding drop for the wt14-mer peptide compared to the wt8-mer peptide is 100-fold, from over 400 min to 4 min, at similar peptide concentrations (55 μM). These data show that the 14 residue peptide is much more effective than the 8 residue peptide at inactivating PAI-1. The data used to generate FIGS. 2 and 3 are listed in the Table below.

| Peptide | Peptide (mM) | $t_{1/2}$ (hr) | $k_{obs}$ (hr$^{-1}$) | k (M$^{-1}$ s$^{-1}$) |
|---|---|---|---|---|
| SEQ NO ID NO: 2 | .015 | 7.5 | .093 | 1.7 |
|  | .025 | 7.8 | .089 | .99 |
|  | .045 | .62 | 1.1 | 6.9 |
|  | .064 | .072 | 9.6 | 42 |
| SEQ NO ID NO: 3 | .05 | 7.7 | .090 | .50 |
|  | .1 | 5.5 | .13 | .35 |
|  | .15 | 3.5 | .20 | .37 |
|  | .2 | 2.4 | .28 | .40 |
|  | .246 | 2.1 | .33 | .37 |
|  | .3 | 1.7 | .42 | .39 |
|  | .4 | 1.4 | .48 | .33 |
|  | .5 | .87 | .79 | .44 |
|  | .6 | .71 | .98 | .45 |
| SEQ NO ID NO: 4 | 1.5 | 5.4 | .13 | .024 |
|  | 2.5 | 3.3 | .21 | .024 |
|  | 3.5 | 2.5 | .28 | .022 |
|  | 5.04 | 1.8 | .38 | .021 |
|  | 7 | 1.6 | .44 | .017 |
|  | 9 | 1.3 | .54 | .017 |
|  | 11 | 1.2 | .58 | .015 |
| SEQ NO ID NO: 1 | 1.5 | 5.8 | .12 | .022 |
|  | 3.5 | 2.7 | .25 | .020 |
|  | 5.5 | 2.5 | .28 | .014 |
|  | 7 | 2.2 | .31 | .012 |
|  | 9 | 1.3 | .54 | .017 |
| SEQ NO ID NO: 5 | 1 | 7.2 | .097 | .027 |
|  | 1.3 | .20 | 3.4 | .75 |

In contrast to the 8 residue peptides, SDS-PAGE analysis of wt14-mer, SEQ ID NO: 1, treated PAI-1 revealed that this inactivated form of PAI-1 did not behave as a substrate. This suggests that the mechanism of inactivation by the wt14-mer peptide may be different from that of the 8 residue peptides, and from other previously studied serpin peptides. Furthermore, the lack of SDS-stable complexes as well as cleaved PAI-1, suggests that the PAI-1 has been converted to the latent conformation.

Figure 4:
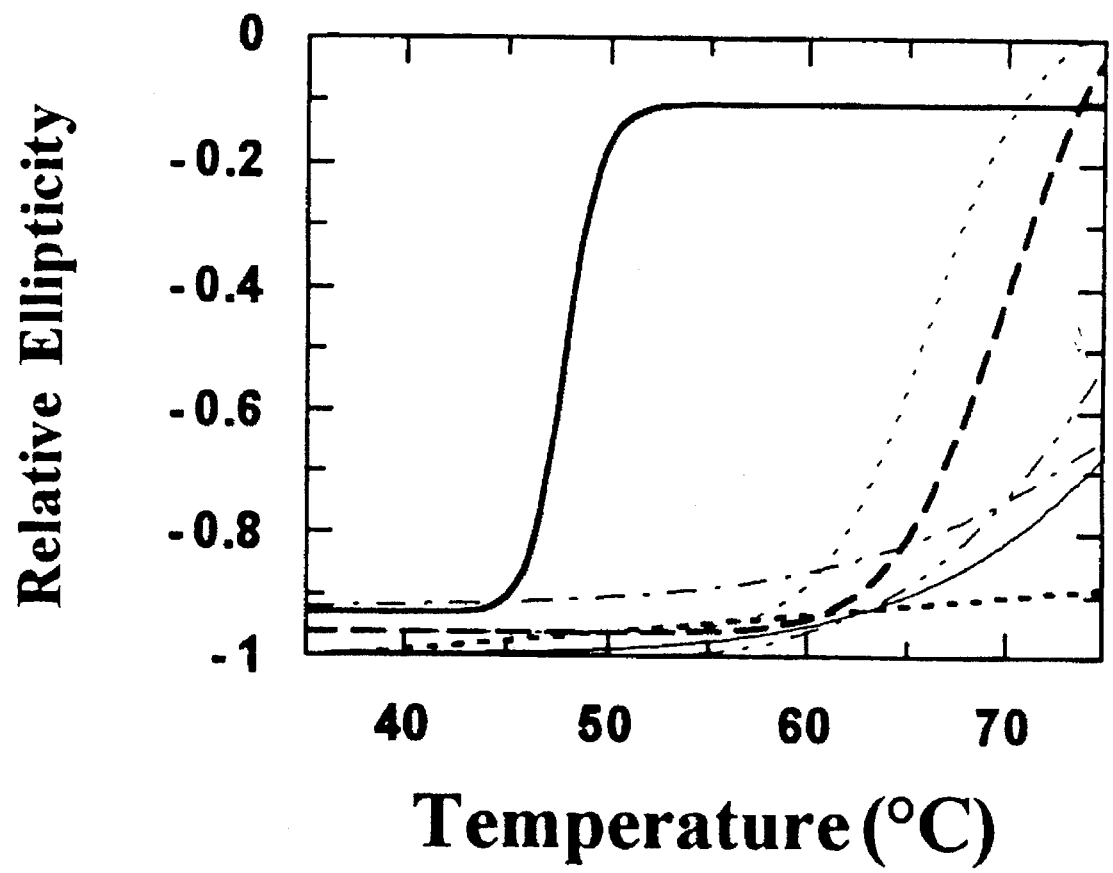
FIG. 4 shows the thermal denaturation of PAI-1 with or without the indicated peptides. PAI-1: Active (—); latent (--); elastase cleaved (-·-); PAI-1 with peptide of SEQ ID NO: 2 (-----); PAI-1 with peptide of SEQ ID NO: 3 (—); PAI-1 with peptide of SEQ ID NO: 4 (--); PAI-1 with peptide of SEQ ID NO: 1 (----).

We previously reported that while latent PAI-1 is significantly more thermally stable than active PAI-1, the cleaved form of PAI-1, with its reactive-center loop fully inserted, is the most thermally stable form, showing little tendency to melt up to 90° C. (Lawrence et al., 1994c). In addition, others have demonstrated that serpins in general become more stable when cleaved in their reactive-center loop or, when associated with a synthetic loop peptide, presumably due to the reconstitution of β-sheet A (Carrell et al., 1991; Schulze et al., 1990; Björk et al., 1992; Carrell et al., 1985; Gettins et al., 1988; Bruch et al., 1988). Therefore, thermal denaturation experiments were performed to test if the wt14-mer treated PAI-1 had a thermal stability similar to either latent or cleaved PAI-1. As expected, active PAI-1 was much less thermally stable than latent PAI-1 or elastase cleaved PAI-1 (FIG. 4). While all four peptide treated forms demonstrated thermal stabilities significantly greater than active PAI-1, none of the samples were as stable as cleaved PAI-1. Interestingly, the three samples treated with the 8-mer peptides had stabilities intermediate between elastase cleaved PAI-1 and the latent conformer. This is precisely the behavior expected for a serpin with a peptide intercalated into β-sheet A (Carrell et al., 1991; Schulze et al., 1990; Bj örk et al., 1992). In contrast, the wt14-mer (SEQ ID NO: 1) treated sample had a thermal stability very similar to latent PAI-1. If the 14 residue peptide were intercalated into β-sheet A, then the added length of the peptide bound to sheet A would be expected to increase the stability not decrease it. An earlier study with antithrombin III annealed to either a 6 residue peptide or a 13 residue peptide demonstrated significantly more structural stabilization from the longer peptide (Carrell et al., 1991).

These data, together with the refractive nature of the wt14-mer treated PAI-1 support the possibility that the peptide has induced PAI-1 to adopt the latent conformation. The basis for this mechanism is not immediately clear. However, the rapid loss of activity coupled with the relatively low concentration of peptide required for inactivation suggest that this type of mechanism may prove therapeutically useful for inactivating PAI-1 in vivo.

The observation that the wt14-mer peptide (SEQ ID NO: 1) very rapidly inactivated PAI-1 in a purified system suggested that this peptide might also be useful in inactivating PAI-1 in a more complex system. Therefore, the effect of the peptide on in vitro clot lysis was examined. These experiments indicated a significant enhancement of tPA induced platelet rich clot lysis in the presence of 70 μM peptide. This suggests that such a peptide might prove useful at targeting disruption of PAI-1 function in a clinical setting, and thereby enhance either endogenous fibrinolysis or thrombolytic therapy.

PAI-Peptide Annealing and Purification:

Peptides were dissolved in 1 mM HCl+1% TWEEN-80 (the three PAI peptides) (SEQ ID NOS: 1–3), or in 0.1M HEPES (SEQ ID NOS: 4–5), 0.1M NaCl, 0.1% PEG-8000, pH 12.5 (the two consensus peptides). Peptides were annealed to active PAI by incubation of active PAI in 0.1M HEPES, 0.1M NaCl, 0.1% PEG-8000, pH 7.4 with a peptide in its solvent. Ten percent of the final incubation mixture consisted of the peptide solvent. Incubation was carried out at 25° C. until no PAI inhibitory activity remained as determined by kinetics rate assays with trypsin, described below. The final concentration of PAI in the incubation mixture was either 0.9 μM (for kinetics assays) or 6.3 μM (for gels and purification). The peptide concentrations varied greatly due to the individual solubilities and rates of insertion of each peptide. These concentrations are given in the legends of the appropriate figures.

Upon completion of peptide annealing, the incubation solution contained a mixture of annealed PAI-peptide, latent PAI, and excess peptide. For circular dichroism (CD) spectra, melting curves, and mass spectroscopy determinations, the excess peptide was removed. This was done by loading the mixture on a heparin-sepharose column which had been equilibrated with 0.05M sodium phosphate, 0.15M NaCl, 1 mM EDTA, 0.01% TWEEN-80, pH 6.6. Washing the column with this buffer removed the excess peptide. The PAI-peptide and latent PAI were eluted together with 0.05M Sodium phosphate, 1M NaCl, 1 mM EDTA, 0.01% TWEEN-80, pH 6.6. The elution fractions showed a strong absorbance at 280 nm. The eluted sample was dialyzed against a 10,000×volume of the buffer needed for the particular procedure. The absorbance at 280 nm was used to determine the final protein concentration. The excess peptide was lyophilized, redissolved, and incubated with fresh active PAI to demonstrate that it was indeed peptide that had been removed from the mixture. Gel electrophoresis of the purified PAI samples, followed by scanning densitometry, was used to determine the amount of latent PAI in each sample.

Kinetics Assays:

During annealing of 0.9 µM PAI with a peptide, the residual inhibitory activity of PAI was measured after varying incubation times by assaying an aliquot of the sample with β-trypsin. Trypsin (1 nM final concentration) was added to the chromogenic substrate S-2222 (950 µM) with 27 nM PAI sample. The absorbance at 405 nm was measured continuously for at least 12.5 min in a Shimadzu UV-265 UV-visible spectrophotometer. The pseudo-first order rate constant of trypsin is an indirect measure of the amount of PAI that has lost inhibitory activity due either to annealing or to becoming latent. The rate constant of controls containing the peptide solvent but no peptide was subtracted from that of the experimental assays in order to correct for the effect of the simultaneous change of PAI from the active to the latent state.

Native and Denaturing Gel Electrophoresis:

SDS-polyacrylamide gel electrophoresis (SDS-PAGE) under nonreducing conditions was carried out according to the method of Laemmli (Laemmli, 1970) on 10% gels. Native gel electrophoresis with 5% gels was carried out by omitting SDS and boiling from Laemmli's method. All gels were stained with Coomassie brilliant blue. Gels of PAI-peptide samples were scanned with an LKB Ultroscan XL Laser Densitometer to determine the relative amounts of peptide-annealed and latent PAI.

Peptide Annealing:

Four of the five peptides have a net negative charge due to glutamic acid residues and the free carboxy terminus (FIG. 1). The wtPAI 8-mer has a net −1 charge (the carboxy terminus). The V→E PAI 8-mer (SEQ ID NO:3) and consensus 8-mer (SEQ ID NO:4) each have a −2 charge (the glutamic acid residue and the carboxyl group). The consensus 14-mer (SEQ ID NO:5) shows a −1 charge due to the glutamic acid residue (the carboxyl group's negative charge is balanced by the +1 charge of the P1 arginine). The PAI 14-mer (SEQ ID NO:1) is uncharged since it contains no glutamic acid and the arginine and carboxyl groups neutralize each other. Because of the negative charges of 4 of the peptides, native gels of PAI annealed to these peptides should show a band which migrates more quickly than the band representative of free active PAI. Similarly, if one of these peptides is incubated with PAI but fails to form a strong interaction with PAI, native gels should show a band which migrates identically to the free PAI.

Active and latent PAI cannot be distinguished on the basis of mobility. Active PAI incubated with any of the 8-mers showed increased electrophoretic mobility when compared with free active PAI. This result is consistent with the peptide strongly interacting with PAI, as would be the case if it were inserted into β sheet A. Only a single major band was visible for the V→E PAI 8-mer, and the magnitude of the increased mobility was proportional to the magnitude of the peptide's negative charge. Therefore, it appears that the PAI-peptide complex forms in a definite stoichiometric ratio, probably 1 PAI molecule: 1 peptide. The wtPAI 8-mer annealed to PAI shows two bands consistent with −1 and −2 charges. Therefore, there is a second binding site for this peptide which is occupied in about half of the annealed API molecules.

Since the PAI 14-mer has no charge, whether or not a PAI-peptide complex forms cannot be determined by native gel electrophoresis. Accordingly, active PAI incubated with this peptide showed a band at the same position as free active PAI.

Latent PAI incubated with any of the peptides showed a band with the same mobility as active or latent PAI. Therefore, latent PAI does not form a stable complex with the peptides. Again, this is consistent with peptides inserting into the β sheet upon annealing. Since the reactive site loop is inserted into β sheet A in latent PAI (Mottonen et al., 1992), it is not possible for a peptide to insert in this position.

Activity of Peptide-Annealed PAI:

When active PAI is incubated with a target enzyme, such as tPA, uPA, or trypsin, it forms a very stable complex with the enzyme in a 1:1 molar ratio. A small amount of the cleaved substrate form of PAI is also formed with a slightly lower molecular weight than that of active PAI. These 3 forms of PAI (active, enzyme-complexed, and substrate) are easily distinguished by SDS-PAGE. Active and latent PAI migrate together on a gel and cannot be distinguished.

PAI that had been incubated with peptide was tested for inhibitory and substrate activity by incubating with tPA, uPA or trypsin. SDS-PAGE was then performed on the samples. Free PAI formed a complex band when incubated with any of the enzymes, as well as a faint band indicative of cleaved PAI. Because substoichiometric amounts of enzyme were used there was also a band for free PAI. When PAI was incubated with any of the peptides, the electrophoretic mobility was the same as that of free PAI after denaturing with SDS. When PAI was annealed to any of 8-mers, then allowed to react with tPA, uPA or trypsin, no PAI-enzyme complex band was seen. Instead a strong band appeared with the electrophoretic mobility of cleaved PAI, indicating that the 8-mer-annealed PAI had been converted to a substrate of these enzymes.

PAI incubated with the PAI-14 mer showed a different result when different peptide concentrations were used. At low peptide concentration a significant substrate band formed along with the dominant latent PAI band. At high peptide concentration almost all of the PAI is in the latent conformation, with only a trace of cleaved PAI.

Kinetics of Peptide Annealing:

When incubated at 25° C. in the reaction buffer, PAI spontaneously converts from an active to a latent conformation with a half-life of 9.1 hours. Control assays were performed in which the incubation solution contained the peptide solvent but no peptide. When the PAI incubation mixture included 1 mM HCl+1% TWEEN-80, the half-life of the active to latent conversion was 7.2 hours. When the PAI was incubated with the solvent for the consensus peptides (the HEPES buffer, pH 12.5), the half-life was about 9 hours. When active PAI was incubated with any of the peptides, it became inactivated more quickly than can be explained by the normal active→latent conversion. The rate of inactivation was directly proportional to the peptide concentration at a constant PAI concentration.

The rates of annealing of the V→E PAI 8-mer (SEQ ID NO: 3) and consensus 8-mer (SEQ ID NO:4) were very similar, with a second-order rate constant, k, in the linear portion of the curve of k=$0.023M^{-1}S^{-1}$ for V→E PAI 8-mer, and k was about $0.018M^{-1}S^{-1}$ for consensus 8-mer. The wtPAI 8-mer (SEQ ID NO: 2) required much lower peptide concentrations to anneal at the same rate as the other 8-mers, with k=$0.44M^{-1}S^{-1}$.

Just as the wt PAI 8-mer (SEQ ID NO: 2) annealed to PAI much more quickly than the other 8-mers at a given peptide concentration, the PAI 14-mer (SEQ ID NO: 1) inactivated PAI much more quickly than consensus 14-mer (SEQ ID NO: 5). When 0.9 µM PAI was incubated with 64 µM PAI 14-mer (SEQ ID NO: 1), the half-life of PAI inactivation was 4.3 min whereas when 0.9 µM PAI was incubated with 1.2 mM consensus 14-mer, the half-life was about 12 min. The table herein in example 2 shows the half lives observed with varying concentrations of the peptides in accordance with SEQ ID NO:1–5.

EXAMPLE 3

INACTIVATION OF PLASMINOGEN ACTIVATOR INHIBITOR 1 BY Thr-Val-Ala-Ser-Ser-Ser-Thr-Ala-Val-Ile-Val-Ser-Ala-Arg

Materials:

The N-acetyl-tetradecapeptide of SEQ ID NO: 1, Ac-Thr-Val-Ala-Ser-Ser-Ser-Thr-Ala-Val-Ile-Val-Ser-Ala-Arg, corresponding to the P1-P14 sequence of PAI-1, was synthesized on a peptide synthesizer, (Rainin Instrument Co, Inc., Woburn, Mass.) using the 9-fluorenylmethyloxycarbonyl (Fmoc) strategy (Schulze et al., 1990). A control N-acetyl-tetradecapeptide, Ac-Asp-Arg-Val-Tyr-Ile-His-Pro-Phe-His-Leu-Leu-Val-Tyr-Ser (SEQ ID NO: 6), was purchased from Bachem Biochemica, Heidelberg, FRG. Lyophilized peptides were dissolved at a concentration of 1 mg/mL in 1 mM HCl containing 1% Tween 80, incubated 15 minutes at 70° C., then stored at room temperature. Recombinant PAI-1 was purified as described previously (Sherman et al., 1992), and recombinant, single chain t-PA (580,000 IU/mg) was obtained from Genentech, Inc. (South San Francisco, Calif.). Human glu-plasminogen, human α-thrombin, and Spectrozyme-tPA were from American Diagnostica, Inc. (Greenwich, Conn.). Fluorescein-labeled fibrinogen was prepared as previously described (Fay et al., 1994) and vitronectin was a gift of D. Mosher.

Plasminogen activator inhibitor 1 activity assay:

PAI-1 (0.7 µM) was incubated at 37° C. with either P1-P14 peptide or control peptide (55 µM) in 0.1M HEPES, 0.1M NaCl, 0.1% PEG (MW 8000), pH 7.4 (assay buffer). At timed intervals 0–110 minutes), 5 µL of the PAI-1:peptide mixture was added to 96 well microtiter plates containing 45 µL of t-PA (0.03 µM in assay buffer), then incubated for 30 minutes at 37° C. Spectrozyme t-PA (final concentration of 150 µM) was added to yield a final reaction volume of 70 µL, and 30 minutes later the absorbance at 405 nm was determined in a THERMO-max (Molecular Devices, Palo Alto, Calif.) microplate reader. 100% PAI-1 activity was defined as activity observed at time zero, while 0% PAI-1 activity was defined as that observed in the absence of PAI-1. A standard t-PA activity curve, derived from absorbance values of varying concentrations of t-PA incubated in the absence of PAI-1, was used to determine PAI-1 activity.

SDS polyacrylamide gel electrophoresis (PAGE):

SDS-PAGE was performed using a PhastSystem (Pharmacia), Upssala, Sweden, according to manufacturer's instructions. Gels were stained with Coomassie Brilliant Blue.

Platelet preparations:

Blood samples were collected by peripheral venipuncture from normal subjects into acid-citrate-dextrose anticoagulant (0.8% w/v citric acid, 2.2% trisodium citrate, 2.45% dextrose) at a ratio of 6 volumes of blood to 1 volume of anticoagulant. Donors had not consumed aspirin for at least 7 days prior to phlebotomy. Washed platelets were prepared by repeated centrifugation as previously described (Fay et al., 1994), then resuspended in Tyrode's buffer (137 mM NACl, 2.68 mM KCl, 2 mM $CaCl_2$, 1 mM $MgCl_2$, 0.36 mM $NaH_2PO_4$, 11.9 mM $NaHCO_3$, 5 mM HEPES, 0.1% glucose, 0.35% bovine serum albumin, pH 7.35).

In vitro clot lysis assays:

Clot lysis assays were performed as previously described (Fay et al., 1994). A mixture of glu-plasminogen (0.2 µM), fluorescein-labeled fibrinogen (3 µM), PAI-1 (0.7 µM) was prepared. t-PA (20 nM) was added 30 minutes after clot formation and clot lysis was allowed to occur for 60 minutes at 37° C., after which the tubes were centrifuged (16,000×3 min), and 80 µL of the supernatant was removed and diluted into 1.2 mL of 10 mM Tris-HCl, 140 mM NaCl, pH 7.5. The fluorescence of this dilution was measured and % clot lysis was calculated, as previously described (Fay et al., 1994).

In experiments with platelet-rich clots, platelets ($2.5 \times 10^8$/mL) were added as a source of for PAI-1, and t-PA was added to a final concentration of 75 pM immediately following the addition of thrombin. Clot lysis was allowed to proceed for 90 minutes.

Effect of P1-P14peptide on PAI-1 activity:

PAI-1 spontaneously converts from an active to an inactive, or latent, conformation with a $T_{1/2}$ of 1–2 hours at 37° C. (Lawrence et al., 1994). Consistent with previous data, we determined the $T_{1/2}$ of PAI-1 to be 98±18 minutes (mean ±SD of 3 experiments) under the experimental conditions described above. The addition of Thr-Val-Ala-Ser-Ser-Ser-Thr-Ala-Val-Ile-Val-Ser-Ala-Arg (SEQ ID NO: 1) (55 µM) resulted in a 24-fold shortening of the PAI-1 $T_{1/2}$ to 4.0±3.0 minutes. In contrast, a control tetradecapeptide (SEQ ID NO: 6), at the same concentration, did not affect the PAI-1 $T_{1/2}$ (FIG. 3). Control reactions confirmed that neither peptide had any direct effect on t-PA activity.

Figure 5:
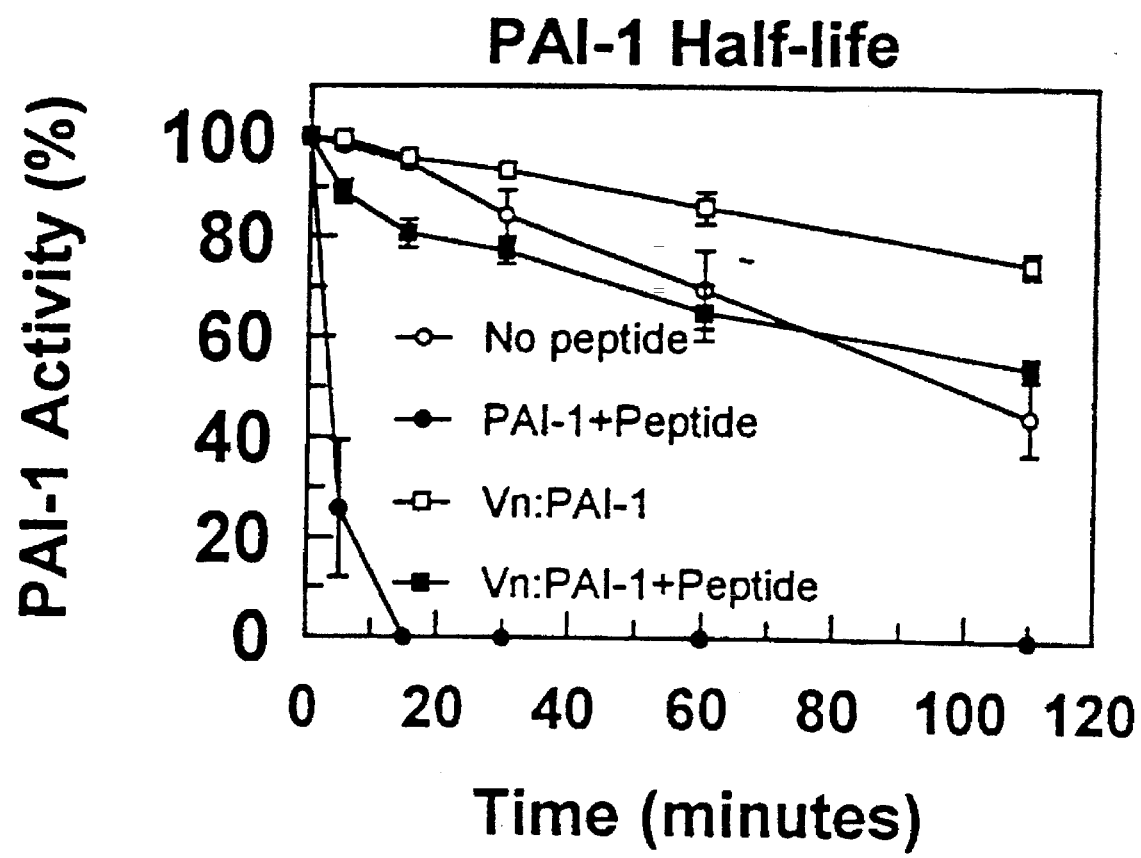
FIG. 5 shows the effect of a peptide with SEQ ID NO:1 on PAI-1 activity in the presence and absence of vitronectin.

Since vitronectin binds and stabilizes the active conformation of PAI-1, the capacity of the Thr-Val-Ala-Ser-Ser-Ser-Thr-Ala-Val-Ile-Val-Ser-Ala-Arg (SEQ ID NO: 1) to inactivate vitronectin-bound PAI-1 was examined. PAI-1 (0.7 µM) was incubated with vitronectin (1.7 µM) for 30 minutes at 37° C., then Thr-Val-Ala-Ser -Ser-Ser-Thr-Ala-Val-Ile-Val-Ser-Ala-Arg (SEQ ID NO: 1) or control peptide (55 µM) was added, and the PAI-1 $T_{1/2}$ was determined. In the presence of vitronectin, the $T_{1/2}$ of PAI-1 was prolonged approximately 2-fold (98±18 to 190±12 minutes), similar to previous reports (Declerck et al. 1988). Thr-Val-Ala-Ser-Ser-Ser-Thr-Ala-Val-Ile-Val-Ser-Ala-Arg (SEQ ID NO: 1) decreased the half-life of vitronectin-bound PAI-1 to 120±25 minutes, a 1.6 fold (FIG. 5).

Effect of P14 peptide on t-PA:PAI-1 complex formation:

SDS-PAGE was performed to determine the effect of Thr-Val-Ala-Ser-Ser-Ser-Thr-Ala-Val-Ile-Val-Ser-Ala-Arg (SEQ ID NO: 1) on t-PA:PAI-1 complex formation in the presence and absence of vitronectin. Although control tetradecapeptide did not prevent formation of SDS stable PAI-1:t-PA complexes, no t-PA:PAI-1 complex formation was observed when PAI-1 was preincubated for 15 minutes with Thr-Val-Ala-Ser-Ser-Ser-Thr-Ala-Val-Ile-Val-Ser-Ala-Arg (SEQ ID NO: 1). Consistent with the above kinetic data, vitronectin-bound PAI-1 retained the capacity to form complexes with t-PA following treatment with P1-P14 peptide. In contrast to previous studies with other serpins, SDS-PAGE analysis of the products of reaction of t-PA with Thr-Val-Ala-Ser-Ser-Ser-Thr-Ala-Val-Ile-Val-Ser-Ala-Arg (SEQ ID NO: 1) treated PAI-1 did not reveal increased amount of cleaved PAI-1, indicating that the peptide did not convert PAI-1 to a substrate form (Declerck et al., 1992).

Figure 6A:
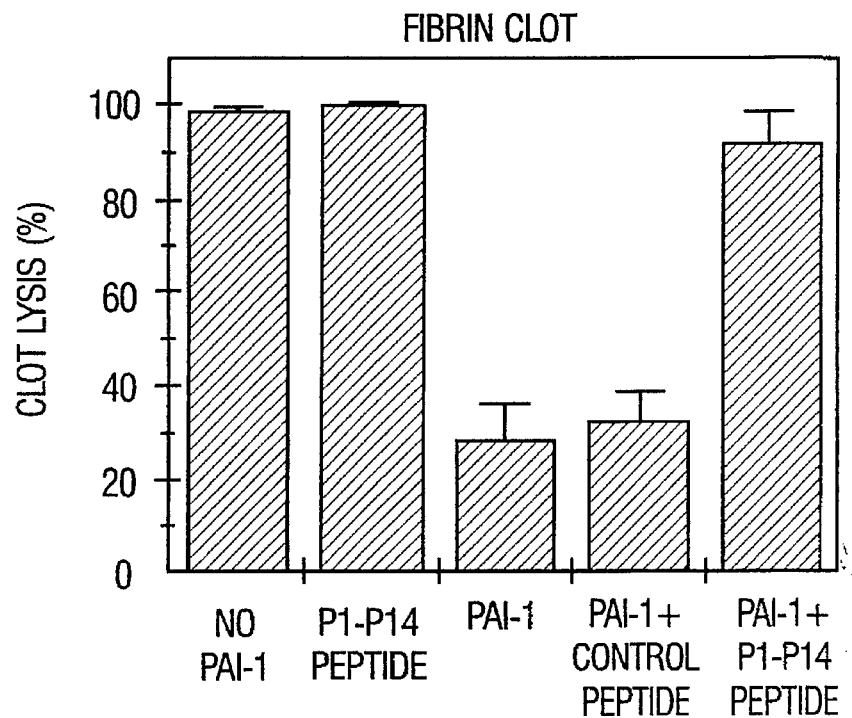
FIG. 6a shows the effect on clot lysis of a fibrin clot upon exposure to the indicated peptides.
Figure 6B:
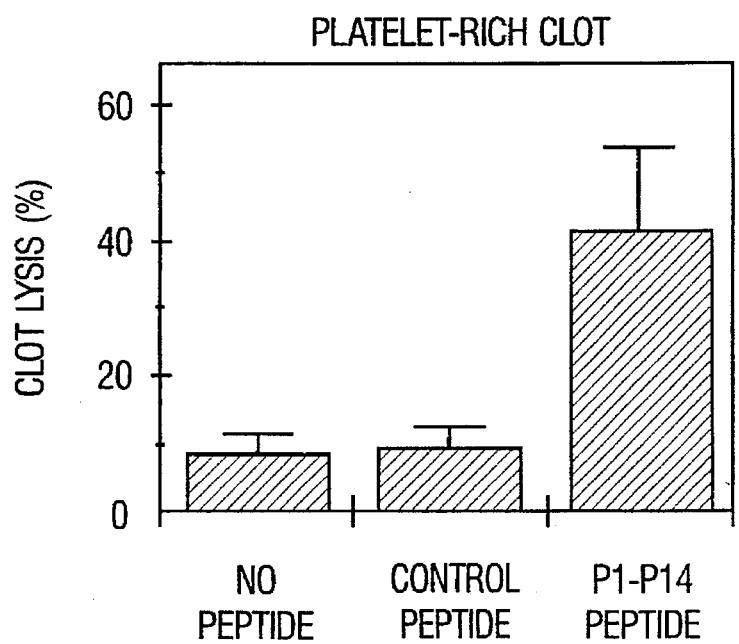
FIG. 6b shows the effect on clot lysis of a platelet rich clot upon exposure to a peptide of SEQ ID NO:1.

Effect of P1–P14 peptide on in vitro clot lysis:

To determine the capacity of the PAI-1 peptide to accelerate fibrinolysis, an in vitro clot lysis assay was performed. In the presence of PAI-1, clot lysis at 60 minutes was accelerated from 28±7% to 90±6% by the addition of Thr-Val-Ala-Ser-Ser-Ser-Thr-Ala-Val-Ile-Val-Ser-Ala-Arg (SEQ ID NO: 1) (FIG. 6a), while no augmentation of fibrinolysis by Thr-Val-Ala-Ser-Ser-Ser-Thr-Ala-Val-Ile-Val-Ser-Ala-Arg (SEQ ID NO: 1) was observed in the absence of PAI-1 (FIG. 6a). Similarly, the control peptide had no significant effect on clot lysis. Furthermore, the degree of clot lysis was proportional to Thr-Val-Ala-Ser-Ser-Ser-Thr-Ala-Val-Ile-Val-Ser-Ala-Arg (SEQ ID NO. 1) concentration (FIG. 3b). Since platelets are rich in PAI-1 (Erickson et al., 1985) and platelet-rich thrombi are resistant to t-PA-mediated clot lysis (Jang, et al., 1989), the effect of peptide on lysis of platelet-rich clots was also assessed. The lysis of platelet-rich clots at 90 minutes was increased from 8±3% to 41±12% by the addition of P1-P14 peptide (FIG. 6b).

The tetradecapeptide Thr-Val-Ala-Ser-Ser-Ser-Thr-Ala-Val-Ile-Val-Ser-Ala-Arg (SEQ ID NO. 1) corresponding to the P1-P14 sequence of PAI-1 is capable of rapidly inactivating PAI-1 and augmenting fibrinolysis in vitro. Although the plasma clearance of PAI-1 is relatively short (Vauhan et al., 1990; Colucci et al., 1985), the clearance of PAI-1 from thrombi and the extravascular compartment is likely to be much longer (Loskutoff, 1991; Mimuro et al., 1989b). The rapidity with which the P1-P14 peptide inactivates PAI-1 may be of potential clinical importance. PAI-1 levels have are elevated in young survivors of myocardial infarction (Hamsten et al., 1985) and a diurnal variation in PAI-1 levels corresponds to the diurnal pattern of myocardial infarction (Angleton et al., 1989). In addition, PAI-1 mRNA levels are elevated in atherosclerotic arteries (Schneiderman et al., 1992), and PAI-1 levels in plasma are positively correlated with the risk of recurrent myocardial infarction (Hamsten et al., 1987). Hence, this peptide approach provides a practical method to approach acute, and possibly chronic suppression of PAI-1 activity in vivo.

These results are consistent with previous studies performed with α-1-antitrypsin and antithrombin III (Björk et al, 1992; Schulze et al., 1990). X-ray crystallographic analysis of α-1-antitrypsin indicates that upon cleavage of the reactive center bond, the P1-P14 loop inserts as a new strand into the β-sheet A (Schulze et al., 1990). In addition, a synthetic tetradecapeptide, consisting of the same stretch of amino acids has been shown to form serpin peptide complexes with physical properties similar to those of cleaved α-1-antitrypsin (Schulze, et al., 1990), suggesting that the peptide can intercalate into the inhibitor and induce a conformational change that results in serpin inactivation. Studies with antithrombin III produced similar results (Björk et al, 1992).

The inactivation of PAI-1 by Thr-Val-Ala-Ser-Ser-Ser-Thr-Ala-Val-Ile-Val-Ser-Ala-Arg (SEQ ID NO: 1) is much more rapid than the inactivation of α-1-antitrypsin or antithrombin III by analogous peptides ($T_{1/2}$ of 4 minutes vs >1 hour at 37° C.). The rapidity with which PAI-1 is inactivated by its Thr-Val-Ala-Ser-Ser-Ser-Thr-Ala-Val-Ile-Val-Ser-Ala-Arg (SEQ ID NO: 1) may reflect its tendency to assume a latent conformation spontaneously. Unlike antithrombin III and α-1-antitrypsin, however, the substrate form of PAI-1 was not generated following incubation with P 1-P 14, suggesting an alternative mechanism of PAI-1 inactivation.

It is of note that the Thr-Val-Ala-Ser-Ser-Ser-Thr-Ala-Val-Ile-Val-Ser-Ala-Arg (SEQ ID NO: 1) is capable of inactivating PAI-1 in the environment of a platelet-rich clot, which contains both fibrin and vitronectin (FIG. 6b). These ligands probably play important roles in modulating PAI-1 function in vivo (Keijer et al., 1991; Reilly et al., 1992). Vitronectin is present in platelets and plasma and binds PAI-1 with a high affinity (Preissner et al., 1989; Seiffert et al., 1991). In addition, vitronectin stabilizes the active conformation of PAI-1, prolonging the $T_{1/2}$ approximately 2-fold in solution and up to 24 hours within the extracellular matrix (Declerk et al 1988; Mimuro et al., 1989). The stabilization of PAI-1 by vitronectin has been hypothesized to result from restriction of PAI-1-β-sheet A, interfering with the reactive center loop insertion which is required for PAI-1 conversion to latency (Lawrence et al., 1994a).

Consistent with this hypothesis, PAI-1 bound to vitronectin was highly resistant to peptide inhibition. However, the Thr-Val-Ala-Ser-Ser-Ser-Thr-Ala-Val-Ile-Val-Ser-Ala-Arg (SEQ ID NO: 1) was capable of accelerating clot lysis despite the presence of vitronectin in platelet-rich clots (FIG. 6b). A possible explanation may be that compared to vitronectin, the Thr-Val-Ala-Ser-Ser-Ser-Thr-Ala-Val-Ile-Val-Ser-Ala-Arg (SEQ ID NO: 1) reacts more readily with PAI-1 in the environment of a clot.

PAI-1 also binds to fibrin (Reilly et al., 1992), although with lower affinity than vitronectin, and it has been suggested that fibrin may serve to localize PAI-1 to actively forming thrombi (Reilly et al., 1992; Braaten et al., 1993). However, under the experimental conditions as discussed herein, the P1-P14 peptide nearly completely inhibited PAI-1 function in the presence of fibrin (FIG. 2a).

Since elevated PAI-1 levels are associated with thrombosis, inhibition of PAI-1 is a potentially useful therapy in preventing thrombosis. In addition, since platelet-rich thrombi contain markedly elevated levels of PAI-1 (Potter van Loon et al., 1992), and PAI-1 contributes to the resistance of platelet-rich clots to lysis with t-PA (Fay et al, 1994), inhibition of PAI-1 may prove useful in augmenting thrombolysis as suggested by previous studies with anti PAI-1 antibodies (Levi et al., 1992; Braaten et al., 1993). The larger volume of distribution of small peptides compared to antibodies might enhance the applicability of PAI-1 inactivation, potentially expending its use to in vivo settings. As the plasma concentration of PAI-1 is approximately 8-32 ng/mL (Booth et al., 1988), obtaining peptide PAI-1 ratios similar to those in our experiments (i.e. 80-fold molar excess of P1-P14 over PAI-1), could be easily attained in vivo. Furthermore, P1-P14 could provide a powerful model for the rational design of novel, non-protein inhibitors of PAI-1 function.

EXAMPLE 4

STOICHIOMETRY OF THE PAI-1-PEPTIDE COMPLEX

The most likely basis for inactivation of PAI-1 by both the 8-mer and 14-mer peptides is best explained by intercalation of the peptide into β-sheet A. Support for this model is provided by the apparent 1:1 stoichiometries of the serpin-peptide complexes (Schulze et al., 1990; Björk et al., 1992). However, very little data currently exist that demonstrate the exact nature of these complexes. Furthermore, results with the wt14-mer peptide suggest that different mechanisms of inactivation may result with different peptides.

The apparent conversion of PAI-1 to the latent conformation suggests that the wt14-mer peptide may act via an entirely different mechanism and possibly interact with PAI-1 at a different site. It is possible that all the peptides interact with β-sheet A, but that the wt14-mer induces self-insertion of the native reactive-center loop rather than binding itself. Alternatively the wt14-mer may interact with a completely different region in PAI-1, and through this interaction destabilize the active conformation.

Mutations in PAI-1 that both enhance its functional half-life and destabilize the latent conformation have been reported (Lawrence et al., 1994b). One interpretation of these data is that the active form of PAI-1 is a metastable conformation, and that the thermodynamically final folded form is the latent conformation. If the active conformation of PAI-1 is stabilized by an interaction between the native reactive-center loop and another part of the molecule, then it is possible that the wt14-mer (SEQ ID NO: 1) peptide may compete for this stabilizing association.

To distinguish between these possibilities, and to determine how and where each peptide reacts with PAI-1, experiments are performed that characterize the precise nature of the interaction(s) between PAI-1 and each peptide.

The first set of experiments is aimed at determining the stoichiometry of interaction between PAI-1 and each peptide. If the peptides are tightly associated with PAI-1, as would be expected if they are intercalated into β-sheet A, then quantitation of the peptide and PAI-1 following dialysis provides accurate measure of the stoichiometry.

In these experiments PAI-1 is reacted with peptide under conditions that yield complete PAI-1 inactivation. Following this an aliquot of each sample is reacted with enzymatic concentrations of tPA, subjected to SDS-PAGE, and the amount of substrate form relative to latent form quantitated by scanning densitometry. The remainder of the samples is extensively dialyzed to remove any unbound peptide, followed by quantitative amino acid composition analysis. This method has been used previously to determine serpin-peptide stoichiometries (Schulze et al., 1990, Björk et al., 1992).

Alternatively, the complexes are separated with trifluoroacetic acid and the amount of peptide and PAI-1 in each sample quantified following separation by reverse phase HPLC. By comparing the observed absorbance of both peptide and PAI-1 with known amounts of each, it is possible to precisely determine the molar amount of PAI-1 and peptide in each sample. Correlation of these data with the previously determined concentrations of substrate and latent PAI-1 in each sample also helps to clarify whether the peptides are associated with the substrate form, the latent form or both forms of the inhibitor.

Finally, if the complexes are sufficiently tight (such as biotin-avidin (Schwartz et al., 1994) and Heme-myoglobin (Katta et al., 1991) then electrospray ionization mass spectrometry permits a direct mass determination of the PAI-1-peptide complex. This analysis gives an exact mass of the complex. In earlier studies using electrospray mass spectrometry, the mass increase of recombinant PAI-1 that was partially inactivated by oxidation with N-chlorosuccinimide was determined. Compared to untreated PAI-1, a mass increase of 59 units was observed, suggesting that 4 of the 16 methionine residues in PAI-1 had been oxidized. These results indicate the level of sensitivity that can be obtained by this technique. These data demonstrate the stoichiometry of the interaction and also give a relative approximation of the strength of the association, since only very tight non-covalent complexes can be seen with this technique (Schwartz et al., 1994; Katta et al., 1991). Finally, it has been demonstrated that active PAI-1 has a larger Stokes radius than latent PAI-1, suggesting the two forms can be separated by equilibrium density gradient ultracentrifugation. If the conformation of the peptide-annealed form is similar to active PAI-1, as is likely for the substrate forms (Lawrence et al., 1994), then it should be possible to separate the two conformations by this method. Therefore, if the determined stoichiometries are less than 1, equilibrium density gradient ultracentrifugation is performed on the peptide treated samples, and isolated fractions with the different stokes radii reanalyzed as above. This clearly identifies which form(s) are associated with the peptide.

The experiments outlined in EXAMPLE 4 all rely on the assumption that the peptide, once associated with PAI-1, remains tightly bound. While this is a reasonable expectation for peptides that induce the substrate conformation, it is possible that the wt14-mer (SEQ ID NO: 1) peptide is only weakly associated with PAI-1, or possibly only transiently bound. Therefore, experiments are performed to determine the dissociation constant ($K_d$) for each peptide with PAI-1. For these studies, each of the four peptides are resynthesized without acetylation of the N-terminus. They are then radiolabled with acetylating reagent, ($^3$H) acetic anhydride (Amersham). Since the current peptides are acetylated at their N-terminus, these new peptides are functionally identical. Equilibrium dialysis experiments are then performed and $K_d$s calculated. While it may not be possible to calculate $K_d$ values for peptides that are intercalated tightly into the PAI-1 structure, it is sometimes possible to establish an upper limit.

EXAMPLE 5

IDENTIFICATION OF THE SITES OF INTERACTION BETWEEN PAI-1 AND SYNTHETIC PEPTIDES

Once the stoichiometries have been determined, studies are initiated to identify the peptide binding sites on PAI-1. In the first series of experiments, the newly synthesized peptides, with native N-termini are coupled to an excess of an $^{125}$I labeled heterobifunctional photoreactive cross-linking reagent, Sulfosuccinimidyl 2-(p-azidosalicylamido) ethyl-1,3'-dithiopropionate (SASD) (Pierce Chemical). The SASD binds to the free amino-terminus of the peptide, and the remaining unreacted SASD is then removed by incubation of the mixture with lysine Sepharose followed by centrifugation of the Sepharose to remove the SASD-lysine conjugate.

The SASD-peptide is then incubated with PAI-1 and complexes are allowed to form. The reactivity of the SASD-peptide with PAI-1 is monitored by determining the residual PAI-1 activity at various times of incubation following treatment.

Once the SASD-peptide has completely inactivated PAI-1, the PAI-1-SASD-peptide complex is extensively dialyzed to remove any unreacted peptide. An aliquot of each sample is also removed and reacted with enzymatic concentrations of tPA prior to SDS-PAGE. Scanning densitometry is then performed on this latter fraction to determine the ratio of substrate to latent PAI-1. Next the SASD-peptide is activated with UV light to permit the SASD to bind to PAI-1. The PAI-1 is then fragmented by digestion with either endoproteinase Lys-C, chymotrypsin $A_4$ or by chemical cleavage with cyanogen bromide. The PAI-1 fragments are then separated by SDS-PAGE and transferred to a polyvinylidene difluoride (PVDF) membrane (Matsudaira, 1987). Fragments that were cross-linked to the peptide are visualized by autoradiography for $^{125}$I. N-terminal sequence analysis of these fragments allows identification of the PAI-1 residues that are in close proximity to the peptide binding site.

By fragmenting the PAI-1-peptide complex both chemically and with multiple enzymes having different cleavage specificities, an overlapping set of PAI-1 fragments are obtained. This helps to narrow down the region where the specific site of cross-linking occurs. It is also possible that the peptide cross-links to more than one PAI-1 fragment. In that case, the different fragments can be located relative to one another in the PAI-1 three dimensional structure. With the data obtained from multiple methods of PAI-1 fragmentation it is possible to very accurately determine the position of the amino-terminal residue of the peptide when it is associated with PAI-1.

To further refine the site(s) of peptide interaction with PAI-1, a second set of N-terminal acetylated peptides are synthesized. These new peptides are identical to the current peptides except that they have C-terminal Lys residues substituted for their existing C-terminal amino acids. These peptides are reacted with SASD and PAI-1, and analyzed in the same manner as above. In this way a second set of data is generated localizing the C-terminal end of the peptide when bound to PAI-1. Finally, the alternative cross-linking reagent, N-Hydroxysuccinimidyl-4-azidosalicylic acid (NAS-ASA) (Pierce Chemical) could be used. This reagent has similar properties as SASD but does not contain a spacer between the two reactive groups and is therefore significantly smaller and less likely to disrupt peptide binding.

A second approach for identifying the peptide binding site on PAI-1 is by the technique of time resolved fluorescence spectroscopy. A series of PAI-1 variants containing two cysteine residues has been produced. By utilizing the specific reactive chemistry of the free sulfhydryls on the introduced cysteines, these PAI-1 variants are double labeled with two different fluorophores.

By determining the efficiency of electronic energy transfer between the donor and acceptor fluorophores, a measurement that acts as a spectroscopic ruler for the intramolecular distances between the two fluorophores are obtained (Stryer, 1968,; Steinberg, 1971; Gennis, 1976). By synthesizing peptides with the fluorophores rhodamine or dansyl attached to either the N-terminus or a C-terminal Lys residue and binding the labeled peptide to a fluorescein labeled PAI-1 single cysteine mutant, the distance between the fluorophore on the peptide and the fluorescein labeled cysteine is determined.

The precise position in three dimensions of the peptide fluorophore relative to PAI-1 is then be triangulated by determining the distance of the fluorophore from a series of single Cys mutants in PAI-1. Serine residues are chosen for substitution with Cys because there are 26 Ser residues spread approximately evenly throughout PAI-1, and because the size of the Ser side chain is similar to that of Cys and therefore the substitutions are less disruptive to the protein structure. Though the resolution with this technique is less than NMR or protein crystal structures, it is sufficient to determine if the peptides are associated with the central part of β-sheet A, or other regions of the molecule.

EXAMPLE 6

IDENTIFICATION OF PAI-1 RANDOM MUTANTS THAT ARE RESISTANT TO PEPTIDE MEDIATED INACTIVATION

An indirect approach to examine peptide binding to PAI-1 is to identify PAI-1 mutants that do not bind a specific peptide. A random mutagenesis strategy was successfully used to identify the vitronectin binding domain of PAI-1 (Lawrence et al., 1994a). A similar scheme is used to identify PAI-1 mutants that are no longer inactivated by each peptide.

Briefly, the PAI-1 cDNA is randomly mutated by error-prone PCR followed by treatment with hydroxylamine, after which the mutant cDNA pool is ligated into the E. coli expression plasmid pET3a. If the mutation frequency is controlled to yield approximately 3 substitutions per clone, then a pool of 126 clones contains one amino acid substitution at every position in PAI-1. However, approximately ⅔ of the clones are inactive due to global disruption of the protein structure (Lawrence et al., 1994a). Therefore, at least 400 clones must be screened to give complete coverage of the PAI-1 sequence. However, this minimal coverage is statistically unlikely to contain mutations at all positions in PAI-1. Furthermore, not all mutations occurring at critical positions will be equally effective at blocking peptide binding. Therefore, a three-fold over representation must be screened (1200 clones).

The mutant PAI-1 expression plasmid pool is then transformed into BL21 cells, and individual colonies are selected and inoculated into microtiter plates. The cells are then grown to an $A_{600}$ of 1.0, replica plated and PAI-1 expression induced with IPTG. After two hours of protein expression, bacterial cell lysates are prepared directly in the microtiter plates and PAI-1 functional activity against uPA is determined (Lawrence et al., 1994a).

Next, the wt14-mer peptide is added to a final concentration of 55 µM, and the samples incubated for 1 hr at 37° C. The wt14-mer peptide was chosen for analysis with the mutant library for two reasons. First, its rate of inactivation is the fastest of all four peptides and the concentration required is the lowest (t½ of 4 min. with 55 µM peptide at 37° C.). Second, studies with this peptide in a platelet rich clot lysis assay have indicated that the peptide is capable of inactivating PAI-1 in a complex milieu.

After peptide treatment PAI-1 activity is again determined, and any samples that demonstrate resistance to inactivation by the wt14-mer (SEQ ID NO: 1) are selected from the replica plate, regrown in a larger scale and DNA isolated for sequence analysis. Since it is likely that clones identified as being peptide resistant contain multiple mutations, and since it is unlikely that each of these mutations contribute to the observed phenotype, further analysis is necessary to identify the specific mutations responsible.

First, comparison of the placement of each identified mutation, from all of the peptide resistant clones, on the PAI-1 tertiary structure is made. If mutations are seen to be clustered within one region, then each mutation occurring in this region is constructed independently by site-directed mutagenesis and analyzed as an individual mutant. If no obvious clustering is seen, then all the mutations from each peptide resistant clone is constructed by site-directed mutagenesis and the individual mutants are tested for resistance to the peptide. This dissection is similar to the analysis described for identification of the vitronectin binding domain (Lawrence et al., 1994a).

After identifying PAI-1 point mutations that block the inactivation by the wt14-mer peptide (SEQ ID NO: 1), other peptides are analyzed with this library. First, the isolated mutations that prevent inactivation by the wt14-mer peptide are tested with each of the 8-mers. After this the wt8-mer peptide is screened with the same library with which the wt14-mer was screened. Finally, resistant mutants for the 8 residue peptide are tested with the other two 8-mers.

The identification of a number of point mutations that are resistant to peptide-mediated inactivation helps to define the site(s) of interaction between the peptides and PAI-1. Combining this data with the results of the cross-linking and fluorescence spectroscopy experiments discussed above clearly defines the PAI-1 peptide binding region(s). Furthermore, knowing where on PAI-1 the peptides interact and knowing the specific mutations that disrupt this interaction, without disrupting PAI-1 function, enhances understanding of the mechanism of peptide mediated inactivation. This is especially true for the wt14-mer peptide where the basis for inactivation appears to be unique.

EXAMPLE 7

BIOCHEMICAL CHARACTERIZATION OF EACH PEPTIDE

Peptide mediated inactivation at various pHs is tested as follows. The rate of PAI-1 inactivation is tested at every 0.5 pH units over a range of 4.0 to 10.0. This data is correlated with structural stability studies of PAI-1 over the same pH range. Changes in the rate of inactivation at various PHs that correlate with PAI-1 stability indicates that the inherent instability of PAI-1 leads to rapid inactivation, relative to other serpins-peptide systems. No correlation between PAI-1 stability and inactivation rate suggests that the rapid rates of inactivation are unique properties of the peptides chosen. Similar analysis for ionic strength will expand on these data.

Another test of whether the inherently labile nature of PAI-1-1 results in rapid inactivation or if it is a peptide specific phenomenon is to analyze peptide mediated inactivation of other serpins. For these experiments, the inactivation of antithrombin III and α1AT is examined. These serpins have been shown previously to be inactivated by peptides but at a much slower rate that PAI-1 is in our studies (Schulze et al., 1990; Björk et al., 1992). The rate of inactivation is determined exactly as in FIG. 3 except that with antithrombin III the enzyme used is human thrombin, and the substrate S2238 (Kabi), is used to measure the residual thrombin activity. For α1AT the enzyme used is porcine pancreatic elastase and the substrate N-succinyl-L-Ala-L-Ala-L-Ala-p-nitroanilide. A rapid rate of inactivation by our peptides indicates that the efficiency of the peptides is intrinsic to the peptides themselves. Little or no inactivating activity toward these enzymes means that the unstable nature of PAI-1 results in increased sensitivity to peptide mediated inactivation.

To more closely examine the structural requirements of the peptides, a limited set of peptides based on the existing wild-type sequence is constructed with single substitutions at the either first or second position. These peptides are tested for their ability to inactivate PAI-1. The first set consists of the wild-type sequence except that the Thr at the N-terminus will be replaced with either Val, Asp, Asn, or Leu. These N-terminus variations show whether size or charge at the first position effects inactivation. The second set consists of the same residue substitutions except that the second position Val is now replaced. These later studies demonstrate some of the structural requirements for peptide insertion.

EXAMPLE 8

NMR STUDIES OF THE PAI-1 INACTIVATING PEPTIDES

A predominate structure of the inactivating peptides, such as a tendency to form β-sheet structure, can be determined by NMR. The effects of pH and ionic strength on peptide structure can also be examined by this technique. NMR data can then be correlated with functional characterizations under similar conditions (see above). Peptides can also be synthesized with stable isotopes substitutions. Initial experiments use $^{15}N$ to determine intermolecular distances between different $^{15}N$ substituted residue pairs. $^{13}C$ containing peptides are also examined. These analyses yield additional structural data on the peptide conformation when associated with PAI-1.

EXAMPLE 9

CONSTRUCTION AND SCREENING OF COMBINATORIAL SYNTHETIC PEPTIDE LIBRARIES

This invention discloses five peptides that inactivate PAI-1 with significantly greater efficiency than previously reported serpin-peptide systems (Schulze et al., 1990; Björk et al., 1992). However, it is possible that more efficient inactivating peptides may be identified. Two approaches can be utilized to identify peptides with potency for inactivating PAI-1. One involves construction and screening of combinatorial random synthetic peptide libraries (Andrews et al., 1994a; Andrews et al., 1994b). Such systems have been previously used successfully to create peptides that inhibit the binding of monoclonal antibodies, bind to receptor-like molecules, and to create novel bactericidal peptides (Lam et al., 1991; Houghten et al., 1991). These libraries can be synthesized using a multiple peptide synthesis (MPS) approach (Andrews et al., 1994).

Screens for peptides that inactivate PAI-1 utilize a library of non-acetylated peptides based on the existing wt8-mer peptide (SEQ ID NO: 2). The lack of acetylation at the N-terminus aids in identification of PAI-1 associating peptides (see below). However, before the library is created, the wt8-mer (SEQ ID NO: 2) and wt14-mer (SEQ ID NO: 1) peptides can be synthesized without acetylation and tested for inactivation of PAI-1 as above. If the non-acetylated peptides do not inactivate PAI-1, then an acetylated library will be created.

The first library synthesized will be anchored by the wild-type C-terminal residues Ser-Ser-Thr-Ala, with the first four residues substituted with an equal mixture of all 20 amino acids, yielding the sequence Xxx-Xxx-Xxx-Xxx-Ser-Ser-Thr-Ala. This results in 160,000 possible peptide combinations.

Once the library has been synthesized and characterized (Andrews et al., 1994), it is screened. The screen focuses on identifying peptides that react rapidly with PAI-1 at low peptide concentrations (i.e. peptides that would present the best chance of providing useful therapeutic reagents). Briefly, fully active recombinant PAI-1 (1 μM) is reacted with 10% of the peptide library, at a total peptide concentration of 2.5 mM, for 30 min at 37° C. The PAI-1 is then separated from the majority of unbound peptide by precipitation with 50% saturated ammonium sulfate (SAS). After several washes with 50% SAS, the PAI-1 is resolubilized in 1 ml phosphate buffered saline (PBS), and subjected to size fractionation on Sephadex G50 to remove the remaining unbound peptides. The resulting excluded volume, containing PAI-1 is then extensively dialyzed against PBS to ensure that no unbound peptide remains. After dialysis, the PAI-1 is denatured with trifluoroacetic acid to liberate the bound peptides, and this mixture separated by reverse phase HPLC. Since the peptides are likely to be present in low concentrations and since different peptides are likely to elute at different points in the gradient, all fractions not containing PAI-1, will be combined into 4 pools and dried under vacuum. The peptide containing fractions are then subjected to N-terminal sequence analysis. Since the scale of peptide synthesis is 0.25 mmol, the resulting library contains approximately 1 nmol of every possible peptide combination. By using 10% of the library in the screen, 100 pmol of each peptide is added altogether. Currently, the level of sensitivity for this N-terminal sequence analysis is approximately 1 pmol for peptides. Therefore, if 1% of a specific peptide reacts with PAI-1, its sequence can be determined. However, certain factors lessen this degree of sensitivity for a number of reasons. First, the time of incubation limits the amount of peptide that can react, or other peptides in the mixture interfere with the reaction. Therefore, sometimes it is necessary to extend the time that peptides are permitted to react with PAI-1 in order to obtain sequence data. Sometimes, it is not possible to obtain sequence data if peptide concentrations are too low. If this occurs, a new library is synthesized that only randomizes the first three residues (Xxx-Xxx-Xxx-Ser-Ser-Ser-Thr-Ala). This should improve theoretical sensitivity by over 30-fold, since 10% of the library contains 3.1 nmol of each peptide.

While it is reasonable to assume that only a small subset of peptides will react with PAI-1 rapidly enough to be captured in our assay, it is also very unlikely that this subset will consist of only a single peptide. Therefore, the sequence analysis may be complicated by the number of sequences observed. However, it is expected that the rapidly reacting peptides will likely represent only a few sequences. Therefore, in order to establish the correct sequence of each peptide, small sublibraries can be created based on the data obtained in the original screen. In these sublibraries, one of the variable residue positions can be held constant, containing one of the residues identified in the screen, as the other three positions are varied. However, this variability is confined to amino acids identified in the original screen. In this way the linear connectivity of the rapidly reacting peptides can be deduced.

Another potential problem arises if the solubility of some peptides is significantly less than others, since this could bias the screen towards more soluble peptides. While increased solubility is desired, increased solubility might result in missing some very effective peptides. Therefore, a second library is synthesized identical to the first, except that the C-terminal Ala residue will be replaced with Lys (Xxx-Xxx-Xxx-Xxx-Ser-Ser-Thr-Lys). This enhances the solubility of all the peptides and helps to eliminate bias against very hydrophobic peptides. In addition, experience with different 8-mer peptides suggests that residues C-terminal of P13 are less critical in determining peptide reactivity (FIG. 2). Thus, it is likely that these peptides will retain reactivity toward PAI-1.

Finally, if the non-acetylated peptides do not react with PAI-1, then acetylated libraries can be created and reactive peptides isolated as above. In this case, only libraries with the first three residues randomized are used. Mass spectrometry accurately identifies the residues present in a peptide, however the order of the residues is not apparent. Therefore, by limiting the randomization to only three positions, sensitivity is enhanced and the number of additional peptides that will need to be synthesized to determine connectivity is decreased.

Once the optimal amino-terminal residues are identified, new libraries can be created that utilize these residues and randomize the C-terminal amino acids. In this way, the optimal 8-mer peptide can be identified. Finally, a 14-mer library can be created using the best 8-mer sequence identified and randomizing the remaining residues.

EXAMPLE 10

PHAGE DISPLAY OF RANDOM PEPTIDES

A second approach for identifying more efficient PAI-1 inactivating peptides is to utilize a bacteriophage display of random peptide sequences. Phage display involves creating libraries of filamentous phage, similar to the common M13 phage, that display unique polypeptide sequences on their surface. Libraries are constructed by inserting DNA coding for the desired polypeptide into one of the coat protein genes of a phage. The inserted DNA is then expressed as a fusion protein on the surface of phage particles (Smith et al., 1993). By randomly mutating the inserted DNA segment, a library containing a large number of degenerate, or random, polypeptide sequences can be produced at very high titer. If the recombinant phage are also constructed to remain infective, then by alternate rounds of selection and amplification (panning) it is possible to rapidly enrich for high affinity ligand binding sequences.

One recent example of this reported isolation of a high affinity peptide antagonist for the urokinase receptor (Goodson et al., 1994). Similar systems have also been used to identify other novel peptide sequences that bind specific ligands (Goodson et al., 1994; Devlin et al., 1990; Blond-Elguindi et al., 1993; Matthews et al., 1993; Schatz, 1993), as well as for random mutagenesis analysis of existing proteins (Lowman et al., 1991; Hogrefe et al., 1993; Rebar et al., 1994; Roberts et al., 1992). One advantage of phage display over synthetic peptide libraries is amplification. Since the sensitivity of direct protein sequencing requires pmol amounts of a synthetic peptide in order to acquire data, then the size, and therefore the depth of a library must be restricted. In contrast, a single phage particle, containing its own DNA, can be amplified biologically many orders of magnitude. Thus, the depth of a library can be virtually unlimited.

In the present invention, two phage display libraries expressing random peptides on their surface are used. The phage, fUSE5, are based on the Ff class of filamentous phage, and contain inserts coding for random 6-mer or random 15-mer peptides as fusions with the phage pIII protein (Smith et al., 1993). The original library contained approximately $3 \times 10^{11}$ independent phage. Therefore, in the 6-mer library there is an almost 5000-fold over representation of possible sequences. However, since there are approximately $3 \times 10^{19}$ possible 15-mer combinations, this latter library contains only a subset of the potential peptide combinations. Nonetheless, $3 \times 10^{11}$ amino acid combinations provides a sufficiently deep library for the screens used herein.

Several different panning methods are used to identify phage that bind PAI-1. For most of these studies immunoaffinity purified anti-PAI-1 antibodies are coupled to Sepharose, and used to capture the PAI-1 phage complexes. The phage library are first precleared against the anti-PAI-1 Sepharose in the absence of PAI-1. In this way, only phage that specifically bind PAI-1 are selected. In the first screen, phage that block the ability of PAI-1 to form stable complexes with tPA are isolated. Briefly, fully active PAI-1 (Lawrence et al., 1994) is added to the precleared phage library at slightly acidic pH, and allowed to react for two hours. At this pH the conversion of PAI-1 to the latent conformation is very slow (Lindahl et al., 1989). Next, tPA coupled to Sepharose is added, and the sample incubated for an additional 30 minutes to permit formation of PAI-1-tPA complexes. These can then be removed by low speed centrifugation. The remaining PAI-1, which does not react with the tPA, is then be immunoprecipitated with the anti-PAI-1 Sepharose. The associated phage is then eluted off with 6M urea pH 3.0, followed by neutralization of the eluate with 2M Tris (Goodson et al., 1994). The eluted phage yield is then titered and amplified as plaques on bacterial lawns. This process is repeated for four rounds after which 24 individual plaques are isolated, grown as pure phage and then characterized for their effects on PAI-1 activity. The ability of phage to inactivate PAI-1 and the nature of this inactivation is determined by kinetic assays of PAI-1 inactivation and by SDS-PAGE analysis.

Single stranded DNA is also prepared from all phage that demonstrate significant PAI-1 inactivating potential. Then, DNA sequence analysis identifies the peptide sequence. This panning scheme recovers only phage that bind to, and inactivate PAI-1, or phage that bind to previously inactivated PAI-1. This latter situation proves to be a problem if the affinity of phage for inactive PAI-1 is greater than the affinity of the PAI-1 inactivating phage. Therefore, if few or none of 24 selected phage inactive PAI-1, an alternative approach is instituted. This entails taking the amplified phage stock, following the first round of selection described above, and dividing it into two subsets. The two subsets are then subjected to an additional round of preclearing against PAI-1 that has been inactivated with either the wt8-mer or wt14-mer peptides in each subsequent panning round. These additional preclearing steps most likely eliminate the selection of phage that bind PAI-1 only after its inactivation.

A second panning approach is undertaken to identify phage that bind to only active PAI-1. While these phage may not specifically identify peptides that inactivate PAI-1, they may yield useful ligands for distinguishing the active PAI-1 conformation. In addition, this screen might also potentially identify reversible inhibitors of PAI-1 function. For this study, phage is first precleared against pure latent PAI-1 (Lawrence et al., 1994a). Currently latent PAI-1 can be purified to approximately 98%, with about 2% active PAI-1. However by treating this sample with catalytic amounts of elastase, the active PAI-1 is completely eliminated (Lawrence et al., 1994a). The conformation of elastase cleaved PAI-1 is similar to latent PAI-1 in that its reactive center loop is fully inserted into β-sheet A (Lawrence et al., 1994a). Thus, by incubating the phage library with elastase treated latent PAI-1 followed by anti-PAI-1 immunoprecipitation, any phage particle that binds to latent PAI-1 is removed.

The phage stock can then be reacted with fully active PAI-1 and the phage recovered and amplified as above. Again, 24 phage can be selected and isolated as purified clones after the fourth round of panning. The isolated phage is tested for their ability to bind both latent and active PAI-1. For this assay phage is partially purified by polyethylene glycol precipitation (Sambrook et al., 1989), and an ELISA-based assay is used to detect specific PAI-1 binding (Smith et al., 1993). The purified phage is allowed to bind to microtiter plates overnight, then blocked with BSA, and either active or latent PAI-1 samples are added. Bound PAI-1 is detected with affinity purified, biotinylated, rabbit anti-PAI-1 antibodies followed by streptavidin conjugated to alkaline phosphatase (Sherman et al., 1992). Phage that demonstrate significant binding to active PAI-1 in this assay is then characterized by DNA sequence analysis.

These phage are also tested for their ability to block PAI-1s inhibitory activity against uPA and tPA, both as PAI-1 inactivators and also as reversible competitive inhibitors of PAI-1 activity. Any phage that are shown to inhibit PAI-1 activity can also be characterized for their ability to induce substrate behavior. These phage can also be tested for their ability to inactivate antithrombin III and α1AT as described above. Finally, all phage can be characterized for their ability to block PAI-1 binding to vitronectin. For this analysis PAI-1 will be preincubated with each phage followed by a vitronectin specific ELISA (Lawrence et al., 1994a).

In addition to the inactivation of PAI-1 on fibrin clots and in circulating blood, there may be a significant therapeutic advantage to disrupting PAI-1 function within the subendothelial matrix. One recent study has linked the lack of plasmin activity in this compartment to the proliferation of smooth muscle cells (Grainger et al., 1993). Such proliferation is thought to be a major cause of restenosis following angioplasty (Cercek et al., 1991). Consequently, enhancing plasmin activation within the subendothelium, by inactivating or displacing PAI-1, may provide a useful adjuvant therapy, following angioplasty, to help prevent restenosis. Therefore, in addition to testing the phage identified above for their ability to block vitronectin binding, a specific screen is developed for this end.

For these studies the phage library is first precleared against anhydrotrypsin-Sepharose in addition to anti-PAI-1 Sepharose. Phage that block vitronectin binding are selected by coating native vitronectin onto 10 cm plastic tissue culture dishes, followed by blocking with 3% BSA. Simultaneously, PAI-1 is incubated with the phage library.

Next the PAI-1-phage solution are added to the vitronectin-coated plate and allowed to react for 1 hr. The supernatant is then be removed and reacted with anhydrotrypsin Sepharose for 1 hr. Anhydrotrypsin binds active PAI-1 (Lawrence et al., 1994c) but should not bind to latent PAI-1. This step is necessary since our previous data has shown that latent PAI-1 does not associate with vitronectin (data not shown). Therefore, in order to eliminate phage that block the PAI-1-vitronectin association via conversion of PAI-1 to the latent conformation, only PAI-1 that does not adhere vitronectin but retains the protease binding conformation is selected (Lawrence et al., 1994c).

In addition, a second approach that seeks to identify peptides that can disrupt a preformed PAI-1 vitronectin complex is also examined. This approach uses the same double, negative/positive selection except that the PAI-1 is allowed to bind to vitronectin before phage are added. Both of these systems are carried through 4 rounds of panning and then independent phage isolated as above. These are tested for specific binding to PAI-1 in the ELISA described above and for the ability to block vitronectin binding. The peptide sequence of all positive clones can then be determined by DNA sequencing.

Once PAI-1 binding phage have been identified in each of the screens above, the 5 most efficient peptide sequences derived from each scheme are produced as free synthetic peptides in order to compare their efficacy relative to the original peptide samples.

As discussed at the beginning of this section, phage display has many advantages over synthetic peptide libraries. However, one potential disadvantage is that each of the peptides expressed on phage are produced as fusion proteins. If the most efficient PAI-1 inactivating peptides require a free N- or C-terminus, then it is likely that phage display fails to identify these candidates. Therefore since both systems have relative advantages and disadvantages, utilizing both strategies presents the best opportunity of identifying improved PAI-1 inactivating peptides.

EXAMPLE 11

DEVELOPMENT OF PEPTIDE PRODUCING VECTORS FOR PAI-1 INACTIVATION IN VIVO

Peptide mediated inactivation of PAI-1 in vivo is a potential treatment of pathological thrombosis. Therefore, peptides identified in this study are expressed in cell culture and tested to see if they retain the ability to inactivate PAI-1 or block vitronectin binding. Eucaryotic expression vectors are constructed where sequences coding for the most efficacious peptides are expressed as fusions proteins. The proteins chosen as carriers for the peptides are selected to target the PAI-1 binding peptides into distinct compartments in vivo. The expression constructs are then transiently transfected into cells in culture and tested for their ability to produce PAI-1 inactivating peptides.

The vector system chosen is based on the expression plasmid pMT2 (Sambrook et al., 1989). The first fusion protein tested consists of the secretion signal sequence of PAI-1, followed by sequences coding for the influenza hemagglutinin epitope recognized by the monoclonal antibody 12CA5 (Kolodziej et al., 1991). These sequences are fused in frame to the coding sequence for fibronectin finger domains 4 and 5, followed by the sequence coding for best PAI-1 inactivating peptide. The PAI-1 secretion signal sequence is constructed directly in the pMT2 vector by cassette mutagenesis (Lawrence et al., 1989). The fibronectin sequences are produced by PCR reactions using the fibronectin cDNA as template. The 12CA5 epitope sequences are included the 5' fibronectin PCR primer, and the PAI-1 inactivating peptide coding sequences in the 3' fibronectin PCR primer. The inclusion of the 12CA5 epitope permits monitoring fusion protein expression by immunoblot analysis (Kolodziej et al., 1991). The fibronectin fingers 4 and 5 are chosen for two reasons. First they are independently folded domains, that have previously been expressed as recombinant proteins (Novokhatny et al., 1994). Consequently, it is likely that the fusion proteins are efficiently expressed. Secondly, these domains together comprise the N-terminal fibrin binding site of fibronectin (Matsuka et al., 1994). The fibrin affinity of the fusion protein targets the peptide to the fibrin surface. If the fibronectin fusions are not expressed efficiently or fail to target the peptide to fibrin, then a second construct can be produced fusing the same 12CA5 epitope and PAI-1 inactivating peptide to the plasminogen kringle 1. This domain of plasminogen also binds to fibrin, however its interaction is thought to be primarily through the lysine binding site (Menhart et al., 1991). Like the fibronectin finger domains, kringles are thought to be independently folded units and a number of them have previously been expressed using recombinant technology (Menhart et al., 1991; Menhart et al., 1993; de Serrano et al., 1993; de Serrano et al., 1992).

This construct can also be produced by PCR and include the secretion signal sequence of PAI-1. If each of these constructs fail to express protein or do not bind to fibrin, then both constructs can be reengineered to place the 12CA5 epitope at the C-terminus immediately preceding the PAI-1 inactivating peptide. With these four options it is likely that efficient expression will be achieved.

The constructs are then transiently transfected into COS 7 cells and protein expression monitored by western blot analysis of the culture supernatant with the 12CA5 antibody (Kolodziej et al., 1991). If expression is observed, then the ability to inactivate PAI-1 is examined by treating purified PAI-1 with the culture supernatant and looking for loss of PAI-1 activity. To test for fibrin binding, human fibrinogen is added to microtiter plates and clotted with thrombin. The plates are then blocked with BSA and the culture supernatant added. Binding of the fusion protein is then detected with the 12CA5 antibody followed by a goat anti-murine IgG conjugated to alkaline phosphatase. The peptides that block vitronectin binding are then examined by incubating the culture supernatant in the PAI-1 vitronectin ELISA (Lawrence et al., 1994a), and loss of PAI-1 binding is monitored.

An additional peptide fusion construct is produced fusing the PAI-1 secretion signal sequence followed by the 12CA5 sequence to a truncated form of the heparin binding growth factor, acidic fibroblast growth factor (aFGF) followed by the PAI-1 inactivating peptide. This truncated form of aFGF, lacking the first 27 residues appears to have little mitogenic activity but retains very tight heparin binding (Burgess, 1991). This heparin binding activity has been linked to the association of aFGF to the subcellular matrix (Burgess, 1991). This construct is expressed as above and characterized in the same way except that heparin coated microtiter plates is used instead of fibrin. If the construct produces functional peptide fusions then its high heparin affinity may target the inactivating peptides to the subendothelial cell matrix.

Finally, one other construct is produced fusing the 12CA5 epitope and the PAI-1 inactivating peptide to a cell surface protein. Respiratory syncytial virus glycoprotein G (RSVG) (Wertz et al., 1985) is an integral membrane protein that has been used previously to express fusion peptides on the surface of a cell (Vijaya et al., 1988). The 12CA5 epitope and PAI-1 inactivating peptide sequences are ligated to the 3' end of RSVG cDNA and cloned into pMT2 as above. Transient transfections are performed and protein expression analyzed by western blotting of cell extracts and by immunofluoresence of whole cells. If expression is successfully demonstrated, then the ability to inactivate PAI-1 is examined by adding PAI-1 to cell cultures, incubating for one hour and then removing the supernatant and assaying for residual PAI-1 activity.

The expression of PAI-1 inactivating activity on the cell surface together with the other targeted peptide constructs just described suggests future experiments aimed at introducing transient expression of similar PAI-1 inactivating peptide constructs in vivo as a limited gene therapy approach directed at temporarily increasing the local fibrinolytic potential. Such therapies would likely enhance and complement current interventions for pathologic thrombosis.

EXAMPLE 12

PLASMINOGEN ACTIVATOR INHIBITOR (PAI-1) AND THROMBOLYSIS RESISTANCE

Molecular Genetic Analysis of PAI-1 Deficiency:

In order to define how PAI-1 participates in the pathogenesis of human disease, the clinical characteristics and molecular defect of an Old Order Amish pedigree with PAI-1 deficiency has been characterized (Fay et al., 1992). The proband was a nine year old girl with a moderate bleeding disorder present since birth. Although an extensive hemostatic evaluation was negative, she eventually was found to have elevated concentrations of free t-PA in plasma and no detectable PAI-1 in either her plasma or platelets. The polymerase chain reaction (PCR) was used to sequence the PAI-1 promoter, coding sequence, and all intron-exon junctions. The proband was found to be homozygous for a frame-shift mutation (2 bp insertion) in exon 4, which resulted in premature stop codon formation. Both parents were heterozygous for this mutation.

Analysis of platelet RNA amplified from the proband's parents by reverse transcription and PCR suggested that this mutation results in the synthesis of an unstable PAI-1 mRNA. In addition, analysis of recombinant mutant PAI-1 expressed in *E. coli* revealed that it was truncated and inactive. Hence, the proband represents the first report of complete PAI-1 deficiency in humans. Her siblings, several relatives, and a group of non-relatives were also genotyped, and to date 11 heterozygotes have been identified. None of the heterozygotes exhibits abnormal bleeding, suggesting that a single normal PAI-1 allele is sufficient for normal hemostasis.

Since enhanced PAI-1 expression is associated with myocardial infarction (Hamsten et al., 1985), it is possible that heterozygous PAI-1 deficiency might be cardioprotective. If this mutation is present with sufficient frequency in the Old Order Amish population, it may be possible to test this hypothesis by correlating PAI-1 genotype and cardiac events. To date, we have screened more than 60 Old Order Amish individuals for the presence of the exon 4 mutation by allele-specific oligonucleotide (ASO) hybridization, and additional screenings are planned.

Figure 7A:
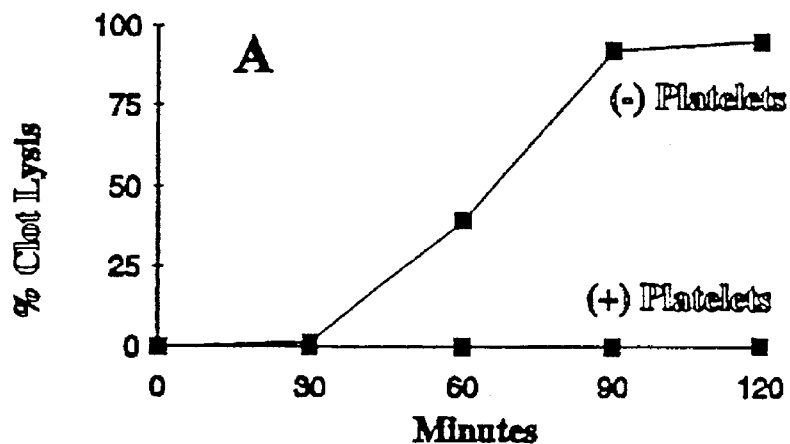
FIG. 7a shows the lysis of clots in the presence and absence of platelets which provides PAI-1.

Platelet PA-1-1 and Thrombolysis Resistance:

The identification of a patient with complete deficiency of PAI-1 offers a unique opportunity to assess the role of this protein in the resistance of platelet-rich thrombi to lysis. PAI-1 is present in platelet α-granules and is released upon platelet activation. Therefore, if PAI-1 contributes to the inhibitory effects of platelets on clot lysis, one would predict that clots containing platelets of the proband would lyse more readily than clots containing normal platelets. To test this hypothesis, an in vitro clot lysis assay consisting of fluorescein-labeled fibrinogen (1 mg/mL), glu-plasminogen (20 µg/mL), thrombin, and t-PA (2 ng/mL) was utilized (Fay et al., 1994). In this system, clot lysis, which is monitored by release of fluorescein-labeled fibrin degradation products, is >90% complete after 60 min at 37° C. However, addition of washed human platelets ($2.5 \times 10^8$/mL) results in a marked inhibition of clot lysis, with less than 2% clot lysis occurring by 120 min (FIG. 7a).

Figure 7B:
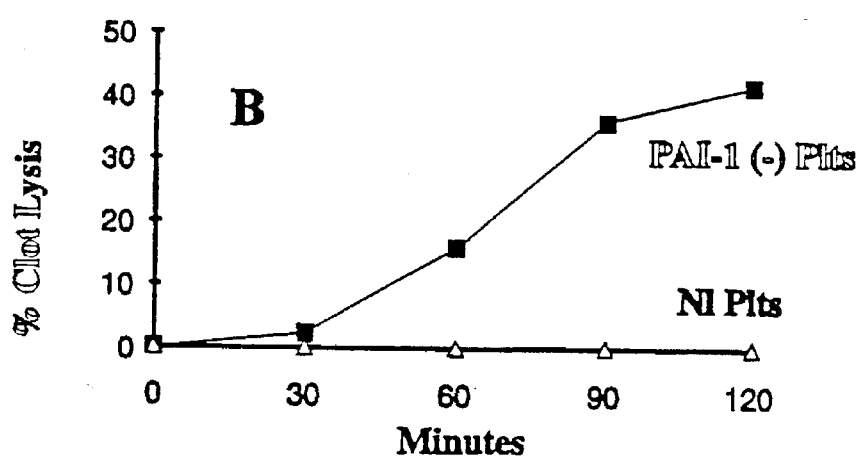
FIG. 7b shows the effects of exposing a clot to platelets derived from a patient with complete PAI-1 deficiency.

The effects of washed platelets obtained from the patient with complete PAI-1 deficiency were compared to those obtained from a normal control (FIG. 7b). Whereas essentially no lysis occurred by 120 min in the control reaction, 41% clot lysis was observed in the presence of PAI-1-deficient platelets. In similar experiments, clot lysis was allowed to occur for 60 min in the presence of varying concentrations of normal or PAI-1-deficient platelets. For both normal and PAI-1-deficient platelets, a concentration-dependent inhibition of clot lysis was noted, though more extensive lysis consistently was observed in the presence of PAI-1-deficient platelets.

These results suggest that PAI-1 contributes significantly to the inhibitory effect of platelets on clot lysis, but also suggest that PAI-1-independent mechanisms are important in mediating clot lysis resistance. These PAI-1-independent mechanisms may represent clot retraction, which was observed in our experimental system, interaction of fibrin with the platelet surface, or platelet release of α2-antiplasmin and factor XIII (Fay et al., 1994). The above results also suggested that plasminogen activators that are resistant to inhibition by PAI-1 should exhibit enhanced efficiency in lysing platelet-rich clots.

To test this hypothesis, a mutant t-PA that is highly resistant to inhibition by PAI-1 (Madison et al., 1990) was used to lyse clots containing normal platelets. As predicted, the mutant t-PA was much more effective than wild-type t-PA. Conversely, no significant differences were observed when comparing the capacity of the mutant t-PA to dissolve clots containing platelets with absent vs. normal PAI-1 content.

Concentration of PAI-1 in Porcine Coronary Artery Thrombi:

Although platelet PAI-1 inhibits fibrinolysis in vitro, the role of PAI-1 in regulating the lysis of platelet-rich clots formed in vivo is unknown. The magnitude of a PAI-1 effect should be dependent upon the concentration of PAI-1 present in platelet-rich thrombi, which may be substantially higher than the concentration of PAI-1 in clots formed in vitro. To address this issue, an animal model of acute coronary thrombosis was utilized. In collaboration with Drs. Joseph Murphy and Robert Schwartz of Mayo Clinic, platelet-rich coronary thrombi were generated in pigs by balloon catheter-induced arterial injury (Murphy et al., 1992). Extracts were prepared from 5 thrombi by homogenizing them in the presence of 9 volumes of 0.02M Tris-HCl, pH 8.0, containing 0.05% 2-mercaptoethanol, and 50 KIU/mL aprotinin, then centrifuging the suspension.

The supernatant ("thrombus extract") was assayed for PAI-1 content, from which the concentration of PAI-1 in the original thrombus was calculated. PAI-1 activity in thrombus extracts was measured by a urokinase inhibition assay in which serial dilutions of each thrombus extract were incubated with urokinase, and residual enzyme activity was used to determine PAI-1 concentration. The mean PAI-1 content of 5 thrombi was 36±5 µg/mL.

A previously described immunoactivity assay (which utilizes an anti-PAI-1 polyclonal antibody to detect PAI-1 bound to immobilized t-PA (Fay et al., 1992) was also used to measure PAI-1 antigen in 2 of 5 thrombi, with results of 28 and 29 µg/mL. Purified porcine PAI-1 (specific activity 425,000 U/mg) was used as standard for these experiments. In contrast, the concentration of PAI-1 in pooled porcine plasma was <20 ng/mL. Of note, this assay detects only active PAI-1 antigen. Consistent with this, preincubation of thrombus extracts with a molar excess of t-PA resulted in loss of detectable PAI-1 in the immunoactivity assay. In addition, autoradiography revealed that SDS-stable complexes indistinguishable from PAI-1-urokinase complex rapidly formed upon incubation of thrombus extracts with $^{125}$I-urokinase.

Hence, high concentrations of active PAI-1 are present in coronary thrombi generated in pigs. Given the composition of these thrombi, their PAI-1 content presumably is of platelet origin. Platelets contain sufficient PAI-1 (4000–8000 molecules per cell) to account for the concentrations of inhibitor detected in coronary thrombi (Sprengers et al., 1986). However, the vast majority (95%) of PAI-1 in washed human platelets exists in an inactive form, and studies by Lang et al. suggest that the specific activities of porcine and human PAI-1 are similar (Lang et al., 1992).

It is possible that the environment of the coronary thrombus may retard the conversion of PAI-1 from active to latent, or convert latent inhibitor to active. Studies by Vaughan et al. suggest that conversion of latent PAI-1 to active can occur in vivo (Vaughan et al., 1990). Platelets also contain relatively large amounts of vitronectin, which binds and stabilizes PAI-1 in the active conformation (Preissner et al., 1989). In addition, phospholipid vesicles reactivate latent PAI-1 in vitro, suggesting that conversion of latent PAI-1 to active may occur on the platelet surface (Lambers et al., 1987). Alternatively, it is possible that vascular cells at the site of arterial injury, either endothelial or subendothelial, secrete significant amounts of active PAI-1 into the forming thrombus, as has recently been clemonstrated in vitro (Handt et al., 1994). This hypothesis is supported by reports that factors released by activated platelets, including transforming growth factor-β and platelet-derived growth factor, stimulate vascular endothelial and smooth muscle cells to secrete PAI-1 (Fujii et al., 1990). Nevertheless, regardless of its origin, these studies indicate that high concentrations of active PAI-1 are present in freshly-formed porcine coronary thrombi.

Augmentation of Fibrinolysis in vitro by a PAI-1-Inhibitory Peptide:

Given that platelet PAI-1 contributes to clot lysis resistance and that coronary thrombi contain high concentrations of PAI-1, then strategies aimed at inhibiting PAI-1 within thrombi will most likely prove useful in augmenting coronary thrombolysis. As mentioned previously, anti-PAI-1 antibodies accelerate the lysis of platelet-rich clots (Levi et al., 1992; Braaten et al., 1993). However, there are several disadvantages associated with the use of antibodies as therapeutic agents (e.g., need for purification, antigenicity, expense), and non-antibody based methods for inactivating PAI-1 are likely to facilitate the application of this strategy to the clinical setting. The use of synthetic peptides represents an attractive alternative. Prior studies with other serpins α1-antitrypsin and antithrombin III) indicated that synthetic 14 amino acid peptides based on a series of residues (P1-P14) within the reactive center "loop" of each protein can bind to the respective serpin and inactivate it (Schulze et al., 1990; Björk et al., 1992). However, the rate of inactivation was quite slow. PAI-1 appears unique among the serpins in that its P1-P14 residues spontaneously insert into this β sheet, thereby inducing an inactive, or latent, conformation. This suggested that an analogous peptide based upon residues P1-P14 of PAI-1 (i.e., amino acid residues 356–369=Thr-Val-Ala-Ser-Ser-Ser-Thr-Ala-Val-Ile-Val-Ser-Ala-Arg, residues) (SEQ ID NO: 1) might more rapidly inactivate PAI-1.

Figure 8A:
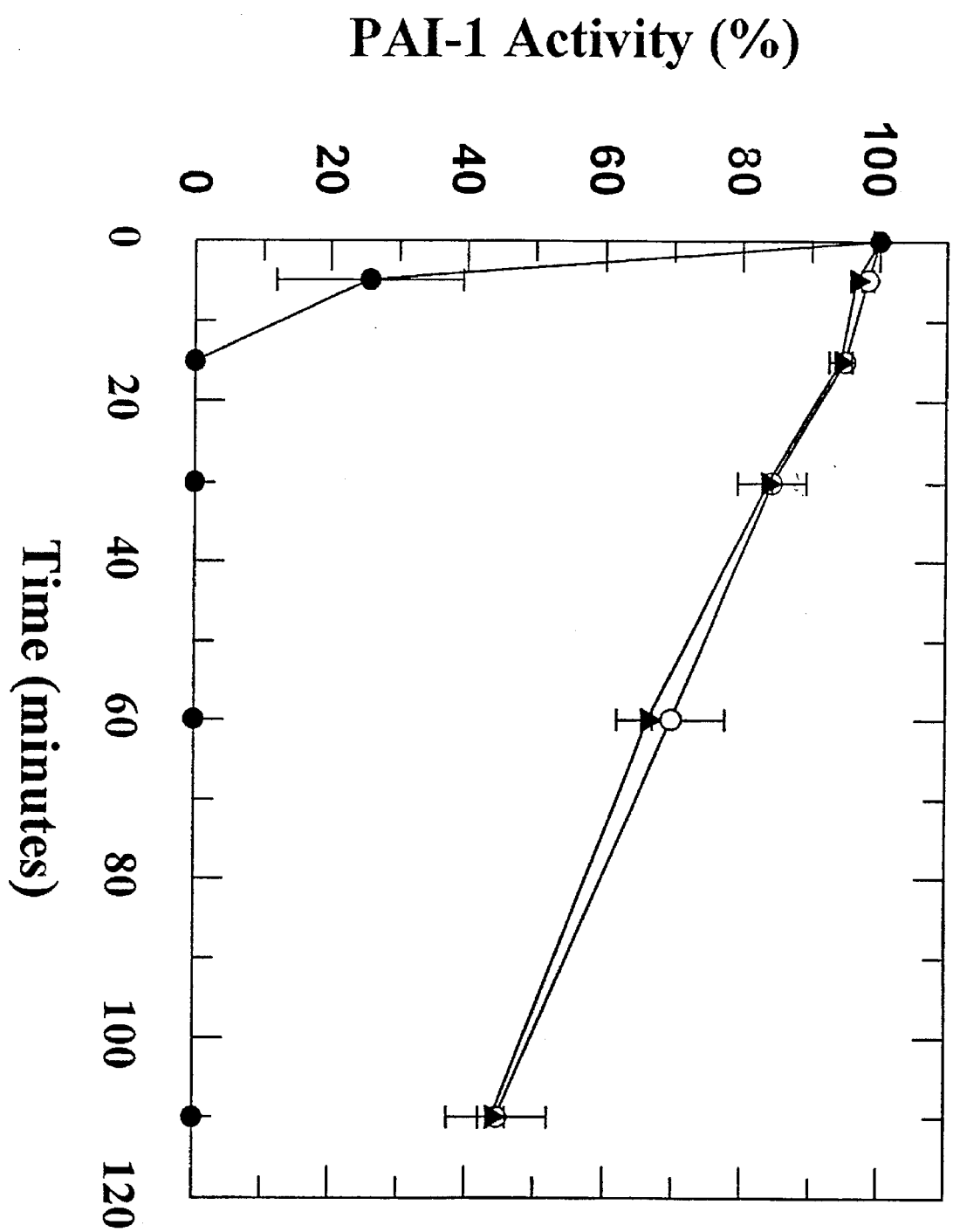
FIG. 8a shows PAI-1 activity in the absence of vitronectin.
Figure 8B:
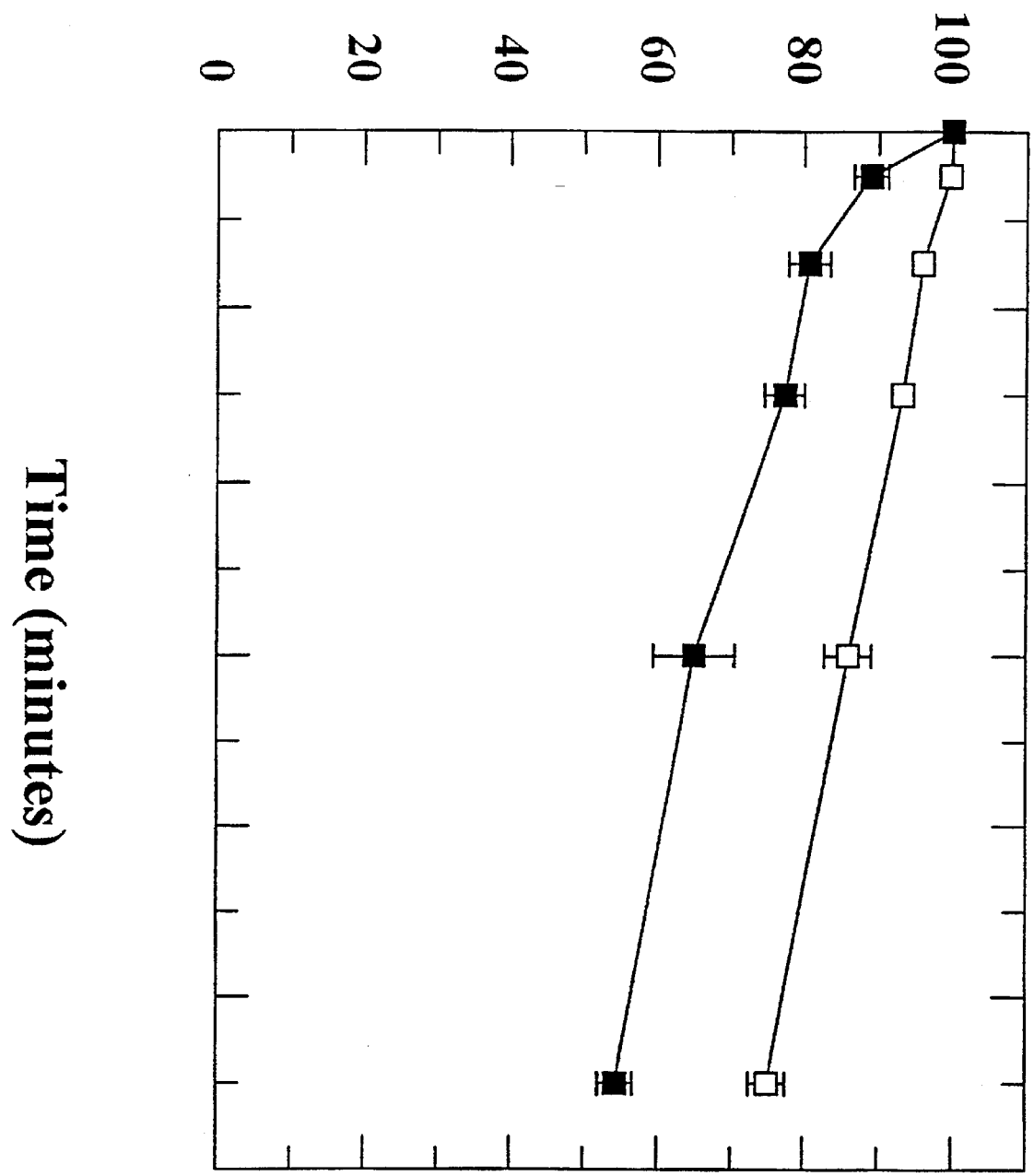
FIG. 8b shows PAI-1 activity in the presence of vitronectin.

Experiments were performed in which PAI-1 was incubated with an 80-fold molar excess of P1-P14 peptide, and the rate of PAI-1 inactivation was determined. In the absence of peptide, PAI-1 half-life at 37° C. was 98±18 min, consistent with data of others (Loskutoff et al., 1989). However, the half-life of PAI-1 was shortened 24-fold in the presence of peptide (i.e., to 4±3 min). A control 14 amino acid peptide lacking PAI homology had no effect on PAI-1 half-life (FIG. 8a). Since vitronectin (a protein present in plasma, platelets, and the extracellular matrix) binds and stabilizes PAI-1, the capacity of P1-P14 peptide to inactivate vitronectin-bound PAI-1 was assessed. In contrast to experiments with free inhibitor, PAI-1 bound to vitronectin was only slowly inactivated by the peptide (FIG. 8b). Similarly, P1-P14 peptide inhibited complex formation between free PAI-1 and t-PA (determined by SDS-PAGE), but not between vitronectin-bound PAI-1 and t-PA.

The capacity of P1-P14 peptide to accelerate fibrinolysis in vitro, both in the absence and presence of platelets was also evaluated. Fluorescein-labeled fibrin clots were formed in the presence of recombinant PAI-1 (0.7 μM) and either P1-P14 peptide (55 μM), an irrelevant 14 amino acid peptide (55 μM), or no peptide. After 30 min at 37° C., fibrinolysis was initiated by the addition of t-PA (20 nM), and % clot lysis was determined 60 min later. Addition of P1-P14 peptide increased clot lysis from 28±7% to 90±6% (mean±SEM of triplicate experiments), whereas the control peptide had no effect on clot lysis either in the presence or absence of PAI-1 (FIG. 6a). In similar experiments, platelet-rich clots were formed by clotting fluorescein-labeled fibrinogen in the presence of $2.5 \times 10^8$ platelets/mL, and fibrinolysis was initiated by the addition of t-PA (75 pM). The lysis of platelet-rich clots at 90 min was increased from 8±3% to 41±12% by the addition of P1-P14 peptide (FIG. 6b), while the control peptide did not affect clot lysis.

Hence, a synthetic 14 amino acid peptide based upon a portion of the PAI-1 reactive center loop rapidly inactivates PAI-1 and accelerates fibrinolysis in vitro. Of note, platelets contain relatively large amounts of vitronectin (Preissner et al., 1989). Although vitronectin protects PAI-1 from inactivation by P1-P14 peptide, the peptide still enhanced the lysis of platelet-rich clots. It thus appears that sufficient interaction between PAI-1 and P1-P14 peptide can occur within the environment of the platelet-rich clot so as to augment fibrinolysis.

Mouse Fibrinolysis Model:

A murine model of arterial thrombolysis has been established. Human t-PA is used in this model system since large quantities of the recombinant enzyme are readily available. First it was confirmed that human t-PA indeed activates mouse plasminogen. Citrated mouse blood (0.1 mL) was clotted in vitro by addition of thrombin, then t-PA (Genentech) was added in final concentrations ranging from 0.25–1.0 μg/mL. However, no apparent clot lysis (determined visually) was observed. In contrast, 0.25 μg/mL of t-PA completely lysed human blood clots within 30 min. A similar pattern of results was obtained with human urokinase. Therefore, the experiment was repeated after supplementing mouse blood with human glu-plasminogen (final concentration 50 μg/mL). The lysis of these "spiked" murine clots was indistinguishable from that of human clots. This suggests that human t-PA does not activate mouse plasminogen, at least to any considerable extent.

Next, human glu-plasminogen was administered to an adult mouse by tail vein injection in concentrations estimated to acutely raise the level of circulating human plasminogen to 20 μg/mL. After 20 min, 0.1 mL of blood was withdrawn from the animal into citrate anticoagulant. The blood was clotted with thrombin, then t-PA was added (0.5 μg/mL). This clot completely lysed within 15 min, indicating that human plasminogen can be administered to mice, so as to render their fibrinolytic system sensitive to human t-PA, at least for a period of time sufficient for acute experiments. Because of the species dependence of the t-PA/plasminogen interaction, other cross-species interactions of human and mouse fibrinolytic proteins were examined. For example, recombinant murine PAI-1 rapidly forms SDS-stable complexes with human t-PA, suggesting that this interaction is not significantly affected by species. However, kinetic analyses are necessary to confirm this.

EXAMPLE 13

PLATELET-MEDIATED HEPARIN RESISTANCE

Animal Studies:

Platelets contain several factors that inhibit heparin, including platelet factor 4, heparatinase, and histidine-rich glycoprotein. In an attempt to study potential heparin resistance within the microenvironment of the coronary thrombus the coronary thrombi previously analyzed for PAI-1 content were also assessed for their capacity to inhibit heparin in vitro (Eitzman et al., 1994). Pharmaceutical grade, unfractionated heparin was added to normal human plasma in sufficient quantity (0.12 U/mL) to prolong the activated partial thromboplastin time (APTT) to approximately 2× control. APTT determinations were then repeated after the addition of 2.5 μL of thrombus extract per 100 μL of heparinized plasma. This typically resulted in a shortening of the APTT by approximately 20 seconds, whereas thrombus extract had no effect on the APTT in the absence of heparin.

To more precisely quantify the anti-heparin effect of coronary thrombi, the observed shortening of the APTT in response to thrombus extract was compared to a standard curve of APTT vs. heparin concentration. The mean heparin neutralizing capacity of the 3 thrombi analyzed by this method was 28 units of heparin/mL of thrombus. Hence, 1 volume of coronary thrombus can completely inhibit the heparin in 140 volumes of therapeutically anticoagulated plasma (i.e., containing 0.2 U/mL heparin).

Figure 9A:
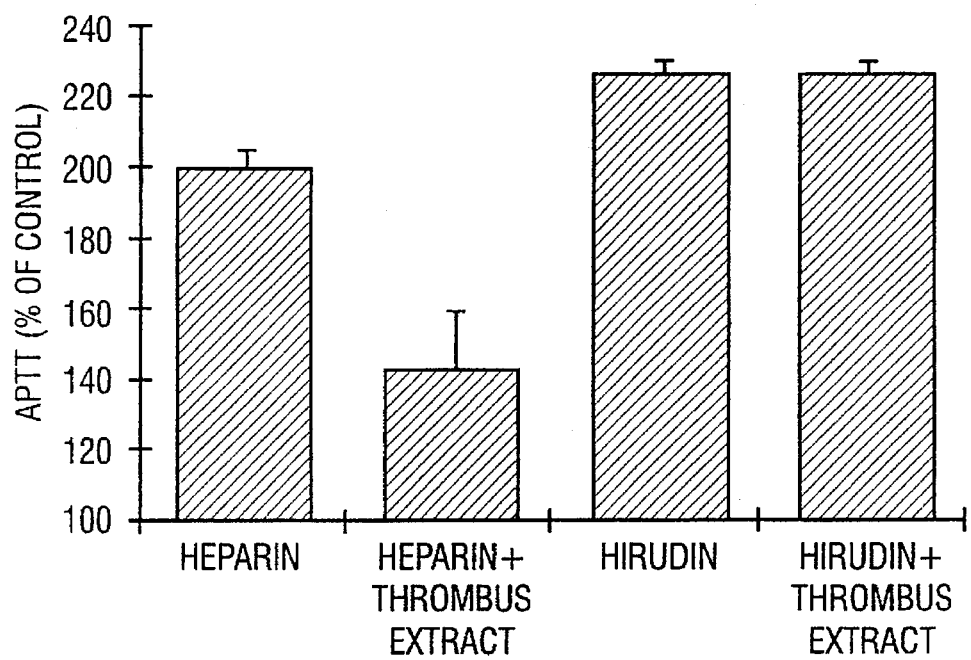
FIG. 9a shows the effect of heparin and hirudin both alone or in combination with thrombus extract on APTT.

Similar experiments were also performed using recombinant hirudin as anticoagulant. In these experiments, hirudin (0.17 µg/mL) was used to prolong the APTT to approximately twice control values. However, unlike the case with heparin, thrombus extracts had no effect on capacity of hirudin to prolong the APTT (FIG. 9a).

Figure 9B:
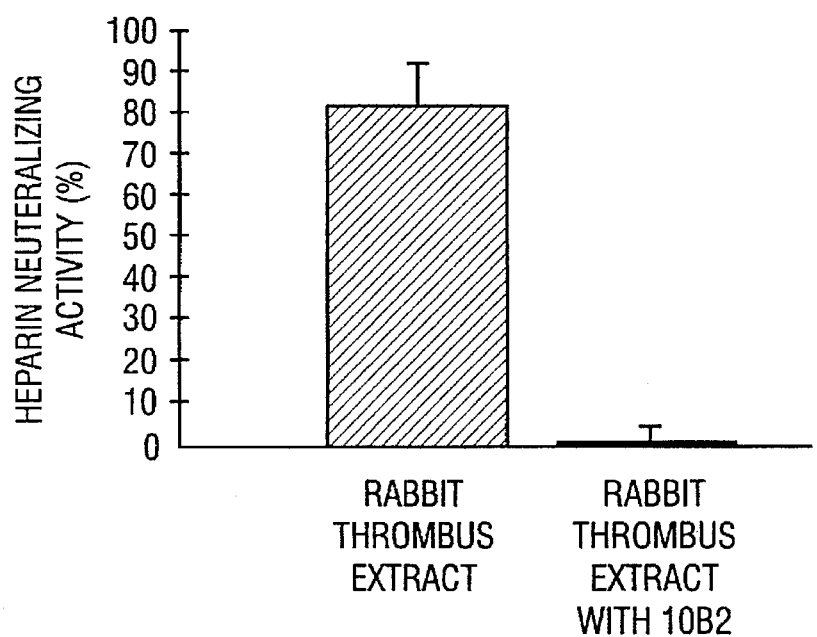
FIG. 9b shows the effect of rabbit thrombus extract alone and in combination with 10B2 on heparin neutralizing activity.

To characterize the antiheparin activity in coronary thrombi, thrombus extracts were incubated with heparin-agarose, and adsorbed extracts were added to the APTT, as described above. This resulted in a marked reduction of heparin neutralizing activity. Therefore, the adsorbed heparin-agarose was serially incubated with 0.4, 0.8, 1.4, and 2.0M NACl, and the resulting eluates were assayed for antiheparin activity. The 1.4M NaCl eluate shortened the APTT by 34 sec, whereas the other eluates had only a minor effect, indicating that the heparin neutralizing activity present in porcine coronary thrombi bound to heparin with high affinity. These results suggested that platelet factor 4 (PF4) may mediate the anti-heparin effect of thrombus extracts. Platelet factor 4 is a 29000 M.W. homotetrameric protein present within platelet alpha-granules. The C-terminus of PF4 contains a lysine-rich segment that binds and inactivates heparin. However, PF4 does not inhibit hirudin. To test this hypothesis, experiments with a monoclonal antibody to rabbit PF4 were performed. This antibody inhibits the anti-heparin effect of PF4 by reacting with its heparin-binding domain (Cazzola et al., 1992). However, this monoclonal antibody did not cross-react with porcine PF4. Therefore, platelet-rich carotid thrombi were induced in rabbits, retrieved, and used to generate thrombus extracts, as described above. As expected, these extracts exhibited potent heparin neutralizing activity. A factor Xa inhibition assay was used to determine the effect of 10B2 on the anti-heparin activity of rabbit carotid thrombi. As shown in FIG. 9b this antibody essentially completely neutralized their anti-heparin activity, suggesting that PF4 (as opposed to other potential platelet proteins) represents the dominant mechanism by which platelets inhibit heparin at sites of arterial injury.

Human Studies:

Elevated plasma levels of PF4 have been detected in some patients with acute coronary artery syndromes (Kaplan et al., 1986). Similarly, Maraganore et al. have reported systemic heparin resistance (defined as a reduced prolongation of the APTT after addition of heparin in vitro) in a small group of patients with acute coronary artery disease (Maraganore et al., 1992). However, as discussed previously, the prevalence, magnitude, and etiology of systemic heparin resistance in this clinical setting are unknown. Therefore, a study of the phenomenon of heparin resistance in patients with acute coronary syndromes was performed.

Citrated blood samples (5 mL) were obtained from patients (n=5) presenting with acute myocardial infarction or unstable angina pectoris. Blood samples were collected before heparin therapy was initiated. The heparin neutralizing activity of patient plasmas was determined in a Factor Xa inhibition assay, and compared to a reference plasma prepared from 4 normal individuals. Heparin neutralizing activity was detected in 3 of 5 patient plasmas, but not in the control plasma. However, the magnitude of heparin inhibition in these 3 patient samples was small (mean 9.4 mU heparin neutralized per mL of patient plasma), and was calculated to be sufficient to inhibit only approximately 5% of the heparin in therapeutically anticoagulated plasma (0.2 U/mL).

EXAMPLE 14

EXPRESSION AND FUNCTIONAL CHARACTERIZATION OF RECOMBINANT STREPTOKINASE

Cloning and Expression of Streptokinase:

In order to characterize the human antibody response to streptokinase (SK), and to use this information to design SK molecules with reduced immunoreactivity. The polymerase chain reaction (PCR) was utilized to clone the streptokinase gene. An approximately 1.2 kb Nde I/BamH I fragment containing the complete SK coding sequence was generated by PCR, using template DNA isolated from S. equisimilus H46A (ATCC). This fragment was cloned into pET3a, then sequenced (to exclude PCR-induced sequence errors). This construct directs the synthesis of mature streptokinase protein (414 amino acids) under the control of the T7 promoter, and allows high-level expression of SK in E. coli strains that express T7 polymerase [e.g., BL21(DE3)pLysS]. Protein production was induced in transformed E. coli by addition of isopropylthio-β-D-galactoside (IPTG), and lysates of pelleted cells were prepared by repeated freeze/thaw cycles. Samples of the lysate supernatant were subjected to SDS-PAGE and Western blotting using an anti-SK monoclonal antibody (American Diagnostica). High levels were SK production were achieved (approx 20 mg SK per liter of bacterial suspension), with SK comprising approximately 50% of total intracellular protein. Lysates of bacterial cells expressing SK readily activated plasminogen, whereas control lysates lacking SK exhibited no activity. Purification of recombinant SK by active-site blocked plasmin-agarose chromatography is currently underway.

Generation of Amino- and Carboxy-terminal Deletion Libraries:

A library of N-and C-terminal SK deletion mutants was generated. This library will likely prove useful in mapping antibody epitopes, and also yield important functional information on SK. To generate nested sets of N-terminal deletions, the SK coding sequence was cloned into pGEM3Zf(−) (Promega), then digested for varying time intervals with exonuclease III and mung bean nuclease, according to the method of Henikoff (Henikoff, 1990). Deletion mutants were repaired with T4 DNA ligase and used to transform BL21 (DE3)pLysS.

To facilitate rapid detection of active deletion mutants, transformed cells were plated on agarose plates containing glu-plasminogen (1 µg/mL) and 1% dry milk (as a source of casein). Clear zones of lysis were detected around clones synthesizing active SK, induced by plasmin formation and digestion of casein (FIG. 6). A potentially high background of wild-type SK clones was prevented by the prior introduction of an Nsi I site immediately 3' to the deletion initiation site, which in this method is targeted by a synthetic oligonucleotide (Henikoff, 1990). Hence, digestion of the deletion library with Nsi I prior to transformations eliminated the wild-type background. To detect inactive, yet in-frame deletions, a filter-based screening strategy was utilized. Transformed colonies (incubated in the presence of IPTG) were transferred to nitrocellulose filters, then subjected to 3 freeze-thaw cycles. The filters were blocked with 3% BSA, then serially incubated with murine anti-SK monoclonal antibody, alkaline phosphatase-conjugated goat anti-mouse IgG, and NBT/BCIP substrate (Promega). Only clones deleted so as to maintain the correct reading frame yielded positive signals.

Deletions were sized by sequencing of plasmid DNA or PCR product that spanned the initiator methionine codon. To date, 19 N-terminal deletion mutants have been identified, with N-termini ranging from amino acid 5–157. An SK C-terminal deletion library was also generated by similar methods, after cloning the SK coding sequence into pGEM3Zf(+). To date, 17 C-terminal deletion clones have been identified, with C-termini ranging from amino acid 149–403. Although all C-terminal deletion clones maintained the correct reading frame, loss of the natural stop codon in ⅔ of clones resulted in the generation of SK fusion promins in which the C-terminal 6–23 amino acids consisted of irrelevant sequence derived from the flanking vector. However, subsequent analysis of these mutants (described below), suggested that this small "tail" did not significantly affect SK function.

Epitope Mapping of anti-SK Antibodies:

An epitope of a commercially-available murine anti-SK monoclonal antibody (MoAb) was partially mapped by analysis of the N- and C-terminal deletion libraries. Binding of antibody to SK was confirmed by Western blotting of bacterial cell lysates, with detection of bound MoAb by alkaline phosphatase-conjugated goat anti-mouse IgG (FIG. 7). Alternatively, bacterial cell lysates were adsorbed to 96-well Immulon 2 microtiter plates, then probed sequentially with the 2 antibodies. Negative controls revealed that background signal due to cross-reactivity with E. coli proteins was low. By this approach, it was possible to map the antibody epitope to SK residues 157–313. Generation of clones with bigger deletions from the N-terminus (i.e., past residue 157) will allow more precise localization of this epitope. Similarly, this library should prove useful in localizing epitopes of human anti-SK antibodies.

Functional Analysis of N- and C-terminal Deletion Libraries:

The functional screening of the N-terminal deletion library on casein plates suggested that clones lacking 12 or fewer N-terminal amino acids were active, whereas those lacking 18 or more N-terminal amino acids were inactive. To confirm this screening, individual mutants were expressed in E. coli, and bacterial cell lysate supernatants were prepared. These samples were incubated with human glu-plasminogen for 60 min, then chromogenic plasmin substrate (S-2251) was added.

Plasmin activity was determined by measuring the absorbance of reaction mixtures at 405 nm ($A_{405}$) in a spectrophotometer. Control experiments revealed that lysates obtained from E. coli transformed with vector alone (i.e., lacking SK insert) generated no detectable plasmin activity when incubated with plasminogen. As predicted by the initial screen, no differences in SK activity were noted when comparing wild-type protein and mutants lacking 4–12 N-terminal amino acids. However, weak, but clearly detectable activity was noted for mutants lacking 18–156 N-terminal amino acids. This activity was also confirmed in a clot lysis assay consisting of fluorescein-labeled fibrin and glu-plasminogen (20 μg/mL), in which fibrinolysis was monitored by release of fluorescein-labeled fibrin degradation products into the clot supernatant (Fay et al., 1994). Addition of 5 μL of control E. coil lysate (i.e., transformed with vector lacking an SK insert) resulted in no detectable clot lysis by 60 min. Conversely, addition of 5 μL of lysate obtained from E. coli expressing wild-type SK resulted in complete clot lysis, even when lysates were diluted up to 8000-fold prior to addition to the assay.

Deletion mutants lacking 18–156 N-terminal amino acids also induced complete clot lysis in this assay, but dilution experiments indicated that their activity was only 1–2% of wild-type SK. Since the specific activities of the deletion mutants have not yet been calculated, the comparisons of relative activities are only approximate. However, Western blot analysis of deletion mutants revealed proteins with molecular weights consistent with their predicted size based on DNA sequencing, suggesting that their reduced activity was not the result of protein degradation or instability. Similar analyses were performed on the C-terminal deletion library. All mutants lacking 40 or fewer amino acids from the C-terminus exhibited an activity indistinguishable from wild-type SK. However, all mutants lacking $\geq 51$ C-terminal amino acids exhibited no detectable activity.

Partial Localization of Plasminogen Binding Domain of SK:

An SK-binding assay has been developed in order to map regions of the SK molecule that bind plasminogen. Microtiter plates were coated overnight with human glu-plasminogen (100 ng/well), then blocked with 3% BSA. Twenty μL of the appropriate bacterial cell lysate supernatant (diluted to a volume of 100 μL by the addition of 80 μL of phosphate-buffered saline) were added to wells and incubated at room temperature for 1 hr. Wells were washed, then sequentially incubated with murine anti-SK monoclonal antibody, goat anti-mouse IgG (alkaline phosphatase-conjugated), and NBT/BCIP substrate (Promega). Control reactions revealed no significant background signal in lysates from E. coli not expressing SK, and a strong signal in cells expressing wild-type SK. Analysis of the N-terminal deletion library revealed that, in contrast to SK activity studies, clones lacking $\geq 18$ N-terminal amino acids retained the capacity to bind plasminogen. Analysis of the C-terminal deletion library revealed that all clones lacking $\leq 40$ C-terminal amino acids bound plasminogen, whereas all clones lacking $\geq 51$ C-terminal amino acids did not bind plasminogen. Hence, these results suggest that a dominant plasminogen binding domain in SK is located between amino acid residues 156–374, and that generation of more extensive N-terminal deletions may allow a more precise localization of this domain.

EXAMPLE 15

IN VIVO INVESTIGATION OF PAI-1'S MECHANISM OF ACTION

In the case of t-PA, considerable in vitro evidence implicates PAI-1 as an inhibitor of fibrinolysis at sites of arterial injury and platelet deposition. In the case of heparin (art important adjunctive therapy when t-PA is administered), ex vivo analyses of arterial platelet-rich thrombi suggest an important role for PF4 in localized heparin inactivation. To test the hypotheses that therapeutically-administered t-PA and heparin are inhibited in vivo by PAI-1 and PF4, respectively, a series of animal experiments in which these factors are inactivated by either genetic, immunologic, or peptide-based approaches are being performed.

In the case of streptokinase, it is likely that prior studies examining the antitherapeutic impact of human anti-streptokinase antibodies have been limited by the use of relatively crude immunologic and functional assays. Thus, the dominant epitopes for antibody production against streptokinase will be mapped and used to design recombinant SK molecules with reduced immunogenicity.

EXAMPLE 16

PLASMINOGEN ACTIVATOR INHIBITOR-1 (PAI-1) AND THROMBOLYSIS RESISTANCE

Rationale and Approach for Developing a Mouse Thrombotysis Model:

Experiments were designed to test the hypothesis that PAI-1 is a major determinant of the resistance of platelet-rich thrombi to lysis. PAI-1 clearly inhibits the lysis of clots in vitro. However, pathologic thrombi are different in several respects from in vitro clots. In addition, the static concentrations of factors in clot lysis assays do not adequately reflect those present in the dynamic environment of the thrombus, which interacts with flowing blood and the blood vessel wall.

A mouse model of acute arterial thrombosis is utilized. Although the size of blood vessels in mice poses technical problems, the capacity to manipulate the mouse genome allows the design of animal models with very high power to test the function of selected factors in vivo. We have obtained PAI-1-deficient mice generated by homologous recombination in embryonic stem cells (Carmeliet et al., 1993; Carmeliet et al., 1993). Mice homozygous for the null allele are absolutely deficient in PAI-1. The phenotype of these mice is quite consistent with that of the PAI-1-deficient girl that we have characterized. Neither the proband nor the "knock-out" mice bleed spontaneously, but both demonstrate biochemical evidence of an enhanced fibrinolytic state. We have also obtained mice transgenie for a murine PAI-1 cDNA minigene under the control of the CMV promoter. These mice demonstrate plasma PAI-1 levels that exceed those of normal mice by 15-fold. Similarly, serum prepared from these mice contains approx. 30-fold more PAI-1 antigen than serum from normal mice, indicating that platelet PAI-1 content in transgenie mice is significantly elevated.

The general approach of these experiments is to induce acute, platelet-rich, arterial thrombi in normal, PAI-1-deficient-, and PAI-1-over-expressing mice, then compare the sensitivity of these thrombi to lysis by t-PA. If PAI-1 is an important determinant of clot lysis resistance in vivo, then thrombi in PAI-1 knock-out mice should lyse significantly faster than thrombi in normal mice, which in turn should lyse more rapidly than those in PAI-1 transgenic mice. The use of genetic methods to alter PAI-1 expression will most likely prove superior to other potential methods (e.g., anti-PAI-1 monoclonal antibodies), since complete inactivation of PAI-1 within the thrombus (which can have limited access to the plasma compartment) is assured, and up-regulation of PAI-1 (in transgenic animals) can also be attained.

Methods for Inducing Acute Aortic Thrombi:

A variety of methods have been reported for inducing platelet-rich thrombi in arteries of small animals, such as rats, and one or more of these should prove successful in mice. Given the size of mice and the acute nature of these experiments, the abdominal aorta (mean diameter 1–2 mm) is the best site in which to initiate thrombus formation. Access to the aorta will be surgically attained, as follows:

Adult mice (5–6 weeks old; weight 20–25 g) are anesthetized by intraperitoneal injection of ketamine (3 mg), then secured in the supine position on a dissecting block.. Via a midline abdominal approach, the peritoneum is incised, and the small intestines retracted. This procedure results in direct exposure of the abdominal aorta from above the renal arteries to the level of the aortic bifurcation. It is completed within 5 min of attaining surgical anesthesia, and utilizes only superficial incisions. Experience with this model indicates that approximately 90% of mice tolerate this procedure well, maintaining normal respirations and heart rate for $\geq 1$ hr. In control experiments, it has been demonstrated that intravenous administration of human glu-plasminogen and t-PA into the inferior vena cava after exposing the aorta does not result in significant surgical bleeding. This lack of bleeding is critical to performing the proposed experiments, and probably results from the few incisions through superficial structures (abdominal wall, peritoneum) that are necessary to fully expose the abdominal aorta.

Aortic thrombi is induced by crush injury, rendered by pinching the aorta below the level of the renal arteries 3–5 times with a surgical hemostat. This technique is used to generate platelet-rich thrombi in rat aortas (Butler et al., 1992). Through this method vascular occlusion is induced within 10 min in 1 of 3 animals. The number and force of aortic compressions can be enhanced by altering with the hemostat, or by placing a partially occluding ligature around the aorta, just proximal to the site of arterial injury.

In addition, alternate methods for inducing aortic thrombi can be used. These include the use of xenon lamp with heat absorbing filter, which emits green light at a wavelength of 540 nm. The animal is injected with rose bengal (10 µg/g body weight), which absorbs light at 540 nm, and the lamp is focused on the artery by an optical fiber positioned 5 mm from the vessel. This method generates completely occlusive, platelet-rich thrombi in rat and guinea pig femoral arteries within 5–7 min of initiating photochemical injury (Matsuno et al., 1991), and it will almost certainly prove successful in mouse aortas as well. In addition, several other methods are available that have been used successfully to induce platelet-rich thrombosis in rodent small arteries, including electrical injury (Ubatuba, 1989), topical application of ferric chloride (Kurz et al., 1990), and heat-induced injury (Lenfors et al., 1993). Once aortic thrombi are successfully generated, the animals are observed for up to one hour, to document that they tolerate distal aortic obstruction, and that the rate of spontaneous thrombolysis is not high. In addition, the histologic appearance of thrombi is confirmed.

Thrombolysis Protocol:

Anesthesia and surgical exposure of the aorta will be performed as described above. After obtaining adequate aortic exposure, a doppler flow probe (1.0 mm, Crystal Biotech America) is placed on the aorta at the level of its bifurcation for monitoring blood flow. A 27 g intracath is placed in the inferior vena cava, and human glu-plasminogen (2 µg/g animal weight) is infused. Immediately thereafter, an occlusive aortic thrombus is induced by localized arterial injury below the level of the renal arteries. Time zero will be defined as the time of initiation of arterial injury. For each animal, the time to cessation of aortic blood flow is recorded. Ten minutes later, human single-chain t-PA (Genentech) is administered by bolus infusion into the inferior vena cava, followed by a continuous infusion for 30 min, as detailed below. The time to restoration of detectable aortic blood flow distal to the site of thrombus formation is recorded, as is the time required for restoration of blood flow equal to pre-thrombosis flow (or to maximal post-lysis flow, if pre-thrombosis levels are not attained).

Monitoring of aortic flow is continued for 45 min after completion of the t-PA infusion. The aorta is then ligated proximal and distal to the site of injury, then excised, and the animal is sacrificed by cervical dislocation. The ligatures on the excised aortic segment will be removed, and the lumen of the vessel is gently rinsed with 0.9% NaCl (to remove enclosed blood, but not disrupt remaining thrombus), then placed in formaldehyde for subsequent microscopic analysis.

A total of 90 mice are being studied, consisting of 30 PAI-1-deficient mice, 30 PAI-1-transgenic mice, and 30 normal mice. To control for potential strain differences, normal mice consist of appropriate littermate control animals, identified by PCR analysis of tail DNA. Within each group, 3 therapeutic subgroups are created. Ten animals receive low-dose t-PA (0.2 µg/g body weight IV bolus, followed by 0.2 µg/min for 30 min), 10 receive high-dose t-PA (1 µg/g body weight IV bolus, followed by 1 µg/min for 30 min), and 10 receive 0.9% NaCl, as control, in volumes identical to those administered to t-PA mice. Before applying these doses to all study animals, pilot studies are performed to determine t-PA doses that restore blood flow in normal mice within 30–45 min. For each therapeutic subgroup of 10 animals, the mean time from initiation of t-PA (or NaCl) to both detectable and maximal blood flow distal to the site of arterial injury is calculated.

Statistical Analysis:

The Fisher's exact test is used to compare appropriate subgroups. If PAI-1 is an important determinant of clot lysis resistance in vivo, then a 20% difference in mean time to lysis will be detected between normal mice and PAI-1-deficient mice (and between normal mice and PAI-1-transgenic mice). The number of animals planned is sufficient to detect this difference at the $p < 0.05$ level, even when accounting for a potential 15% operative death rate.

EXAMPLE 17

ATTENUATION OF THROMBOLYSIS RESISTANCE IN VIVO BY AN ANTI-PAI-1 PEPTIDE

The above experiments will most likely demonstrate an important role for PAI-1 in clot lysis resistance to t-PA. Therefore, a logical extension of these experiments is to devise methods to enhance thrombolysis in vivo by inactivating PAI-1. The experiments outlined below test the hypothesis that the P1-P14 PAI-1 peptide (SEQ ID NO: 1), which rapidly inactivates PAI-1, can enhance fibrinolysis in vivo. Mouse P1-P14 peptide has been synthesized to confirm that it inactivates murine PAI-1 in vitro. Although we anticipate no adverse effects from the intravenous infusion of this 14 amino acid peptide into mice, it will be confirmed before testing the peptide in the thrombosis model. For these preliminary experiments, P1-P14 peptide (20–200 µg, dissolved in 0.9% NaCl), is administered by tail vein injection. Blood samples are obtained from animals at timed intervals ranging from 0–120 min, and PAI-1 activity in plasma is measured. In addition, the plasma is tested for its capacity to inhibit recombinant mouse PAI-1 added in vitro. PAI-1 activity is measured by a previously described immunoactivity assay (Fay et al., 1992). If the half-life of the P1-P14 peptide is not sufficiently long to maintain adequate PAI-1 inhibition over this time period, continuous infusions of the peptide is performed.

Utilization of P1-P14 Peptide in Aortic Thrombolysis Model:

The mouse aortic injury model described in the previous section is employed. In these experiments, only normal mice will be used. Exposure of the abdominal aorta, doppler monitoring of blood flow, and cannulation of the inferior vena cava are performed exactly as described previously. Glu-plasminogen (2 µg/g animal weight) is infused, then aortic thrombosis will be induced by crush- or photoinjury. Ten minutes later, t-PA (1 µg/g body weight IV bolus, followed by 1 µg/min for 30 min) infusion is initiated, then either P1-P14 peptide (amount determined by pilot experiments described above) or an equivalent volume of 0.9% NaCl. Twenty mice receive P1-P14 peptide and 20 receive NaCl (control group). Monitoring for restoration of blood flow distal to the site of arterial injury is performed as described above. The mean time to restoration of detectable and maximal blood flow will be compared between the two groups by using the Fisher's exact test. This number of animals (even when accounting for a potential operative death rate of 15%) is sufficient to detect a >20% decrease in mean lysis time by P1-P14 peptide at the $p < 0.05$ level.

EXAMPLE 18

PLATELET FACTOR 4 AND HEPARIN RESISTANCE

As described previously, platelet-rich arterial thrombi exhibit potent heparin neutralizing activity that is mediated by platelet factor 4. The experiments outlined below test the hypothesis that the heparin neutralizing activity of arterial thrombi is sufficient to locally inactivate systemically administered heparin, and thereby compromise its antithrombotic effects. A rabbit carotid injury model is utilized, along with a monoclonal antibody to PF4 (10B2-F(ab')2, that prevents its interaction with heparin.

Rabbit Carotid Injury Model:

Rabbits are utilized because they are extensively used in thrombosis models (Eitzman et al., 1994; Mickelson et al., 1988), and because the anti-PF4 monoclonal antibody necessary for these experiments (10B2) does not cross react with PF4 from other potential species, such as pigs or dogs. New Zealand White rabbits (4–5 lb) are anesthetized by intramuscular injection of ketamine (100 mg/kg) and 6% sodium pentobarbital (1 mL/kg). Cannulas are placed in the left femoral artery for monitoring blood pressure, and into the right femoral vein for administering intravenous fluids and drugs or obtaining blood samples. The fight common carotid artery is surgically exposed, and a doppler flow probe (2.5 mm, Triton Technology) and an adjustable stainless steel mechanical constrictor will be placed on the vessel, the former proximal to the latter. The constrictor will be adjusted until the pulsatile flow pattern is reduced by 50% without altering the mean blood flow. Electrolytic injury to the intimal surface of the carotid artery is accomplished by using an intravascular electrode composed of a Teflon-insulated, silver-coated copper wire, as previously described (Rote et al., 1994). The electrode is placed between the doppler flow probe and the mechanical constrictor, and delivered current will be maintained at 100 µA. This method results in the production of a platelet-rich thrombus in several species, including rabbits.

Prior to initiating electrolytic carotid injury, rabbits (n=30) receive an intravenous heparin bolus (unfractionated porcine heparin, Elkins-Sinn, Inc; 100 U/kg), which is followed by a continuous infusion so as to maintain the APTT at 2–3 times baseline. Our prior experience with this dosing of heparin indicates that it prevents electrolytically-induced carotid thrombosis in only approximately 15% of animals. Immediately after initiation of the heparin continuous infusion, animals are infused with 10B2-F(ab')2, as follows: Group 1 (n=6) receives 10B2-F(ab')2, 0.10 mg/kg IV; Group 2 (n=6) receives 10B2-F(ab')2, 0.15 mg/kg IV; Group 3 (n=6) receives 10B2-F(ab')2, 0.20 mg/kg IV; and Group 4 (n=6) receives 10B2-F(ab')2, 0.25 mg/kg IV. A control group (Group 5, n=6) receives an equivalent volume of 0.9% NaCl.

These ranges of antibody concentrations are selected based upon prior data with monoclonal antibodies in rabbits, and upon the known stoichiometry of the 10B2-PF4 interaction. However, before performing these experiments, pilot studies are performed in which the above ranges of 10B2-F(ab')2 are sequentially administered to single rabbits. Blood samples are collected from pilot study animals between each antibody bolus, and these samples are assayed for anti-PF4 activity by sequentially adding purified PF4 (CalBiochem) and heparin, then measuring the APTT. In addition, control experiments are performed to determine whether continuous infusions of 10B2-F(ab')2 are necessary to maintain adequate anti-PF4 activity in plasma over the time course of the experiment. Based on these background experiments, adjustments in the 10B2-F(ab')2 doses outlined above may be made.

After completing 10B2-F(ab')2 or control infusions in Groups 1-5, electrolytic carotid injury is initiated, as described above, and current is applied continuously for 180 min. During this time, blood pressure, heart rate, and carotid artery flow is continuously monitored. Blood samples (1 mL) will be collected at 30 min intervals for determination of the APTT and for subsequent measurement of plasma PF4 levels by RIA (Kaplan et al., 1982). Heparin infusions are adjusted to maintain the APTT at 2-3×control. Mean time to carotid occlusion (if it occurs) is determined for each of the 5 groups. At the completion of the study protocol, the carotid artery is ligated proximal and distal to the site of electric injury, then excised. Animals are euthanized by IV administration of sodium pentobarbital. The excised carotid segment will be opened along its length, and the intact thrombus mass will be removed, weighed, then preserved for histologic analysis.

Systemic Heparin Resistance in Acute Coronary Syndromes:

The goal of these experiments is to determine the frequency and magnitude of systemic heparin resistance in patients with acute myocardial infarction and unstable angina pectoris. As discussed previously, a factor Xa inhibition assay was utilized to measure heparin resistance in 5 patients, and found detectable, but weak anti-heparin activity in 3. These studies are continuing with the goal of obtaining 50 additional patient samples.

In contrast to the pilot study of 5 patients, blood samples are collected into citrate anticoagulant that contains $PGE_1$ and theophylline, in order to minimize potential platelet activation in vitro. In addition, the number of normal individuals contributing to the reference plasma for these studies is expanded to 15.

Heparin and Hirudin in unstable angina pectoris and acute myocardial infarction is being compared. Thus, a mechanism is in place for collecting blood samples from individuals immediately upon presentation to hospital (i.e., before receiving antithrombotic therapy). Hence, it is possible to enroll the targeted number of patients for this study. The use of the factor Xa assay to measure heparin resistance will most likely prove useful, since it allows 1) screening of large number of patient plasmas simultaneously on a single microtiter plate, and 2) quantitation of the amount of heparin neutralized per mL of patient plasma by comparison to a heparin standard curve. If patients with significant anti-heparin activities in plasmas are detected (arbitrarily defined as >0.04 Units of heparin neutralized per mL of plasma), the capacity of anti-PF4 antibody (10B2) to neutralize this activity is determined. Significant neutralization of plasma anti-heparin activity by 10B2 strongly suggests that PF4 also contributes to systemic heparin resistance in the setting of acute coronary artery disease. In addition, a control population of age- and gender-matched individuals with chronic coronary artery disease is being analyzed for heparin resistance.

The charts of acute coronary disease patients with significant heparin resistance is compared to those who do not exhibit this phenomenon, to determine if heparin resistance at presentation is associated with subsequent clinical outcome (e.g., death, myocardial infarction, documented coronary artery patency if coronary angiography is performed), attainment of therapeutic APTTs (in patients randomized to heparin), or mean heparin dose indexed to body weight.

EXAMPLE 19

DETERMINATION OF DOMINANT EPITOPES RECOGNIZED BY HUMAN ANTI-STREPTOKINASE ANTIBODIES

Human anti-SK antibodies appear to inhibit SK-mediated thrombolysis, at least in some patients. In addition, high titers of anti-SK antibodies are common in patients who have received SK for myocardial infarction, thereby precluding readministration of this agent to the significant number of patients who sustain recurrent infarction. Therefore, the dominant epitopes recognized by human anti-SK antibodies are being mapped. Human sera is used to probe a library of recombinant and synthetic SK peptides. These experiments should help to define mechanisms by which anti-SK antibodies inhibit thrombolysis. In addition, they will identify candidate regions within SK for the development of mutant, less immunogenic, streptokinases.
Collection and Preparation of Patient Antisera:

Sera from patients who received streptokinase for acute myocardial infarction from 1 week to 1 year prior to blood collection is used to screen peptide libraries. This time frame is selected because several studies indicate that anti-SK antibodies are readily detectable within 1 week after treatment, and persist at high titer in many patients for at least 1 year (Jalihal et al., 1990). Patients at the Ann Arbor Veterans Affairs Hospital, and its referring network of hospitals, are routinely treated with streptokinase for acute MI. It is likely that at least 25 potential donors will be identified per year by screening patients admitted to the CCU or referred to the Cardiac Catheterization Laboratory for coronary angiography. After obtaining informed consent, blood samples (10 mL) are obtained by peripheral venipuncture or from indwelling catheters. Sera is prepared by standard methods, then stored at −70° C. until analyzed.
Streptokinase Peptide Libraries:

We use 3 sets of SK peptides for epitope mapping. The first consists of the N- and C-terminal deletion mutants discussed previously. These mutants are used to probe relatively large regions (i.e., 100-200 amino acids fragments) of the SK molecule for immunoreactive regions. Although this library should only crudely map epitopes, it proves useful for simultaneously screening large numbers of antisera. The second library consists of recombinant SK peptides, averaging 50 amino acids in length, constructed in the k phage vector, λEXlox (Novagert). This set of recombinant peptides should prove highly useful in screening individual antisera for reactivity with relatively small regions spanning the entire molecule. Finally, a synthetic library of overlapping 9 amino acid peptides is used to fine-map immunodominant regions identified by the earlier screens. This approach should prove highly efficient, and optimize the recognition of both linear and non-linear epitopes within SK.

Epitope Mapping with SK Deletion Mutants:

The following SK peptides, previously generated by N- or C-terminal deletion mutagenesis, are used to perform the initial screen of patient antisera: SK$_{1-149}$ (i.e., amino acids 1-149), SK$_{153-414}$, SK$_{251-424}$, and SK$_{314-414}$. Separate Immulon 2 microliter plates are be coated with lysate supernatants prepared from *E. coli* expressing each of these 4 fragments. The plates are blocked with 3% BSA, then 100 µL of patient sera (diluted 50-fold in phosphate buffered saline containing 1% BSA and 0.01% Tween 80) is added to each well, and incubated for 2 hours at room temp. The wells are washed, incubated with 100 µL of goat anti-human IgG alkaline phosphatase-conjugate (GIBCO BRL; 1:5000 dilution) for 1 hour, then developed by addition of alkaline phosphatase substrate (Sigma).

The absorbance (A405) of each well is measured in a Vmax microtiter plate reader (Molecular Dynamics). By adding patient antisera to each microtiter plate in the same order, it is possible to simultaneously screen up to 96 individuals for reactivity with each of these 4 peptides. This analysis has been performed with serum prepared from one individual who received SK for myocardial infarction 1 year prior to blood collection. Positive reactivity was detected with SK$_{1-149}$, SK$_{153-414}$, and SK$_{251-414}$, but not SK$_{314-414}$. Lysate supernatants derived from *E. coli* expressing wild-type SK and no SK were simultaneously analyzed for reactivity with this patient's antisera. These controls revealed that this assay is sensitive, and that background due to antibodies to *E. coli* proteins was low for this patient. However, negative and positive controls are being performed with each plate used to screen patient antisera. If background signal due to anti-*E. coli* antibodies is significant, these antibodies will be functionally removed from patient samples by one of several methods. For example, dilution of antisera into negative control (i.e., no SK) lysate supernatants, instead of PBS/BSA/Tween 80, should eliminate potential background.

Construction of Streptokinase Recombinant Fragment Library:

Patient antisera is next screened against a recombinant library of SK peptides (average length 50 amino acids), constructed in the λ phage vector, λEXlox (Novagen). This system offers several advantages, including high efficiency infection of host bacterial cells, and the capacity to rapidly screen large numbers of clones (up to 50,000 per plate) for immunoreactivity. In addition, positive clones can be automatically subcloned by Cre-loxP-mediated excision of plasmids from the phage vector.

After transformation into suitable *E. coli* strains, the resulting plasmid allows expression of cloned sequences as a fusion protein with T7 gene 10, under the control of the T7 promoter, thereby facilitating functional characterization of immunoreactive peptides. An Nde I/BamH1 fragment containing the entire coding sequence of the mature streptokinase protein will be excised from pET3a and digested with DNAase I (100 µg/mL) in 50 mM Tris-HCl (pH 7.5), 10 mM MgCl$_2$ at 25° C.

Alternatively, if the initial screening of antisera with deletion mutants suggests that SK epitopes recognized by most patients are localized to a particular region of the protein (e.g., N-terminal one-third), only that segment of corresponding DNA is used to generate recombinant peptides. At timed intervals (5-30 min), samples of the digest are removed and analyzed by agarose gel electrophoresis.

DNA from digests yielding the appropriate size fragments (100-200 bp) are end-repaired with T4 DNA polymerase, ligated to synthetic EcoRI linkers (New England Biolabs), digested with EcoRI, then subjected to agarose gel electrophoresis. Restricted DNA fragments are recovered from the gel, then ligated into EcoRI-digested λEXlox vector. Ligation mixtures will be packaged in vitro, using a commercially available λ phage packaging extract (Gigapack, Stratagene), then plated on host strain BL21(DE3). By this approach, it is possible to construct an SK fragment library containing >10$^6$ independent clones—i.e., large enough to contain any portion of the SK coding sequence in the correct orientation and reading frame over 1000 independent times.

Screening of Recombinant SK Peptide Library:

Expression of SK fragments are induced in plaques by overlaying plates with IPTG-coated nitrocellulose filters for 2 hours at 37° C., as previously described (Ginsburg et al., 1992). The filters are blocked, then incubated with patient antisera. Background activity against *E. coli* proteins is depleted by preincubating sera with immobilized *E. coli* lysates, as described (Ginsburg et al., 1986).

Bound antibody is detected by incubating filters with goat anti-human IgG-alkaline phosphatase conjugate, then NBT/BCIP (Promega). When picking positive clones, it is likely that a range of signal intensities will be observed, with the strongest positives corresponding to the most dominant SK epitopes. In addition, by varying the dilution of patient antisera, it is probably possible to facilitate the detection of the most immunoreactive peptides. Strongly positive clones are plaque purified. Inserts are amplified by PCR, and the SK sequence at the 5' and 3' ends of the insert is determined by direct sequencing of PCR products. The sequences of immunoreactive clones are aligned with that of the full-length protein. Unlike screenings of this type of library with monoclonal antibodies, it is not possible to conclude that regions of overlapping sequence between positive clones necessarily represent a shared epitope. However, clusters of positive clones are detected, with the regions of SK containing these clusters corresponding to the dominant epitopes recognized by the particular serum being screened. This approach has been applied successfully to map dominant epitopes in other proteins, such as the p23 core protein of HIV-1 (Madaule et al., 1991; Gairin et al., 1991).

Use of Synthetic Peptides for Fine Epitope Mapping:

Fine mapping of epitopes is performed by using synthetic peptides. This method has been shown to efficiently resolve linear epitopes, in some cases to a single amino acid (Geysen et al., 1984). Overlapping 9 amino acid peptides, staggered at 3 amino acid intervals, are synthesized on immobilized supports (derivatised pins), using a commercially available kit (Chiron Mimotopes Peptide Systems). These pins are positioned in blocks in an 8×12 matrix, so that they can subsequently be screened in microtiter plates.

A major advantages of this system is that the pins can be reprobed multiple times with different antisera. It is probable that the prior analysis of recombinant SK peptides will allow the identification of relatively small amino acid stretches (<50 residues) within SK for fine mapping by synthetic peptides. Pin-immobilized peptides will be screened with an ELISA strategy similar to those outlined previously. If this technique proves unsuccessful for fine epitope mapping, an alternative, commercially available method will be used, in which overlapping peptides are immobilized on reusable membranes (Cambridge Research Biomedicals).

Although no single method for epitope mapping is without pitfalls, the combination of the 3 approaches (deletion mutants, recombinant peptides, and synthetic peptides) outlined above should allow for the identification of at least some dominant epitopes within the SK protein. It is likely that most of these will constitute linear epitopes. However, analyses of larger SK fragments (deletion mutants) and recombinant SK peptides should allow for the identification of some non-linear epitopes composed of residues in relatively close proximity within the linear SK sequence.

EXAMPLE 20

GENERATION OF STREPTOKINASE VARIANTS WITH REDUCED IMMUNOREACTIVITY

The above experiments will most likely identify one or several regions within the SK molecule that constitute the dominant stimuli for antibody production in humans. It is probably then possible to introduce mutations into the SK protein that reduce or eliminate the interactions of these dominant epitopes with anti-streptokinase antibodies, while not altering the capacity of SK to activate plasminogen. Such a molecule would have obvious therapeutic utility. In the experiments outlined below, anti-SK antibodies are generated in laboratory animals that recognize the dominant epitopes for antibody production in humans. Thereafter, the streptokinase gene is randomly mutated. Then, the mutant library is expressed in $E.\ coli$. Finally, this library is screened for clones that retain biologic activity, but that have lost reac Generation of -SK antibodies.

Generation of Anti-SK Antibodies in Laboratory Animals:

For screening recombinant SK libraries for "immunosilent" clones, it is useful to have antibody preparations specifically raised against selected regions of the protein recognized as immunodominant. In addition, larger quantities of antibodies are necessary than can be obtained from the 10 mL of blood obtained from individual patients. Therefore, anti-SK antibodies are generated that recognize regions of the SK protein that are immunodominant in humans. These antibodies are then used to screen for clones with reduced immunoreactivity. To accomplish this, a multiple antigen peptide (MAP) approach is employed, in which multiple copies of a short, synthetic peptide are linked to a core matrix of branching lysine residues.

MAP peptides have been found to be highly effective in generating immune responses to synthetic peptides without the use of carder proteins Tam, 1988). Overlapping 12 amino acid peptides that span dominant SK epitopes will be synthesized as MAP peptides. New Zealand White rabbits are immunized in standard fashion, after first confirming that they do not exhibit a significant anti-SK titer.

Rabbit antisera are screened for immunoreactivity by ELISA, in which microtiter plate wells are coated with MAP peptides, then probed sequentially with antisera, goat anti-rabbit IgG-alkaline phosphatase conjugate, then substrate. Reactivity of positive antisera with wild-type SK and recombinant SK fragments that contain the epitope of interest is confirmed, as will the lack of reactivity with recombinant fragments lacking that epitope. Finally, the capacity of rabbit antibodies to compete with human anti-SK antibodies for binding to the targeted epitope is confirmed.

Since MAP peptides are not uniformly successful in inducing an effective antibody response, rabbits are also immunized with wild-type SK or purified deletion mutants appropriate for the epitope being targeted. It is likely that the pattern of immune response to SK is similar for rabbits and humans. In addition, immunization of rabbits by intravenous injection, as opposed to the subcutaneous route, may facilitate generation of the desired antibodies by mimicking the manner in which SK is presented to the immune system in patients with myocardial infarction. A panel of mouse anti-SK monoclonal antibodies is also prepared. Rabbit and murine antibodies prepared by these alternative techniques are screened for suitability, as was described above for MAP-induced antibodies.

Construction of a Streptokinase Random Mutant Library:

The coding sequence of mature SK is cloned into the λ phage vector, λEXlox (Novagen) by a PCR-based approach. Prior to cloning, T7 gene 10 sequence is deleted from the vector, so as to allow the expression of mature SK protein under the control of the T7 promoter, accomplished by Cre-loxP-mediated excision of pEXlox(+) from the phage vector, and transformation of BL21(DE3). Expression of functional SK, both from the phage construct and from the subcloned plasmid, is confirmed. Random mutagenesis is performed by error-prone PCR (Cadwell et al., 1992; Cadwell et al., 1994). The λEXlox-SK construct will serve as template DNA, and primers are complementary to regions of the vector flanking the SK insert. By increasing the concentration of $MgCl_2$ and $MnCl_2$ in Taq polymerase buffer and by providing unbalanced concentrations of dNTPs, sequence errors are introduced into the resulting PCR product.

The frequency and spectrum of mutations is determined by sequencing of PCR product, and appropriate adjustments in PCR conditions (or incorporation of additional mutagenesis methods, such as the use of hydroxylamine (Myers et al., 1985) is made in order to attain a low level of truly random mutations throughout the SK gene—i.e., approximately 0.5% error rate at the DNA level. This PCR approach has been applied successfully to PAI-1. The mutagenized PCR product is cloned into λEXlox, packaged in vitro, and used to infect BL21(DE3). Alternatively, if appropriate restriction sites can be identified flanking dominant SK epitopes, these regions are excised from the mutagenized PCR product and subcloned into λEXlox-SK. The advantage of this approach is that a more aggressive mutagenesis procedure could be performed without generating a predominantly non-functional SK library, since the majority of the resulting SK proteins would be derived from wild-type (i.e., non-mutagenized) DNA. However, cloning of the complete, mutagenized PCR product also offers certain advantages, such as the enhanced capacity to disrupt non-linear SK epitopes.

Screening of Random Library for Clones with Reduced Immunoreactivity:

The randomly mutated SK library is be screened by plating on agarose containing 1% dry milk and gluplasminogen (1 μg/mL), as described in previous studies. Lysis of $E.\ coli$ during phage replication result in clear zones of lysis around plaques synthesizing active SK. An IPTG-coated nitrocellulose filter is applied to the plates for 2 hr at 37° C., marked to record its orientation, then removed. The filter is blocked, then probed sequentially with individual anti-SK antibody preparations, species-appropriate anti-IgG-alkaline phosphatase conjugate, then substrate. Thereafter, the plates and filters are compared. Clones of interest are those that generate zones of lysis, but that do not react (or react only weakly) with anti-SK antibody, since these should represent functional, less immunoreactive SK mutants.

These clones are plaque purified, then sequenced. If multiple mutations are found in positive clones, these are independently introduced into pSELECT-SK (Promega), expressed, and characterized. This allows for the identification of the particular amino acid substitutions that disrupt interactions with anti-SK antibodies, and also serves to confirm the epitope mapping experiments performed earlier. Given the depth of libraries that can be generated by error-prone PCR approaches (>$10^6$ independent clones), we anticipate that multiple immuno-silent, yet functional mutants will be identified. In addition, by analyzing DNA sequences from independent clones, it is possible to design, by site-directed mutagenesis, new mutants that combine mutations which map to different epitopes, thereby generating even less immunoreactive proteins. Alternatively, by combining different antibody preparations during the original screening, it may be possible to directly identify particularly immuno-silent SK variants.

Functional Characterization of Selected Streptokinase Mutants:

The reduced reactivity of individual mutants with human anti-SK antibodies is confirmed by screening them against the previously prepared antisera. This is accomplished by an ELISA approach, using 96 will microtiter plates coated with wild-type SK or individual SK mutants. This allows for the rapid screening of large numbers of patient samples, and determines the extent to which the induced mutations "protect" SK from recognition by different individuals. Since some mutations may prevent or retard inhibition of SK by neutralizing antibodies, the capacity of selected mutants to lyse $^{125}$I-labeled plasma clots, prepared from individuals previously identified as exhibiting high SK-neutralizing titers, is compared to that of wild-type SK.

Prior experiences with clot lysis assays indicate that they can be performed with SK in the form of crude bacterial lysates, thereby facilitating rapid screening. The identification of mutants with enhanced fibrinolytic capacity in patients with preexisting resistance to the wild-type protein is of obvious clinical significance. Although beyond the scope of this application, it should be possible to design animal models to evaluate the efficacy of immuno-silent mutants in vivo. For example, the capacity of wild-type vs. mutant SK to boost anti-SK IgG titers could be compared in rabbits previously immunized by IV administration of wild-type SK. Alternatively, the thrombolytic efficacy of mutant SKs could be assessed in dogs (a species susceptible to plasminogen activation by SK) previously documented to exhibit high SK-neutralizing titers.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES CITED

The references listed below as well as all references cited in the specification are incorporated herein by reference to the extent that they supplement, explain, provide a background for or teach methodology, techniques and/or compositions employed herein.

Andrews P. C., Leonard D. M., Cody W. L., Sawyer T. K. Multiple and combinatorial peptide synthesis. Chemical development and biological applications. In: Pennington M. W., Dunn B. M., editors. Methods in Molecular Biology. XX ed. Totowa: Humana Press, Inc. 1994: In press Andrews P. C., Boyd J., Loo R. O., Zhao R., Zhu C.-Q., Grant K., et al. Synthesis of uniform peptide libraries and methods for physico-chemical analysis. In: Crabbe J., editor. Techniques in Protein Chemistry. In press, 1994:

Angleton P. W., Chandler W. L. and Schmer G. Diurnal variation of tissue-type plasminogen activator and its rapid inhibitor (PAI-1). Circulation 1989; 79:101–106.

Aoki N. Hemostasis associated with abnormalities of fibrinolysis. Blood Rev 1989; 3:11–17.

Bachmann F. Fibrinolysis. In: Verstraete M., Vermylen J., Lijnen H. R., Arnout J., editors. Thrombosis and Haemostasis. Leuven, Belgium: Leuven University Press, 1987:227–265.

Björk I., Ylinenjärvi K., Olson S. T., Bock P. E. Conversion of antithrombin from an inhibitor of thrombin to a substrate with reduced heparin affinity and enhanced conformational stability by binding of a tetradecapeptide corresponding to the $P_1$ to $P_{14}$ region of the putative reactive bond loop of the inhibitor. J Biol Chem 1992; 267:1976–1982.

Björk I., Nordling K., Larsson I., Olson S. T. Kinetic characterization of the substrate reaction between a complex of antithrombin with a synthetic reactive-bond loop tetradecapeptide and four target proteinases of the inhibitor. J Biol Chem 1992; 267:19047–19050.

Blond-Elguindi S., Cwirla S. E., Dower W. J., Lipshutz R. J., Sprang S. R., Sambrook J. F., et al. Affinity panning of a library of peptides displayed on bacteriophages reveals the binding specificity of BiP. Cell 1993; 75:717–728.

Booth N. A., Simpson A. J., Croll A., Bennett B., MacGregor I. R. Plasminogen activator inhibitor (PAI-1) in plasma and platelets. Br J Haematol 1988; 70:327–333.

Braaten J. V., Handt S., Jerome W. G., Kirkpatrick J., Lewis J. C., Hantgan R. R. Regulation of fibrinolysis by platelet-released plasminogen activator inhibitor 1: Light scattering and ultrastructural examination of lysis of a model platelet-fibrin thrombus. Blood 1993; 81:1290–1299.

Bruch M., Weiss V., Engel J. Plasma serine proteinase inhibitors (serpins) exhibit major conformational changes and a large increase in conformational stability upon cleavage at their reactive sites. J Biol Chem 1988; 263:16626–16630.

Brugemann J., van der Meer J., Bom V. J., van der Schaaf W., de Graeff P. A., Lie K. I. Anti-streptokinase antibodies inhibit fibrinolytic effects of anistreplase in acute myocardial infarction. Am J Cardiol 1993; 72:462–464.

Burgess W. H. Structure-function studies of acidic fibroblast growth factor. Ann N Y Acad Sci 1991; 638:89–97.

Butler K. D., Ambler J., Dolan S., Giddings J., Talbot M. D., Wallis R. B. A non-occlusive model of arterial thrombus formation in the rat and its modification by inhibitors of platelet function, or thrombin activity. Blood Coagul Fibrinolysis 1992; 3:155–165.

Cadwell R. C., Joyce G. F. Mutagenic PCR. PCR Methods and Applications 1994; 3:S136–S140.

Cadwell R. C., Joyce G. F. Randomization of genes by PCR mutagenesis. PCR Methods and Applications 1992; 2:28–33.

Cadwell R. C., Joyce G. F. Randomization of genes by PCR mutagenesis. PCR Methods and Applications 1992; 2:28–33.

Carmeliet P., Kieckens L., Schoonjans L., Ream B., Van Nuffelen A., Prendergast G., et al. Plasminogen activator inhibitor-1 gene-deficient mice. I. Generation by homologous recombination and characterization. J Clin Invest 1993; 92:2746–2755.

Carmeliet P., Stassen J. M., Schoonjans L., Ream B., van den Oord J. J., De Mol M., et al. Plasminogen activator inhibitor-1 gene-deficient mice. II. Effects on hemostasis, thrombosis, and thrombolysis. J Clin Invest 1993; 92:2756–2760.

Carrell R. W., Boswell D. R. Serpins: the superfamily of plasma serine proteinase inhibitors. In: Barrett A. J., Salvesen G., editors. Proteinase Inhibitors. Amsterdam: Elsevier Science Publishers (Biomedical Division), 1986:403–420.

Carrell R. W., Evans D. L., Stein P. E. Mobile reactive centre of serpins and the control of thrombosis. Nature 1991; 353:576–578.

Cartell R. W., Evans D. L. I. Serpins: Mobile conformations in a family of proteinase inhibitors. Curr Opin Struct Biol 1992; 2:438–446.

Carrell R. W., Owen M. C. Plakalbumin, alpha-1-antitrypsin, antithrombin and the mechanism of inflammatory thrombosis. Nature 1985; 317: 730–732.

Cartell R. W., Stein P. E., Fermi G., Wardell M. R. Biological implications of a 3 Å structure of dimeric antithrombin. Structure 1994; 2:257–270.

Cazzola F., Saggin L., Callegaro L. Production of novel monoclonal antibodies against rabbit platelet factor four. Hybridoma 1992; 11:61–69.

Cercek B., Sharifi B., Barath P., Bailey L., Forrester J. S. Growth factors in pathogenesis of coronary arterial restenosis. Am J Cardiol 1991; 68:24C-33C.

Chmielewska J., RÅnby M., Wiman B. Kinetics of the inhibition of plasminogen activators by the plasminogen-activator inhibitor. Biochem J 1988; 251:327–332.

Colucci M., Páramo J. A., Collen D. Generation in plasma of a fast-acting inhibitor of plasminogen activator in response to endotoxin stimulation. J Clin Invest 1985; 75:818–824.

Cooperman B. S., Stavridi E., Nickbarg E., Rescorla E., Schechter N. M., Rubin H. Antichymotrypsin interaction with chymotrypsin. Partitioning of the complex. J Biol Chem 1993; 268:23616–23625.

Dano K., Andreasen P. A., Grondahl-Hansen J., Kristensen P., Nielsen L. S., Skriver L. Plasminogen activators,tissue degradation,and cancer. Adv Cancer Res 1985; 44:139–266.

de Serrano V. S., Castellino F. J. Specific anionic residues of the recombinant kringle 2 domain of tissue-type plasminogen activator that are responsible for stabilization of its interaction with omega-amino acid ligands. Biochem 1993; 32:3540–3548.

de Serrano V. S., Menhart N., Castellino F. J. Expression, purification, and characterization of the recombinant kringle 1 domain from tissue-type plasminogen activator. Arch Blochem Biophys 1992; 294:282–290.

Declerck P. J., De Mol M., Alessi M. C., Baudner S., Pâques E.-P., Preissner K. T., et al. Purification and characterization of a plasminogen activator inhibitor 1 binding protein from human plasma. J Biol Chem 1988; 263: 15454–15461.

Declerck P. J., De Mol M., Vaughan D. E., Collen D. Identification of a conformationally distinct form of plasminogen activtor inhibitor-1, acting as a non-inhibitory substrate for tissue-type plasminogen activator. J Biol Chem 1992; 267:11693–11696.

Declerck P. J., Verstreken M., Kruithof EKO, Juhan-Vague I., Collen D. Measurement of plasminogen activator inhibitor 1 in biologic fluids with a murine monoclonal antibody-based enzyme-linked immunoabsorbent assay. Blood 1988; 71:220–225.

Devlin J. J., Panganiban L. C., Devlin P. E. Random peptide libraries: a source of specific protein binding molecules. Science 1990; 249:404–406.

Diéval J., Nguyen G., Gross S., Delobel J., Kruithof EKO. A lifelong bleeding disorder associated with a deficiency of plasminogen activator inhibitor type I. Blood 1991; 77:528–532.

Edelberg J. M., Reilly C. F., Pizzo S. V. The inhibition of tissue type plasminogen activator by plasminogen activator inhibitor-1. J Biol Chem 1991; 266:7488–7493.

Ehrlich H. J., Gebbink R. K., Keijer J., Linders M., Preissner K. T., Pannekoek H. Alteration of serpin specificity by a protein cofactor. J Biol Chem 1990; 265: 13029–13035.

Eitzman D. T., Chi L., Saggin L., Schwartz R. S., Lucchesi B. R., Fay W. P. Heparin neutralization by platelet-rich thrombi. Role of platelet factor 4. Circulation 1994; 89:1523–1529.

Ellis V., Dano K. Plasminogen activation by receptor-bound urokinase. Semin Thromb Hemost 1991; 17:194–200.

Erickson L. A., Ginsberg M. H., Loskutoff D. J. Detection and partial characterization of an inhibitor of plasminogen activator in human platelets. J Clin Invest 1984; 74:1465–1472.

Erickson L. A., Hekman C. M., Loskutoff D. J. The primary plasminogen-activator inhibitors in endothelial cells, platelets, serum, and plasma are immunologically related. Proc. Natl. Acad. Sci. 1985; 82:8710–8714.

Fay W. P., Eitzman D. T., Shaprio A. D., Madison E. L., Ginsburg D. Platelets inhibit fibrinolysis in vitro by both plasminogen activator inhibitor-1 dependent and independent mechanisms. Blood 1994; 83:351–356.

Fay W. P., Shapiro A. D., Shih J. L., Schleef R. R., Ginsburg D. Complete deficiency of plasminogen-activator inhibitor type 1 due to a frame-shift mutation. N Engl J Med 1992; 327:1729–1733.

Fears R., Hearn J., Standring R., Anderson J. L., Marder V. J. Lack of influence of pretreatment antistreptokinase antibody on efficacy in a multicenter patency comparison of intravenous streptokinase and anistreplase in acute myocardial infarction. Am Heart J 1992; 124:305–314.

Follo M., Ginsburg D. Structure and expression of the human gene encoding plasminogen activator inhibitor, PAI-1. Gene 1989; 84:447–453.

Fujii S., Sobel B. E. Induction of plasminogen activator inhibitor by products released from platelets. Circulation 1990; 82:1485–1493.

Gairin J. E., Madaule P., Traincard F., Barres E., Rossier J. Expression in yeast of a cDNA clone encoding a transmembrane glycoprotein gp41 fragment (a.a. 591–642) bearing the major immunodominant domain of human immunodeficiency virus. FEMS Microbiol Immunol 1991; 3:109–119.

Gennis L. S., Cantor C. R. Double-headed protease inhibitors from black-eyed peas. VI. Singlet-singlet energy transfer and other optical studies on the structure of trypsin and chymotrypsin complexes. J Biol Chem 1976; 251:769–775.

Gettins P., Harten B. Properties of thrombin- and elastase-modified human antithrombin III. Biochem 1988; 27:3634–3639.

Gettins P., Patston P. A., Schapira M. The role of conformational change in serpin structure and function. Bioessays 1993; 15:461–467.

Geysen H. M., Meloen R. H., Barteling S. J. Use of peptide synthesis to probe viral antigens for epitopes to a resolution of a single amino acid. Proc Natl Acad Sci U.S.A. 1984; 81:3998–4002.

Ginsburg D., Bockenstedt P. L., Allen E. A., Fox D. A., Foster P. A., Ruggeri Z. M., et al. Fine mapping of toonotional antibody epitopes on human von Willebrand factor using a recombinant peptide library. Thromb Haemost 1992; 67:166–171.

Ginsburg D., Handin R. I., Bonthron D. T., Donlon T. A., Bruns G. A. P., Latt S. A., et al. Human von Willebrand factor (vWF): isolation of complementary DNA (cDNA) clones and chromosomal localization. Science 1985; 228: 1401–1406.

Ginsburg D., Zeheb R., Yang A. Y., Rafferty U. M., Andreasen P. A., Nielsen L., et al. eDNA cloning of human plasminogen activator-inhibitor from endothelial cells. J Clin Invest 1986; 78:1673–1680.

GISSI 2 Investigators, A factorial randomised trial of alteplase versus streptokinase and heparin versus no heparin among 12,490 patients with acute myocardial infarction. Gruppo Italiano per lo Studio della Sopravvivenza nell'Infarto Miocardico [see comments]. Lancet 1990; 336:65–71.

Goodson R. J., Doyle M. V., Kaufman S. E., Rosenberg S. High-affinity urokinase receptor antagonists identified with bacteriophage peptide display. Proc Natl Acad Sci U.S.A. 1994; 91:7129–7133.

Grainger D. J., Kirschenlohr H. L., Metcalfe J. C., Weissberg P. L., Wade D. P., Lawn R. M. Proliferation of human smooth muscle cells promoted by lipoprotein(a). Science 1993; 260:1655–1658.

Hajjar K. A., Hamel N. M. Identification and characterization of human endothelial cell membrane binding sites for tissue plaminogen activator and urokinase. J Biol Chem 1990; 265:2908–2916.

Hamsten A., de Faire, Walldius G., Dahlen, Szamosi A., Landou C., Blombäck M., and Wiman B. Plasminogen activator inhibitor in plasma: risk factor for recurrent myocardial infraction. Lancet 1987; 2:3–9.

Hamsten A., Wiman B., de Faire U., Blombäck M. Increased plasma levels of a rapid inhibitor of tissue plasminogen activator in young survivors of myocardial infarction. N Engl J Med 1985; 313:1557–1563.

Handt S., Jerome W. G., Braaten J. V., Lewis J. C., Kirkpatrick C. J., Hantgan R. R. PAI-1 released from cultured human endothelial cells delays fibrinolysis and is incorporated into the developing fibrin clot. Fibrinolysis 1994; 8:104–112.

Hart D. A., Rehemtulla A. Plasminogen activators and their inhibitors: regulators of extracellular proteolysis and cell function. Comp Biochem Physiol [B] 1988; 90B:691–708.

Hekman C. M., Loskutoff D. J. Kinetic analysis of the interactions between plasminogen activator inhibitor 1 and both urokinase and tissue plasminogen activator. Arch Biochem Biophys 1988; 262:199–210.

Henikoff S. Ordered deletions by DNA sequencing and in vitro mutagenesis by polymerase extension and exonuclease III gapping of circular templates. Nucleic Acids Res 1990; 18:2961–2966.

Hoffmann J. J. M. L., Fears R., Bonnier J. J. R. M., Standring R., Ferres H, De Swart J. B. R. M. Significance of antibodies to streptokinase in coronary thrombolytic therapy with streptokinase or APSAC. Fibrinolysis 1988; 2:203–210.

Hogrefe H. H., Amberg J. R., Hay B. N., Sorge J. A., Shopes B. Cloning in a bacteriophage lambda vector for the display of binding proteins on filamentous phage. Gene 1993; 137:85–91.

Houghten R. A., Pinilla C., Blondelle S. E., Appel J. R., Dooley C. T., Cuervo J. H. Generation and use of synthetic peptide combinatorial libraries for basic research and drug recovery. Nature 1991; 354:84–86.

Hoylaerts M., Rijken D. C., Lijnen H. R., Collen D. Kinetics of the activation of plasminogen by human tissue plasminogen activator. J Biol Chem 1982; 257:2912–2919.

Hsia J., Kleiman N., Aguirre F., Chaitman B. R., Roberts R., Ross A. M. Heparin-induced prolongation of partial thromboplastin time after thrombolysis: relation to coronary artery patency. HART Investigators. J Am Coll Cardiol 1992; 20:31–35.

Hsueh A. J. W., Liu Y. X., Cajander S. B., Ny T. Molecular mechanisms in the hormone regulation of plasminogen activator activity in ovarian granulosa cells and cumulusoocyte complexes. In: Haseltine F. P., First N. L., editors. Meiotic Inhibition: Molecular Control of Meiosis. New York: Liss, 1988:227–258.

Huber R., Carrell R. W. Implications of the three-dimensional structure of alpha 1-antitrypsin for structure and function of serpins. Biochem 1989; 28:8951–8966.

Jalihal S., Morris G. K. Antistreptokinase titres after intravenous streptokinase [see comments]. Lancet 1990; 335:184–185.

Jang I.-K., Gold H. K., Ziskind A. A., Fallon J. T., Holt R. E., Leinbach R. C., et al. Differential sensitivity of erythrocyte-rich and platelet-rich arterial thrombi to lysis with recombinant tissue-type plasminogen activator. Circulation 1989; 79:920–928.

Kaplan K. L., Owen J. Plasma levels of platelet secretory proteins. Crit Rev Oncol Hematol 1986; 5:235–255.

Kaplan K. L., Owen J. Radioimmunoassay of platelet factor 4. Methods Enzymol 1982; 84.:83–92.

Katta V., Chait B. T. Observation of the heme-globin complex in native myoglobin by electrospray-ionization mass spectrometry. J Amer Chem Soc 1991; 113:8534–8535.

Keeton M., Eguchi Y., Sawdey M., Ahn C., Loskutoff D. J. Cellular localization of type 1 plasminogen activator inhibitor messenger RNA and protein in murine renal tissue. Am J Pathol 1993; 142:59–70.

Keijer J., Linders M., van Zonneveld A.-J., Ehrlich H. J., de Boer J.-P., Pannekoek H. The interaction of plasminogen activator inhibitor 1 with plasminogen activators (tissue-type and Urokinase-Type) and fibrin: localization of interaction sites and physiologic relevance. Blood 1991; 78:401–409.

Keijer J., Linders M., Wegman J. J., Ehrlich H J., Mertens K., Pannekoek H. On the target specificity of plasminogen activator inhibitor 1: The role of heparin, vitronectin, and the reactive site. Blood 1991; 78: 1254–1261.

Keijer J., Ehrlich H. J., Linders M., Preissner K. T., Pannekoek H. Vitronectin governs the interaction between plasminogen activator inhibitor 1 and tissue-type plasminogen activator. J Biol Chem 1991; 266:10700–10707.

Knudsen B. S., Harpel P. C., Nachman R. L. Plasminogen activator inhibitor is associated with the extracellular matrix of cultured bovine smooth muscle cells. J Clin Invest 1987; 80:1082–1089.

Kolodziej P. A., Young R. A. Epitope tagging and protein surveillance. Meth Enzymol 1991; 194:508–519.

Kost C., Stüber W., Ehrlich H. J., Pannekoek H, Preissner K. T. Mapping of binding sites for heparin, plasminogen activator inhibitor-1, and plasminogen to vitronectin's heparin-binding region reveals a novel vitronectin-dependent feedback mechanism for the control of plasmin formation. J Biol Chem 1992; 267:12098–12105.

Krishnamurti C., Alving B. M. Plasminogen activator inhibitor type 1: Biochemistry and evidence for modulation of fibrinolysis in vivo. Semin Thromb Hemost 1992; 18:67–80.

Kruithof E. K. O. Plasminogen activator inhibitors—a review. Enzyme 1988; 40:113–121.

Kunitada S., Fitzgerald G. A., Fitzgerald D. J. Inhibition of clot lysis and decreased binding of tissue-type plasminogen activator as a consequence of clot retraction. Blood 1992; 79:1420–1427.

Kurz K. D., Main B. W., Sandusky G. E. Rat model of arterial thrombosis induced by ferric chloride. Thromb Res 1990; 60:269–280.

Laemmli, U.K. Nature 1970; 227:680–685.

Lam K. S., Salmon S. E., Hersh E. M., Hruby V. J., Kazmierski W. M., Knapp R. J. A new type of synthetic peptide library for identifying ligand-binding activity [published errata appear in Nature 1992 Jul. 30; 358 (6385):434 and 1992 Dec. 24–31;360(6406):768]. Nature 1991; 354:82–84.

Lambers J. W., Cammenga M., Konig B. W., Mertens K., Pannekoek H., van Mourik J. A. Activation of human endothelial cell-type plasminogen activator inhibitor (PAI-1) by negatively charged phospholipids. J Biol Chem 1987; 262: 17492–17496.

Lang I. M., Marsh J. J., Moser K. M., Schleef R. R. Presence of active and latent type I plasminogen activator inhibitor associated with porcine platelets. Blood 1992; 80:2269–2274.

Lawrence D. A., Berkenpas M. B., Palaniappan S., Ginsburg D. Localization of vitronectin binding domain in plasminogen activator inhibitor-1. J Biol Chem 1994; 269:15223–15228. (a)

Lawrence D. A., Loskutoff D. J. Inactivation of plasminogen activator inhibitor by oxidants. Biochem 1986; 25:6351–6355.

Lawrence D. A., Olson S. T., Palaniappan S., Ginsburg D. Engineering plasminogen activator inhibitor-1 (PAI-1) mutants with increased functional stability. Biochem 1994; 33:3643–3648.

Lawrence D. A., Olson S. T., Palaniappan S., Ginsburg D. Serpin reactive-center loop mobility is required for stable inhibition but not for enzyme recognition. J Biol Chem 1994; In press.

Lawrence D. A., Strandberg L., Ericson J., Ny T. Structure-function studies of the SERPIN plasminogen activator inhibitor type 1: analysis of chimeric strained loop mutants. J Biol Chem 1990; 265:20293–20301.

Lawrence D., Strandberg L., Grundström T., Ny T. Purification of active human plasminogen activator inhibitor 1 from Escherichia coli. Comparison with natural and recombinant forms purified from eucaryotic cells. Eur J Biochem 1989; 186:523–533.

Lee M. H., Vosburgh E., Anderson K., McDonagh J. Deficiency of plasma plasminogen activator inhibitor 1 results in hyperfibrinolytic bleeding. Blood 1993; 81:2357–2362.

Lenfors S., Marberg L., Wikstrom S., Jonsson U., Eriksson A. W., Gustafsson D. A new rat model of arterial thrombosis with a platelet-rich head and an erythrocyte-rich tail: thrombolysis experiments with specific thrombin inhibition. Blood Coagul Fibrinolysis 1993; 4:263–271.

Levi M., Biemond B. J., van Zonneveld A.-J., Wouter Ten Cate J., Pannekoek H. Inhibition of plasminogen activator inhibitor-1 activity results in promotion of endogenous thrombolysis and inhibition of thrombus extension in models of experimental thrombosis. Circulation 1992; 85:305–312.

Levin E. G., Santell L. Conversion of the active to latent plasminogen activator inhibitor from human endothelial cells. Blood 1987; 70:1090–1098.

Lew A. S., Neer T., Rodriguez L., Geft I. L., Shah P. K., Ganz W. Clinical failure of streptokinase due to an unsuspected high titer of antistreptokinase antibody. J Am Coll Cardiol 1984; 4:183–185.

Lincoff A. M., Topol E. J. Illusion of reperfusion. Does anyone achieve optimal reperfusion during acute myocardial infarction? Circulation 1993; 88:1361–1374.

Lindahl T. L., Sigurdardóttir O., Wiman B. Stability of plasminogen activator inhibitor 1 (PAI-1). Thromb Haemost 1989; 62:748–751.

Loebermann H., Tokuoka R., Deisenhofer J., Huber R. Human_$\alpha_1$-proteinase inhibitor. Crystal structure analysis of two crystal modifications, molecular model and preliminary analysis of the implications for function. J Mol Biol 1984; 177:531–557.

Loskutoff D. J. Regulation of PAI-1 gene expression. Fibrinolysis 1991; 5:197–206.

Loskutoff D. J., Sawdey M., Mimuro J. Type 1 plasminogen activator inhibitor. Prog Hemost Thromb 1989; 9:87–115.

Lowman H. B., Bass S. H., Simpson N., Wells J. A. Selecting high-affinity binding proteins by monovalent phage display. Biochem 1991; 30:10832–10838.

Madaule P., Gairin J. E., Benichou S., Rossier J. A peptide library expressed in yeast reveals new major epitopes from human immunodeficiency virus type 1. FEMS Microbiol Immunol 1991; 3:99–107.

Madison E. L., Goldsmith E. J., Gerard R. D., Gething M. H., Sambrook J. F., Bassel-Duby R. S. Amino acid residues that affect interaction of tissue-type plasminogen activator with plasminogen activator inhibitor 1. Proc Natl Acad Sci USA 1990; 87:3530–3533.

Maraganore J. M., Bourdon P., Adelman B., Cannon C., Theroux P. Heparin variability and resistance: Comparisons with a direct thrombin inhibitor. Circulation 1992; 86:I-386 Abstract.

Marder V. J. Recombinant streptokinase: opportunity for an improved agent [letter]. Blood Coagul Fibrinolysis 1993; 4:1039–1040.

Matsudaira P. Sequence from picomole quantities of proteins electroblotted onto polyvinylidene difluoride membranes. J Biol Chem 1987; 262:10035–10038.

Matsuka Y. V., Medved L. V., Brew S. A., Ingham K. C. The NH2-terminal fibrin-binding site of fibronectin is formed by interacting fourth and fifth finger domains. Studies with recombinant finger fragments expressed in Escherichia coli. J Biol Chem 1994; 269:9539–9546.

Matsuno H., Uematsu T., Nagashima S., Nakashima M. Photochemically induced thrombosis model in rat femoral artery and evaluation of effects of heparin and tissue-type plasminogen activator with use of this model. J Pharmacol Methods 1991; 25:303–317.

Matthews D. J., Wells J. A. Substrate Phage: Selection of protease substrates by monovalent phage display. Science 1993; 260:1113–1117.

Menhart N., McCance S. G., Sehl L. C., Castellino F. J. Functional independence of the kringle 4 and kringle 5 regions of human plasminogen. Biochem 1993; 32:8799–8806.

Menhart N., Sehl L. C., Kelley R. F., Castellino F. J. Construction, expression, and purification of recombinant kringle 1 of human plasminogen and analysis of its interaction with omega-amino acids. Biochem 1991; 30:1948–1957.

Mickelson J. K., Simpson P. J., Lucchesi B. R. Myocardial dysfunction and coronary vasoconstriction induced by platelet-activating factor in the post-infarcted rabbit isolated heart. J Mol Cell Cardiol 1988; 20:547–561.

Mimuro J., Loskutoff D. J. Binding of Type 1 plasminogen activator inhibitor to the extracellular matrix of cultured bovine endothelial cells. J Biol Chem 1989; 264:5058–5063. (a)

Mimuro J., Loskutoff D. J. Purificaion of a protein from bovine plasma that binds to type plasminogen activator inhibitor and prevents its interaction with extracellular matrix. J Biol Chem 264:936–939. (b)

Mizuno K., Satomura K., Miyamoto A., Arakawa K., Shibuya T., Arai T., et al. Angioscopic evaluation of coronary-artery thrombi in acute coronary syndromes. N Engl J Med 1992; 326:287–291.

Mimuro J., Schleef R. R., Loskutoff D. J. Extracellular matrix of cultured bovine aortic endothelial cells contains functionally active type I plasminogen activator inhibitor. Blood 1987; 70:721–728.

Moran D. M., Standring R., Lavender E. A., Harris G. S. Assessment of anti-streptokinase antibody levels in human sera using a microradioimmunoassay procedure. Thromb Haemost 1984; 52:281–287.

Moscatelli D., Rifldn D. B. Membrane and matrix localization of proteinases: a common theme in tumor cell invasion and anglogenesis. Biochim Biophys Acta 1988; 948:67–85.

Mottonen J., Strand A., Symersky J., Sweet R. M., Danley D. E., Geoghegan K. F., et al. Structural basis of latency in plasminogen activator inhibitor-1. Nature 1992; 355:270–273.

Murphy J. G., Schwartz R. S., Edwards W. D., Camrud A. R., Vlietstra R. E., Holmes D. R., Jr. Percutaneous polymeric stents in porcine coronary arteries. Initial experience with polyethylene terephthalate stents. Circulation 1992; 86:1596–1604.

Myers R. M., Lerman L. S., Maniatis T. A general method for saturation mutagenesis of clones DNA fragments. Science 1985; 229:242–247.

Naski M. C., Lawrence D. A., Mosher D. F., Podor T. J., Ginsburg D. Kinetics of inactivation of α-thrombin by plasminogen activator inhibitor-1: Comparison of the effects of native and urea-treated forms of vitronectin. J Biol Chem 1993; 268: 12367–12372.

Novokhatny V. V., Ingham K. C. Domain structure of the Fib-1 and Fib-2 regions of human fibronectin. Thermodynamic properties of the type I finger module. J Mol Biol 1994; 238:833–844.

Ny T., Sawdey M., Lawrence D., Millan J. L., Loskutoff D. J. Cloning and sequence of a eDNA coding for the human β-migrating endothelial-cell-type plasminogen activator inhibitor. Proc Natl Acad Sci USA 1986; 83:6776–6780.

Ohlsson M., Peng X. R., Liu Y. X, Jia X. C., Hsueh A. J., Ny T. Hormone regulation of tissue-type plasminogen activator gene expression and plasminogen activator-mediated proteolysis. Semin Thromb Hemost 1991; 17:286–290.

Plow E. F., Felez J., Miles L. A. Cellular regulation of fibrinolysis. Thromb Haemost 1991; 66:32–36.

Pöllänen J., Stephens R. W., Vaheri A. Directed plasminogen activation at the surface of normal and malignant cells. Adv Cancer Res 1991; 57:273–328.

Potter van Loon B. J., Rijken D. C., Brommer E. J. P. and Van der Maas A. P. C. The amount of plasminogen, tissue-type plasminogen activator and plasminogen activator inhibitor type 1 in human thrombi and the relation to ex-vivo lysibility. Thromb Haemost 1992; 67:101–105.

Preissner K. T., Holzhüter S., Justus C., Muller-Berghaus G. Identification and partial characterization of platelet vitronectin: Evidence for complex formation with platelet-derived plasminogen activator inhibitor-1. Blood 1989; 74:1989–1996.

Pyke C., Kristensen P., Ralfkiaer E., Eriksen J., Dano K. The plasminogen activation system in human colon cancer: messenger RNA for the inhibitor PAI-1 is located in endothelial cells in the tumor stroma. Cancer Res 1991; 51:4067–4071.

Rebar E. J., Pabo C. O. Zinc finger phage: Affinity selection of fingers with new DNA-binding specificities. Science 1994; 263:671–673.

Reed G. L., Kussie P., Parhami-Seren B. A functional analysis of the antigenicity of streptokinase using monoclonal antibody mapping and recombinant streptokinase fragments. J Immunol 1993; 150:4407–4415.

Reilly C. F., Fujita T., Mayer E. J., Siegfried M. E. Both circulating and clot-bound plasminogen activator inhibitor-1 inhibit endogenous fibrinolysis in the rat. Arterioscler Thromb 1991; 11:1276–1286.

Reilly C. F., Hutzelmann J. E. Plasminogen activator inhibitor-1 binds to fibrin and inhibits tissue-type plasminogen activtor-mediated fibrin dissolution. J Biol Chem 1992; 267:17128–17135.

Roberts B. L., Marklad W., Ley A. C., Kent R. B., White D. W., Guterman S. K., et al. Directed evolution of a protein: Selection of potent neutrophil elastase inhibitors displayed on M13 fusion phage. Proc Natl Acad Sci USA 1992; 89:2429–2433.

Rote W. E., Nedelman M. A., Mu D. X., Manley P. J., Weisman H., Cunningham M. R., et al. Chimeric 7E3 prevents carotid artery thrombosis in cynomolgus monkeys. Stroke 1994; 25:1223–32; discussion 1233.

Rothbard R. L., Fitzpatrick P. G., Francis C. W., Caton D. M., Hood W. B., Jr., Marder V. J. Relationship of the lytic state to successful reperfusion with standard- and low-dose intracoronary streptokinase. Circulation 1985; 71:562–570.

Rucinski B., Poggi A., James P., Holt J. C., Niewiarowski S. Purification of two heparin-binding proteins from porcine platelets and their homology with human secreted platelet proteins. Blood 1983; 61:1072–1080.

Saksela O., Rifkin D. B. Cell-associated plasminogen activation: regulation and physiological functions. Annu Rev Cell Biol 1988; 4:93–126.

Salonen E.-M., Vaheri A., Pollanen J., Stephens R., Andreasen P. A., Mayer M., et al. Interaction of plasminogen activator inhibitor (PAI-1) with vitronectin. J Biol Chem 1989; 264:6339–6343.

Sambrook J., Fritsch E. F., Maniatis T. Molecular cloning: a laboratory manual. 2nd ed. Cold Spring Harbor, N.Y.: Cold Spring Harbor Laboratory Press, 1989.

Sawdey M. S., Loskutoff D. J. Regulation of murine type 1 plasminogen activator inhibitor gene expression in vivo. Tissue specificity and induction by lipopolysaccharide, tumor necrosis factor-a, and transforming growth factor-β. J Clin Invest 1991; 88:1346–1353.

Schatz P. J. Use of peptide libraries to map the substrate specificity of a peptide-modifying enzyme: A 13 residue consensus peptide specifies biotinylation in *Escherichia coli*. Bio/technol 1993; 11:1138–1143.

Schechter N. M., Jordan L. M., James A. M., Cooperman B. S., Wang Z. m., Rubin H. Reaction of human chymase with reactive site variants of al-antichymotrypsin. Modulation of inhibitor versus substrate properties. J Biol Chem 1993; 268:23626–23633.

Schleef R. R., Higgins D. L., Pillemer E., Levitt L. J. Bleeding diathesis due to decreased functional activity of Type 1 plasminogen activator inhibitor. J Clin Invest 1989; 83:1747–1752.

Schneiderman J., Sawdey M. S., Keeton M. R., Bordin G. M., Bernstein E. F., Dilley R. B., et al. Increased type 1 plasminogen activator inhibitor gene expression in atherosclerotic human arteries. Proc Natl Acad Sci USA 1992; 89:6998–7002.

Schreuder H. A., de Boer B., Dijkema R., Mulders J., Theunissen H. J. M., Grootenhuis P. D. J., et al. The intact and cleaved human antithrombin III complex as a model for serpin-proteinase interactions. Structural Biology 1994; 1:48–54.

Schulze A. J., Baumann U., Knof S., Jaeger E., Huber R., Laurell C. Structural transition of $a_1$-antitrypsin by a peptide sequentially similar to _β-strand s4A. Eur J Biochem 1990; 194:51–56.

Schulze A. J., Huber R., Degryse E., Speck D., Bischoff R. Inhibitory activity and conformational transition of a__-proteinase inhibitor variants. Eur J Biochem 1991; 202:1147–1155.

Schwartz B. L., Light-Wahl K. J., Smith R. D. Observation of noncovalent complexes to the avidin tetraruer by electrospray ionization mass spectrometry. J Am Soc Mass Spectrom 1994; 5:201–204.

Seiffert D., Loskutoff D. J. Evidence that Type I plasminogen activator inhibitor binds to the Somatomedin B domain of Vitronectin. J Biol Chem 1991; 266:2824–2830.

Seiffert D., Loskutoff D. J. Kinetic analysis of the interaction between type 1 plasminogen activator inhibitor and vitronectin and evidence that the bovine inhibitor binds to a thrombin-derived amino-terminal fragment of bovine vitronectin. Biochim Biophys Acta 1991; 1078:23–30.

Sherman P. M., Lawrence D. A., Yang A. Y., Vandenberg E. T., Paielli D., Olson S. T., et al. Saturation mutagenesis of the plasminogen activator inhibitor-1 reactive center. J Biol Chem 1992; 267:7588–7595.

Shubeita H. E., Cottey T. L., Franke A. E., Gerard R. D. Mutational and immunochemical analysis of plasminogen activator inhibitor 1. J Biol Chem 1990; 265:18379–18385.

Sigurdardóttir O., Wiman B. Complex formation between plasminogen activator inhibitor 1 and vitronectin in purified systems and in plasma. Biochim Biophys Acta 1990; 1035:56–61.

Sitko G. R., Ramjit D. R., Stabilito I. I., Lehman D., Lynch J. J., Vlasuk G. P. Conjunctive enhancement of enzymatic thrombolysis and prevention of thrombotic reocclusion with the selective factor Xa inhibitor, tick anticoagulant peptide. Comparison to hirudin and heparin in a canine model of acute coronary artery thrombosis. Circulation 1992; 85:805–815.

Smith G. P., Scott J. K. Libraries of peptides and proteins displayed on filamentous phage. Methods Enzymol 1993; 217:228–257.

Sprengers E. D., Akkerman J. W., Jansen B. G. Blood platelet plasminogen activator inhibitor: two different pools of endothelial cell type plasminogen activator inhibitor in human blood. Thromb Haemost 1986; 55:325–329.

Stein P. E., Leslie A. G. W., Finch J. T., Turnell W. G., McLaughlin P. J., Carrell R. W. Crystal structure of ovalbumin as a model for the reactive centre of serpins. Nature 1990; 347:99–102.

Steinberg I. Z. Long-range nonradiative transfer of electronic excitation energy in proteins and polypeptides. Annu Rev Biochem 1971; 40:83–114.

Strandberg L., Lawrence D. A., Johansson L. B., Ny T. The oxidative inactivation of plasminogen activator inhibitor type 1 results from a conformational change in the molecule and does not require the involvement of the P1' methionine. J Biol Chem 1991; 266:13852–13858.

Strandberg L., Lawrence D., Ny T. The organization of the human plasminogen-activator-inhibitor 1 gene. Eur J Biochem 1988; 176:609–616.

Stryer L. Fluorescence spectroscopy of proteins. Science 1968; 162:526–533.

Studier F. W., Rosenberg A. H., Dunn J. J., Dubendorff J. W. Use of T7 RNA polymerase to direct expression of cloned genes. Meth Enzymol 1990; 185:60–89.

Tam J. P. Synthetic peptide vaccine design: synthesis and properties of a high-density multiple antigenic peptide system. Proc Natl Acad Sci USA 1988; 85:5409–5413.

Tomasini B. R., Mosher D. F. Vitronectin. Prog Hemost Thromb 1991; 10:269–305.

Ubatuba F. B. An animal model for the study of arterial thrombosis. Braz J Med Biol Res 1989; 22:993–1000.

van Mourik J. A., Lawrence D. A., Loskutoff D. J. Purification of an inhibitor plasminogen activator (anitactivator) synthesized by endothelial cells. J Biol Chem 1984; 259:14914–14921.

Vassalli J.-D., Sappino A.-P., Belin D. The plasminogen activator/plasmin system. J Clin Invest 1991; 88:1067–1072.

Vaughan D. E., Declerck P. J., Van Houtte E., De Mol M., Collen D. Studies of recombinant plasminogen activator inhibitor-1 in rabbits. Pharmacokinetics and evidence for reactivation of latent plasminogen activator inhibitor-1 in vivo. Circ Res 1990; 67:1281–1286.

Vijaya S., Elango N., Zavala F., Moss B. Transport to the cell surface of a peptide sequence attached to the truncated C terminus of an N-terminally anchored integral membrane protein. Mol Cell Biol 1988; 8:1709–1714.

Wagner O. F., de Vries C., Hohmann C., Veerman H., Pannekoek H. Interaction between plasminogen activator inhibitor type 1 (PAI-1) bound to fibrin and either tissue-type plasminogen activator (t-PA) or urokinase-type plasminogen activator (uPA). J Clin Invest 1989; 84:647–655.

Wallén P. Biochemistry of plasminogen. In: Kline D. L., Reddy K. N. N., editors. Fibrinolysis. Boca Raton: CRC Press, 1980: 1–25.

Warnes C. A., Roberts W. C. Sudden coronary death: comparison of patients with to those without coronary thrombus at necropsy. Am J Cardiol 1984; 54:1206–1211.

Weitz J. I., Hudoba M., Massel D., Maraganore J., Hirsh J. Clot-bound thrombin is protected from inhibition by heparin-antithrombin III but is susceptible to inactivation by antithrombin III-independent inhibitors. J Clin Invest 1990; 86:385–391.

Wertz G. W., Collins P. L., Huang Y., Gruber C., Levine S., Ball L. A. Nucleotide sequence of the G protein gene of human respiratory syncytial virus reveals an unusual type of viral membrane protein. Proc Natl Acad Sci USA 1985; 82:4075–4079.

Wiman B., Almquist A., Sigurdardottir O., Lindahl T. Plasminogen activator inhibitor 1 (PAI) is bound to vitronectin in plasma. FEBS Lett 1988; 242:125–128.

Wiman B., Chmielewska J., Ranby M. Inactivation of tissue plasminogen activator in plasma. Demonstration of a complex with a new rapid inhibitor. J Biol Chem 1984; 259:3644–3647.

What is claimed:

1. An isolated peptide having a length of less than approximately 30 amino acids and comprising an amino acid sequence in accordance with SEQ ID NO:1, SEQ ID NO:2, SEQ ID NO:3, SEQ ID NO:4 or SEQ ID NO:5, wherein the amino terminus of said peptide is an amino terminal threonine.

2. The peptide of claim 1 comprising SEQ ID NO:1.
3. The peptide of claim 1 comprising SEQ ID NO:2.
4. The peptide of claim 1 comprising SEQ ID NO:3.
5. The peptide of claim 1 comprising SEQ ID NO:4.
6. The peptide of claim 1 comprising SEQ ID NO:5.
7. The peptide of claim 1, wherein the amino terminal threonine of said peptide is protected.
8. The peptide of claim 7, wherein said amino terminal threonine is protected by amidation or acetylation of said amino terminal threonine.
9. The peptide of claim 1 having a length of less than approximately 20 amino acids.
10. A method of promoting clot lysis by decreasing the half-life of active plasminogen activator inhibitor-1, said method comprising exposing said active plasminogen activator inhibitor-1 to an effective amount of a peptide in accordance with claim 1.
11. The method of claim 10, wherein the effective amount of said peptide is an amount that decreases the in vitro half-life of said active plasminogen activator inhibitor-1 to between about 1 and about 98 minutes.
12. The method of claim 10, wherein the effective amount of said peptide is an amount that decreases the in vitro half-life of said active plasminogen activator inhibitor-1 to between about 1 and about 10 minutes.
13. A method of promoting clot lysis by decreasing the half-life of active plasminogen activator inhibitor-1 in the presence of vitronectin, said method comprising exposing said active plasminogen activator inhibitor-1 to an effective amount of a peptide in accordance with claim 1.
14. The method of claim 13, wherein the effective amount of said peptide is an amount that decreases the in vitro half-life of said active plasminogen activator inhibitor-1 to to between about 1 and about 190 minutes.

15. The method of claim 13, wherein the effective amount of said peptide is an amount that decreases the in vitro half-life of said active plasminogen activator inhibitor-1 to to about 110 to about 130 minutes.

16. A method of promoting lysis of platelet rich clots by decreasing the half-life of active plasminogen activator inhibitor-1, said method comprising exposing said active plasminogen activator inhibitor-1 to an effective amount of a peptide in accordance with claim 1.

17. The method of claim 16, wherein the effective amount of said peptide is an amount that decreases the in vitro half-life of said active plasminogen activator inhibitor-1 to to between about 1 and about 190 minutes.

18. The method of claim 16, wherein the effective amount of said peptide is an amount that decreases the in vitro half-life of said active plasminogen activator inhibitor-1 to to about 110 to about 130 minutes.

19. A method of promoting clot lysis by decreasing the half-life of active plasminogen activator inhibitor-1 in an animal, said method comprising:
  (a) combining a therapeutically effective amount of the peptide of claim 1 with a pharmacologically acceptable carrier to form a pharmaceutical composition; and
  (b) introducing said composition into the blood stream of the animal.

20. The method of claim 19, wherein said animal is a human.

21. The method of claim 19, wherein the therapeutically effective amount of said peptide is an amount that decreases the in vitro half-life of active plasminogen activator inhibitor-1 to between about 1 and about 98 minutes.

22. The method of claim 19, wherein the therapeutically effective amount of said peptide is an amount that decreases the in vitro half-life of active plasminogen activator inhibitor-1 to between about 1 and about 10 minutes.

23. A method of promoting clot lysis by decreasing the half-life of active plasminogen activator inhibitor-1 in the presence of vitronectin in an animal, said method comprising:

(a) combining a therapeutically effective amount of the peptide of claim 1 with a pharmacologically acceptable carrier to form a pharmaceutical composition; and introducing said composition into the blood stream of the animal.

24. The method of claim 23, wherein said animal is a human.

25. The method of claim 23, wherein the therapeutically effective amount of said peptide is an amount that decreases the in vitro half-life of active plasminogen activator inhibitor-1 to between about 1 and about 190 minutes.

26. The method of claim 23, wherein the therapeutically effective amount of said peptide is an amount that decreases the in vitro half-life of active plasminogen activator inhibitor-1 to between about 110 and about 130 minutes.

27. The method of claim 19, wherein said pharmacologically acceptable carrier comprises an excipient for parenteral administration.

28. The method of claim 19, wherein said pharmacologically acceptable carrier comprises an excipient for oral administration.

29. A pharmaceutical composition comprising a therapeutically effective amount of a peptide in accordance with claim 1 and a pharmaceutically acceptable carrier.

30. The method of claim 10, wherein said peptide comprises the amino acid sequence of SEQ ID NO: 1.

31. The method of claim 13, wherein said peptide comprises the amino acid sequence of SEQ ID NO: 1.

32. The method of claim 16, wherein said peptide comprises the amino acid of sequence of SEQ ID NO: 1.

33. The method of claim 19, wherein said peptide comprises the amino acid of sequence of SEQ ID NO: 1.

34. The method of claim 23, wherein said peptide comprises the amino acid of sequence of SEQ ID NO: 1.

35. The pharmaceutical composition of claim 29, wherein said peptide comprises the amino acid sequence of SEQ ID NO: 1.

36. The method of claim 10, wherein said peptide comprises the amino acid sequence of SEQ ID NO:2.

37. The method of claim 10, wherein said peptide comprises the amino acid sequence of SEQ ID NO:3.

38. The method of claim 10, wherein said peptide comprises the amino acid sequence of SEQ ID NO:4.

39. The method of claim 10, wherein said peptide comprises the amino acid sequence of SEQ ID NO:5.

40. The method of claim 13, wherein said peptide comprises the amino acid sequence of SEQ ID NO:2.

41. The method of claim 13, wherein said peptide comprises the amino acid sequence of SEQ ID NO:3.

42. The method of claim 13, wherein said peptide comprises the amino acid sequence of SEQ ID NO:4.

43. The method of claim 13, wherein said peptide comprises the amino acid sequence of SEQ ID NO:5.

44. The method of claim 16, wherein said peptide comprises the amino acid sequence of SEQ ID NO:2.

45. The method of claim 16, wherein said peptide comprises the amino acid sequence of SEQ ID NO:3.

46. The method of claim 16, wherein said peptide comprises the amino acid sequence of SEQ ID NO:4.

47. The method of claim 16, wherein said peptide comprises the amino acid sequence of SEQ ID NO:5.

48. The method of claim 19, wherein acid sequence said peptide comprises the amino of SEQ ID NO:2.

49. The method of claim 19, wherein said peptide comprises the amino acid sequence of SEQ ID NO:3.

50. The method of claim 19, wherein said peptide comprises the amino acid sequence of SEQ ID NO:4.

51. The method of claim 19, wherein said peptide comprises the amino acid sequence of SEQ ID NO:5.

52. The method of claim 23, wherein said peptide comprises the amino acid sequence of SEQ ID NO:2.

53. The method of claim 23, wherein said peptide comprises the amino acid sequence of SEQ ID NO:3.

54. The method of claim 23, wherein said peptide comprises the amino acid sequence of SEQ ID NO:4.

55. The method of claim 23, wherein said peptide comprises the amino acid sequence of SEQ ID NO:5.

56. The pharmaceutical composition of claim 29, wherein said peptide comprises the amino acid sequence of SEQ ID NO:2.

57. The pharmaceutical composition of claim 29, wherein said peptide comprises the amino acid sequence of SEQ ID NO:3.

58. The pharmaceutical composition of claim 29, wherein said peptide comprises the amino acid sequence of SEQ ID NO:4.

59. The pharmaceutical composition of claim 29, wherein said peptide comprises the amino acid sequence of SEQ ID NO:5.

* * * * *

UNITED STATES PATENT AND TRADEMARK OFFICE
CERTIFICATE OF CORRECTION

PATENT NO.   :   5,639,726

DATED        :   June 17, 1997

INVENTOR(S)  :   Lawrence et al.

It is certified that error appears in the above-identified patent and that said Letters Patent is hereby corrected as shown below:

In claim 14, column 82, line 32, delete "to".
In claim 15, column 82, line 36, delete "to about 110 to" and insert --between about 110 and-- therefor.
In claim 17, column 82, line 45, delete "to".
In claim 18 column 82, line 49, delete "to about 110 to" and insert --between about 110 and-- therefor.
In claim 48, column 84, line 19, delete "acid sequence".
In claim 48, column 84, line 20, after 'amino', insert --acid sequence--.

Signed and Sealed this

Fourth Day of November, 1997

Attest:

BRUCE LEHMAN

Attesting Officer

Commissioner of Patents and Trademarks